United States Patent
Ding et al.

(10) Patent No.: US 10,555,949 B2
(45) Date of Patent: Feb. 11, 2020

(54) PYRROLOPYRIMIDINE COMPOUNDS USED AS TLR7 AGONIST

(71) Applicant: CHIA TAI TIANQING PHARMACEUTICAL GROUP CO., LTD., Lianyungang (CN)

(72) Inventors: Zhaozhong Ding, Shanghai (CN); Hao Wu, Shanghai (CN); Fei Sun, Shanghai (CN); Lifang Wu, Shanghai (CN); Ling Yang, Lianyungang (CN)

(73) Assignee: CHIA TAI TIANQING PHARMACEUTICAL GROUP CO., LTD., Lianyungang, Jiangsu (CN)

( * ) Notice: Subject to any disclaimer, the term of this patent is extended or adjusted under 35 U.S.C. 154(b) by 0 days.

(21) Appl. No.: 15/955,523

(22) Filed: Apr. 17, 2018

(65) Prior Publication Data

US 2018/0303832 A1 Oct. 25, 2018

Related U.S. Application Data

(63) Continuation of application No. 15/503,977, filed as application No. PCT/CN2015/086909 on Aug. 14, 2015, now Pat. No. 9,962,388.

(30) Foreign Application Priority Data

Aug. 15, 2014 (CN) .......................... 2014 1 0405136
Jul. 6, 2015 (CN) .......................... 2015 1 0392499

(51) Int. Cl.
| | |
|---|---|
| A61K 31/519 | (2006.01) |
| C07D 487/04 | (2006.01) |
| C07D 207/02 | (2006.01) |
| C07D 265/28 | (2006.01) |
| C07D 471/04 | (2006.01) |

(52) U.S. Cl.
CPC .......... *A61K 31/519* (2013.01); *C07D 207/02* (2013.01); *C07D 265/28* (2013.01); *C07D 471/04* (2013.01); *C07D 487/04* (2013.01)

(58) Field of Classification Search
CPC ........................... A61K 31/519; C07D 487/04
USPC ........................................ 514/265.1; 544/280
See application file for complete search history.

(56) References Cited

U.S. PATENT DOCUMENTS

| 6,028,076 A | 2/2000 | Hirota et al. |
| 6,329,381 B1 | 12/2001 | Kurimoto et al. |
| 9,962,388 B2 * | 5/2018 | Ding .................... A61K 31/519 |

FOREIGN PATENT DOCUMENTS

| JP | 2009-504803 A | 2/2009 |
| JP | 2014-504644 A | 2/2014 |
| WO | WO-2007/024707 A2 | 3/2007 |
| WO | WO-2009/005687 A1 | 1/2009 |
| WO | WO-2009/019553 A2 | 2/2009 |
| WO | WO-2010/077613 A1 | 7/2010 |
| WO | WO-2012/106522 A2 | 8/2012 |
| WO | WO-2014/056953 | 4/2014 |
| WO | WO-2014/081643 | 5/2014 |
| WO | WO-2014/081643 A1 | 5/2014 |
| WO | WO-2014/081644 | 5/2014 |
| WO | WO-2014/081645 | 5/2014 |
| WO | WO-2015/124591 A1 | 8/2015 |
| WO | WO-2015/168269 A1 | 11/2015 |
| WO | WO-2015/168279 A1 | 11/2015 |
| WO | WO-2016/107536 A1 | 7/2016 |

OTHER PUBLICATIONS

Australian First Examination Report, issued in Australian Patent Application No. 2015303558 (dated Jan. 16, 2018).
Canadian Examiner's Report, issued in Canadian Patent Application No. 2,958,097 (dated Mar. 14, 2018).
Chilean Office Action, issued in Chilean Patent Application No. 201700379.
Chinese Office Action, issued in Chinese Patent Application No. 201580041989.3 (dated Jul. 20, 2018).
Database Registry CAS RN 1392818-28-8 (dated Aug. 29, 2012).
Eurasian First Office Action, issued in Eurasian Patent Application No. 201790389.
Eurasian Second Office Action, issued in Eurasian Patent Application No. 201790389.
European Extended Search Report, issued in European Patent Application No. 15831451.8 (dated Jan. 4, 2018).
Greene, et al., "Protective Groups in Organic Synthesis", 2nd Ed., pp. 362-385 (1991).
Hoffmann, "The immune response of *Drosophila*", Nature 426: 33-38 (2003).
Indian Examination Report, issued in Indian Patent Application No. 201717007964 (dated Jan. 21, 2019).
Israeli Office Action, issued in Israeli Patent Application No. 250586 (dated Sep. 12, 2018).

(Continued)

*Primary Examiner* — Jeffrey H Murray
(74) *Attorney, Agent, or Firm* — Foley & Lardner LLP

(57) ABSTRACT

The present invention relates to a pyrrolopyrimidine compound as TLR7 agonist, and particularly relates to a compound of formula (I) or a pharmaceutically acceptable salt thereof, a preparation process thereof, a pharmaceutical composition containing such compounds and use thereof for manufacturing a medicament against viral infection.

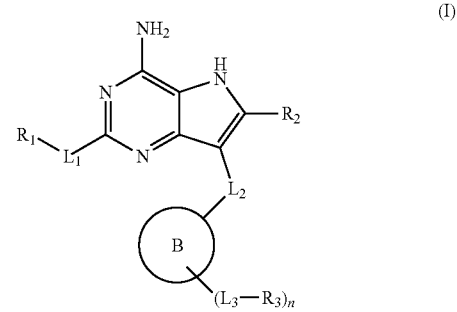

14 Claims, 1 Drawing Sheet

(56) References Cited

OTHER PUBLICATIONS

Japanese Office Action, issued in Japanese Patent Application No. 2017-527961 (dated Dec. 19, 2017).
Kanzler, et al., "Therapeutic targeting of innate immunity with Toll-like receptors agonists and antagonists", Nature Medicine 13(5): 552-559 (2007).
Korean Office Action, issued in Korean Patent Application No. 10-2017-7007194 (dated Nov. 14, 2018).
Maehr, "A Proposed New Convention for Graphic Presentation of Molecular Geometry and Topography", Journal of Chemical Education 62(2): 114-120 (1985).
Otmar, et al., "Synthesis and antiproliferative activity of 2,6-diamino-9-benzyl-9-deazapurine and related compounds", Bioorganic & Medicinal Chemistry 12(12): 3187-3195 (2004).
Remington, The Science and Practice of Pharmacy, 21st. Ed., Ch. 39-42, 89 pages (2005).
Roethle, et al., "Identification and Optimization of Pteridinone Toll-like Receptor 7 (TLR7) Agonists for the Oral Treatment of Viral Hepatitis", J. Med. Chem. 56(18): 7324-7333 (2013).
Singaporean Search Report, issued in Singaporean Patent Application No. 11201701169X (dated Dec. 12, 2017).
Singaporean Written Opinion, issued in Singapore Patent Application No. 11201701169X (dated Dec. 20, 2017).
Taiwanese Office Action, issued in Taiwanese Patent Application No. 104133088 (dated Apr. 28, 2016).
Takeda, et al., "Toll-Like Receptors", Annu. Rev. Immunol. 21: 335-376 (2003).
Ukrainian Office Action, issued in Ukrainian Patent Application No. a 2017 02350.
Ulevitch, "Therapeutics Targeting the Innate Immune System", Nature Reviews—Immunology: 4: 512-520 (2004).
Vietnamese Office Action, issued in Vietnamese Patent Application No. 1-2017-00930 (dated Nov. 30, 2018).
Written Opinion of the International Searching Authority, issued in International Application No. PCT/CN2015/086909 (dated Nov. 11, 2015).
International Search Report and Written Opinion for PCT/CN2015/086909 dated Nov. 11, 2015, with English translation.
Notice of Allowance on U.S. Appl. No. 15/503,977 dated Jan. 9, 2018.
Office Action on U.S. Appl. No. 15/503,977 dated Aug. 24, 2017.
Otmar, M. et al.. "Synthesis and antiproliferative activity of 1-2, 4, 6-13 2,6-diamino-9-benzyl-9-deazapurine and related compounds", Bioorganic & Medicinal Chemistry, vol. 12, No. /, May 10, 2004 (May 10, 2004), pp. 3187-3195, compound 7.
Australian First Examination Report, issued in Australian Pat. Appln. No. 2018236899, 2 pages (dated Mar. 16, 2019).
Chinese Office Action, issued in Chinese Pat. Appln. No. 201580041989.3, 8 pages (dated Apr. 22, 2019).
Indonesian Office Action, issued in Indonesian Pat. Appln. No. P00201701572, 3 pages (dated Jun. 12, 2019).
Israeli Office Action, issued in Israeli Pat. Appln. No. 250586, 3 pages (dated Jun. 6, 2019).
Japanese Office Action, issued in Japanese Pat. Appln. No. 2018-079330, 6 pages (dated May 7, 2019).
Korean Office Action, issued in Korean Pat. Appln. No. 10-2017-7007194, 9 pages (dated Apr. 29, 2019).
Final Office Action, issued in Korean Pat. App. No. 10-2017-7007194, 8 pages (dated Jul. 19, 2019).
Lima, et al., "Bioisosterism: a Useful Strategy for Molecular Modification and Drug Design", Current Medicinal Chemistry 12: 23-49 (2005).
Office Action, issued in Japanese Pat. App. No. 2018-079330, 2 pages (dated Aug. 27, 2019).
Office Action, issued in Philippines Pat. App. No. 1/2017/500281, 4 pages (dated Jul. 1, 2019).
Third Office Action, issued in Chinese App. No. 201580041989.3, 8 pages (dated Jul. 18, 2019).

* cited by examiner

PYRROLOPYRIMIDINE COMPOUNDS USED AS TLR7 AGONIST

This application is a continuation application which claims priority to U.S. patent application Ser. No. 15/503,977, filed Feb. 14, 2017, entitled "PYRROLOPYRIMIDINE COMPOUNDS USED AS TLR7 AGONIST," which application is a U.S. National Stage of International Application No. PCT/CN2015/086909, filed on Aug. 14, 2015, designating the United States, and claiming the benefit of Chinese Patent Application No. 201410405136.0, filed with the Chinese Patent Office on Aug. 15, 2014 and of Chinese Patent Application No. 201510392499.X, filed with the Chinese Patent Office on Jul. 6, 2015, all of which are hereby incorporated by reference in their entireties.

TECHNICAL FIELD

The present invention relates to a novel pyrrolopyrimidine cyclic compound as TLR7 agonist or a pharmaceutically acceptable salt thereof and particularly relates to a compound of formula (I) or a pharmaceutically acceptable salt thereof.

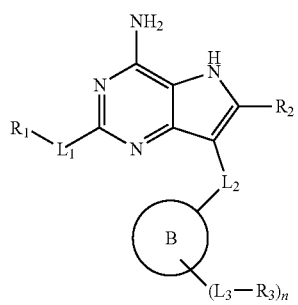

BACKGROUND

Toll-like receptor is expressed by various immune cells and recognizes high reserved structural motifs: Pathogen Associated Molecular Pattern (PAMP) expressed by microorganism pathogens or Damage Associated Molecular Patterns (DAMP) released by dead cells. PAMP or DAMP stimulates Toll-like receptor to trigger signal cascade which induces the activations of transcriptional factors like AP-1, NF-κB and interferon regulators (pulse response function). It results in various cell responses, including productions of interferons, proinflammatory cytokines and effector cytokines, whereby immune response is produced. By far, 13 types of Toll-like receptors have been discovered. Toll-like receptors 1, 2, 4, 5 and 6 are mainly expressed on the cell surface while Toll-like receptors 3, 7, 8 and 9 are expressed in the endosome. Different Toll-like receptors recognize ligands derived from different pathogens. Toll-like receptor 7 (TLR7) is expressed and ligand recognized by plasmaeytoid dendritic cells (pDC) to induce the secretion of interferon α (IFN-α). Toll-like receptor 7 (TLR7) and Toll-like receptor 8 (TLR8) are highly homologous and therefore the ligand of TLR7 in most cases is also that of TLR8. TLR8 stimulation mainly induces the productions of cytokines like tumor necrosis factor α (TNF-α) and chemoattractant. Interferon α is one of the medicines for treating chronic hepatitis B or hepatitis C while TNF-α is a proinflammatory cytokine, of which the over secretion will result severe side effects. Therefore, the selectivity for TLR7 and TLR8 is important for the development of TLR7 agonist for treating virus infective diseases. There have been reported several TLR7 agonists, like imiquimod, resiquimod, GS-9620. Nevertheless, it is desirable to have novel TLR7 agonists with better selectivity, activity and safety. We have identified a series of novel pyrrolopyrimidine derivates as TLR7 agonist. The background of our research may be found at the following journals: Hoffmann, J. A., Nature, 2003, 426, p 33-38; Akira, S., Takeda, K., and Kaisho, T., Annual. Rev. Immunology, 2003, 21, 335-376; Ulevitch, R. J., Nature Reviews. Immunology, 2004, 4, 512-520; Coffman, R. L., Nat. Med. 2007, 13, 552-559; Paul A. Roethle, J. Med. Chem. 2013, 56 (18), 7324-7333.

SUMMARY

Provided is a compound of formula (I) or a pharmaceutically acceptable salt thereof,

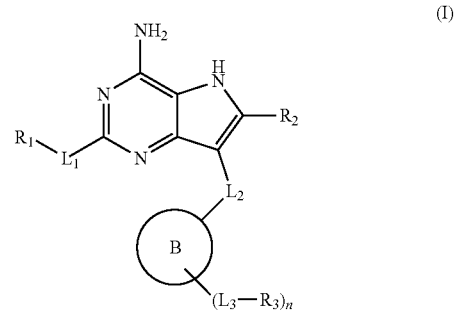

wherein
$L_1$ and $L_2$ are each independently selected from the group consisting of —O—, —$CH_2$—, —S—, —NH—, —NHC(=O)—, —C(=O)—, —C(=O)NH—, —S(=O)—, —S(=O)$_2$—, —NHS(=O)$_2$— and —S(=O)$_2$NH—, wherein the above —$CH_2$—, —NH—, —NHC(=O)—, —C(=O)NH—, —NHS(=O)$_2$— and —S(=O)$_2$NH— are optionally substituted by one or more $R_4$;
$R_1$ is selected from the group consisting of hydrogen, $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, aryl and heteroaryl, wherein the above $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, aryl and heteroaryl are optionally substituted by one or more $R_4$;
$R_2$ is selected from the group consisting of hydrogen, halogen, cyano, hydroxyl, thiol, amino, COOH, —$CONH_2$, $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, aryl and heteroaryl, wherein the above hydroxyl, thiol, amino, COOH, —$CONH_2$, $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, aryl and heteroaryl are optionally substituted by one or more $R_4$;
B is selected from the group consisting of $C_{3-10}$ cyclohydrocarbyl, 3-10 membered heterocyclohydrocarbyl, aryl and heteroaryl;
$L_3$ is selected from the group consisting of $C_{0-6}$ alkylene, imino, —O—, —S—, —S(=O)— and —S(=O)$_2$—, wherein the above $C_{0-6}$ alkylene and imino are optionally substituted by one or more $R_4$;

$R_3$ is selected from the group consisting of hydrogen, amino, $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, aryl and heteroaryl, wherein the above amino, $C_{1-10}$ alkyl, $C_{2-10}$ alkenyl, $C_{2-10}$ alkynyl, $C_{3-10}$ cyclohydrocarbyl, 3-10 membered heterocyclohydrocarbyl, aryl and heteroaryl are optionally substituted by one or more $R_4$; or $R_3$ and $L_3$ together with the adjacent atom at the ring B form a saturated or unsaturated 5-8 membered ring, the 5-8 membered ring is optionally substituted by one or more $R_4$; n is 0, 1, 2, 3, 4 or 5;

$R_4$ is selected from the group consisting of halogen, cyano, —R, —OR, =O, —SR, —NR$_2$, =NR, —C(halogen)$_3$, —CR (halogen)$_2$, —CR$_2$ (halogen), —OCN, —SCN, —N=C=O, —NCS, —NO, —NO$_2$, —NRC(=O)R, —NRC(=O)OR, —NRC(=O)NRR, —C(=O)NRR, —C(=O)OR, —OC(=O)NRR, —OC(=O)OR, —C(=O)R, —S(=O)$_2$OR, —S(=O)$_2$R, —OS(=O)$_2$OR, —S(=O)$_2$NRR, —S(=O)R, —NRS(=O)$_2$R, —NRS(=O)$_2$NRR, —NRS(=O)$_2$OR, —OP(=O)(OR)$_2$, —P(=O)(OR)$_2$, —C(=O)R, —C(=S)R, —C(=O)OR, —C(=S)OR, —C(=O)SR, —C(=S)SR, —C(=O)NRR, —C(=S)NRR, —C(=NR)NRR and —NRC(=NR)NRR; R is independently selected from the group consisting of H, $C_{1-8}$ alkyl, $C_{3-8}$ cyclohydrocarbyl, 3-8 membered heterocyclohydrocarbyl, aryl, heteroaryl, arylalkyl and heteroarylalkyl; and when $L_1$ is —CH$_2$— or —NH—, $R_3$ is not H.

In some embodiments of the compound of formula (I), $L_1$ and $L_2$ are each independently selected from the group consisting of —O—, —CH$_2$—, —S—, —NH—, —C(=O)—, —S(=O)— and —S(=O)$_2$—, wherein the above —CH$_2$— and —NH— are optionally substituted by one or more $R_4$. In some embodiments of the compound of formula (I), $L_1$ and $L_2$ are each independently selected from the group consisting of —O—, —CH$_2$—, —S— and —NH—, wherein the above —CH$_2$— and —NH— are optionally substituted by one or more $R_4$. In some embodiments of the compound of formula (I), $L_1$ and $L_2$ are each independently selected from the group consisting of —O— and —CH$_2$—, wherein the above —CH$_2$— is optionally substituted by one or more $R_4$.

In some embodiments of the compound of formula (I), $R_1$ is selected from the group consisting of hydrogen, $C_{1-6}$ alkyl, $C_{2-6}$ alkenyl, $C_{2-6}$ alkynyl, $C_{3-6}$ cyclohydrocarbyl, 3-6 membered heterocyclohydrocarbyl, aryl and heteroaryl, wherein the above $C_{1-6}$ alkyl, $C_{2-6}$ alkenyl, $C_{2-6}$ alkynyl, $C_{3-6}$ cyclohydrocarbyl, 3-6 membered heterocyclohydrocarbyl, aryl and heteroaryl are optionally substituted by one or more $R_4$. In some embodiments of the compound of formula (I), $R_1$ is selected from the group consisting of $C_{1-6}$ alkyl, wherein the above $C_{1-6}$ alkyl is optionally substituted by one or more $R_4$.

In some embodiments of the compound of formula (I), $R_2$ is selected from the group consisting of hydrogen, halogen, cyano, hydroxyl, thiol, amino, CHO, COOH, —CONH$_2$, $C_{1-6}$ alkyl, $C_{2-6}$ alkenyl, $C_{2-6}$ alkynyl, $C_{3-6}$ cyclohydrocarbyl, 3-6 membered heterocyclohydrocarbyl, aryl and heteroaryl, wherein the above hydroxyl, thiol, amino, CHO, COOH, —CONH$_2$, $C_{1-6}$ alkyl, $C_{2-6}$ alkenyl, $C_{2-6}$ alkynyl, $C_{3-6}$ cyclohydrocarbyl, 3-6 membered heterocyclohydrocarbyl, aryl and heteroaryl are optionally substituted by one or more $R_4$. In some embodiments of the compound of formula (I), $R_2$ is selected from the group consisting of hydrogen, halogen, cyano, hydroxyl, amino, —CONH$_2$ and $C_{1-6}$ alkyl, wherein the above hydroxyl, amino, —CONH$_2$ and $C_{1-6}$ alkyl are optionally substituted by one or more $R_4$. In some embodiments of the compound of formula (I), $R_2$ is selected from the group consisting of hydrogen, cyano and —CONH$_2$, wherein the above —CONH$_2$ is optionally substituted by one or more $R_4$.

In some embodiments of the compound of formula (I), B is selected from the group consisting of aryl and heteroaryl. In some embodiments of the compound of formula (I), B is selected from the group consisting of 5-7 membered aryl and 5-7 membered heteroaryl. In some embodiments of the compound of formula (I), B is selected from the group consisting of phenyl, pyridyl pyrimidinyl, pyridazinyl, pyrazinyl, thienyl, thiazolyl, furyl, oxazolyl, thidiazolyl, isoxazolyl, oxdiazolyl, pyrrolyl, imidazolyl, pyrazolyl, isothiazolyl and triazolyl. In some embodiments of the compound of formula (I), B is selected from the group consisting of phenyl and pyridyl.

In some embodiments of the compound of formula (I), $L_3$ is selected from the group consisting of $C_{0-6}$ alkylene, wherein the above $C_{0-6}$ alkylene is optionally substituted by one or more $R_4$.

In some embodiments of the compound of formula (I), $R_3$ is selected from the group consisting of hydrogen, amino, $C_{1-6}$ alkyl, $C_{2-6}$ alkenyl, $C_{2-6}$ alkynyl, $C_{3-8}$ cyclohydrocarbyl, 3-8 membered heterocyclohydrocarbyl, aryl and heteroaryl, wherein the above amino, $C_{1-6}$ alkyl, $C_{2-6}$ alkenyl, $C_{2-6}$ alkynyl, $C_{3-8}$ cyclohydrocarbyl, 3-8 membered heterocyclohydrocarbyl, aryl and heteroaryl are optionally substituted by one or more $R_4$; or $R_3$ and $L_3$ together with the adjacent atom at the ring B form a saturated or unsaturated 5-8 membered ring, the 5-8 membered ring is optionally substituted by one or more $R_4$. In some embodiments of the compound of formula (I), $R_3$ is selected from the group consisting of hydrogen, amino, $C_{1-6}$ alkyl, $C_{3-8}$ cyclohydrocarbyl, 3-8 membered heterocyclohydrocarbyl, aryl and heteroaryl, wherein the above amino, $C_{1-6}$ alkyl, $C_{3-8}$ cyclohydrocarbyl, 3-8 membered heterocyclohydrocarbyl, aryl and heteroaryl are optionally substituted by one or more $R_4$; or $R_3$ and $L_3$ together with the adjacent atom at the ring B form a saturated or unsaturated 5-8 membered ring, the 5-8 membered ring is optionally substituted by one or more $R_4$.

In some embodiments of the compound of formula (I), $R_4$ is selected from the group consisting of halogen, cyano, —R, —OR, =O, —SR, —NR$_2$, =NR, —C(halogen)$_3$, —CR (halogen)$_2$, —CR$_2$ (halogen), —OCN, —SCN, —N=C=O, —NCS, —NO, —NO$_2$, —NRC(=O)R, —C(=O)NRR, —C(=O)OR, —OC(=O)NRR, —C(=O)R, —S(=O)$_2$OR, —S(=O)$_2$R, —OS(=O)$_2$OR, —S(=O)$_2$NRR, —S(=O)R, —NRS(=O)$_2$R, —C(=O)R, —C(=O)OR and —C(=O)NRR. In some embodiments of the compound of formula (I), $R_4$ is selected from the group consisting of halogen, cyano, —R, —OR, =O, —NR$_2$, =NR, —C(halogen)$_3$, —CR (halogen)$_2$ and —CR$_2$ (halogen). In some embodiments of the compound of formula (I), $R_4$ is selected from the group consisting of halogen, —R, —OR and =O.

In some embodiments, the compound of formula (I) is selected from the following compounds:

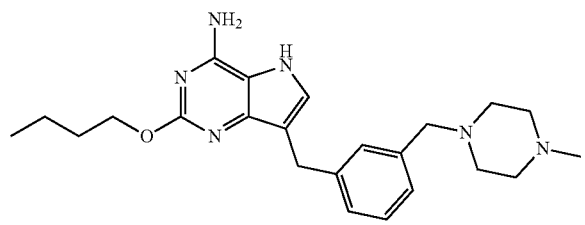 [SMILES: CCCCOc1nc(N)c2[nH]cc(Cc3cccc(CN4CCN(C)CC4)c3)c2n1]

-continued
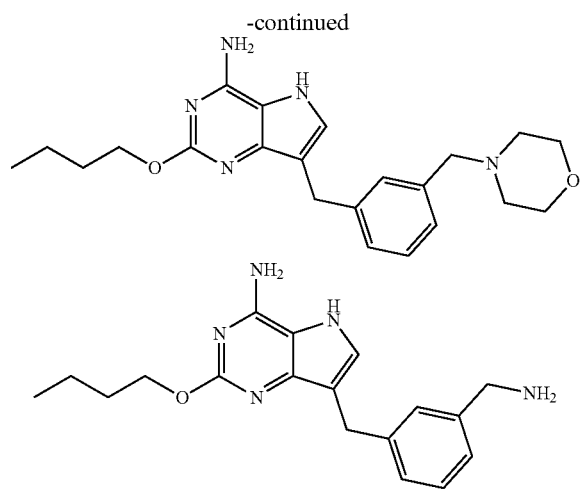
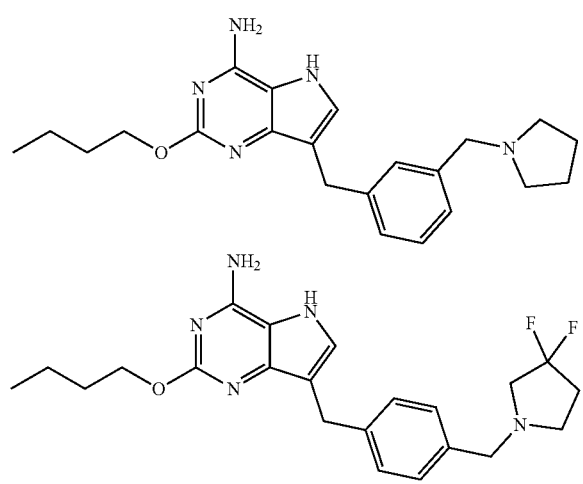
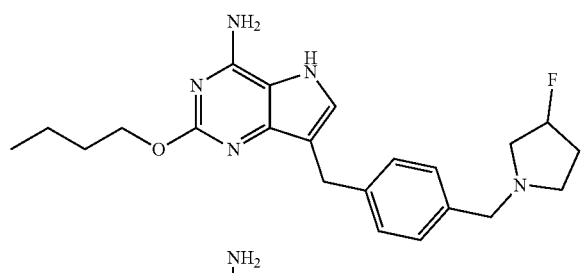
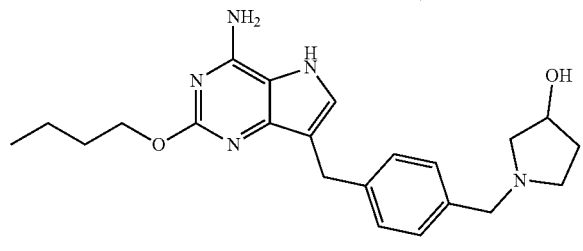
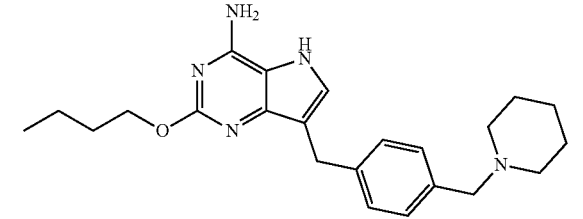
-continued
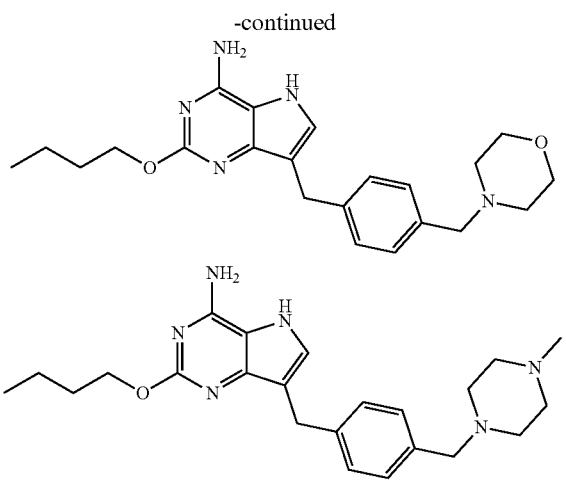
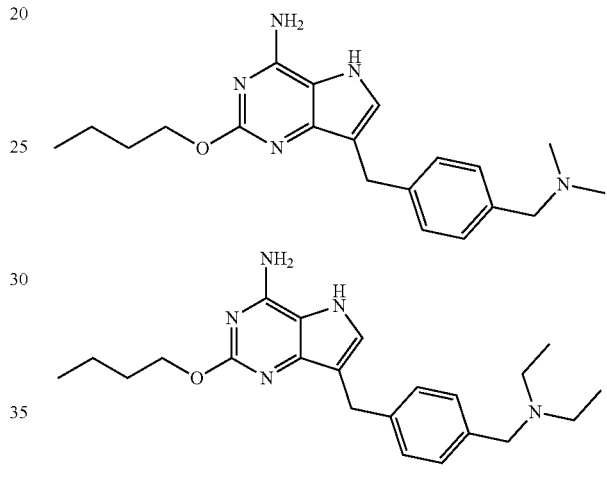
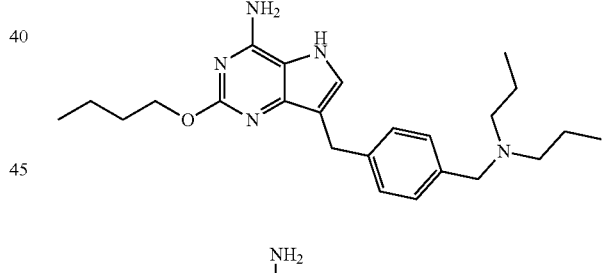
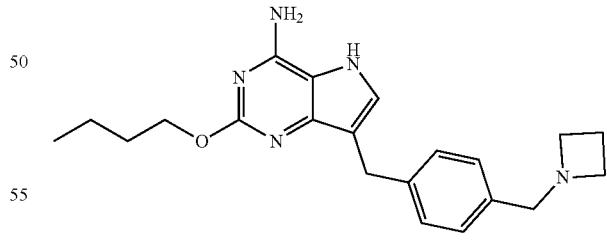
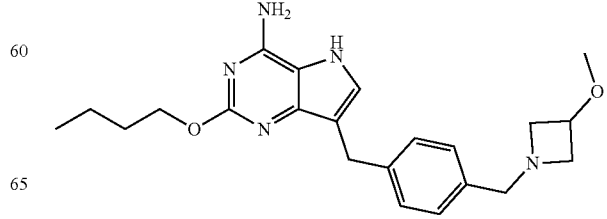

-continued
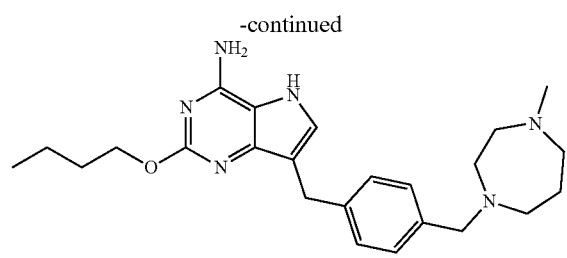
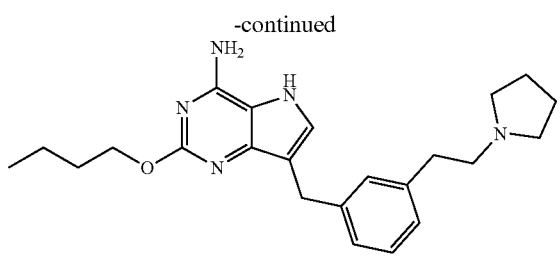
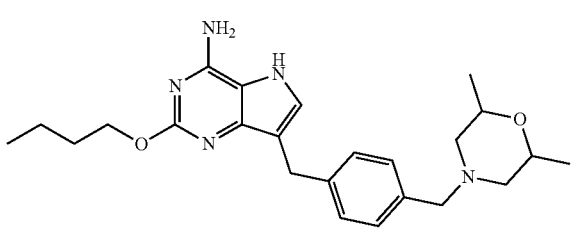
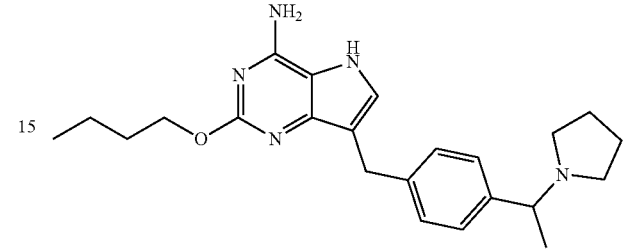
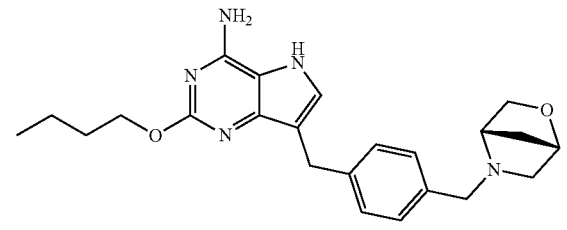
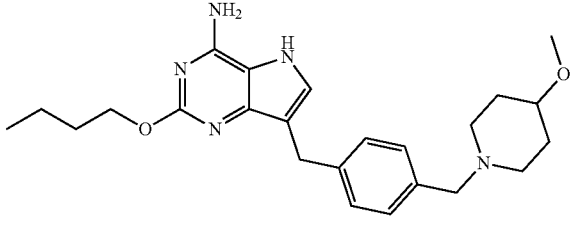
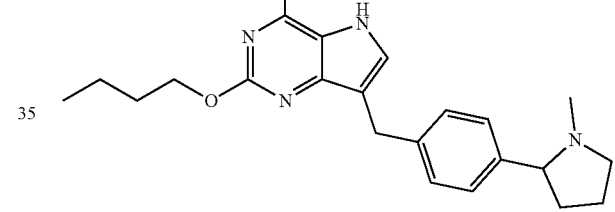
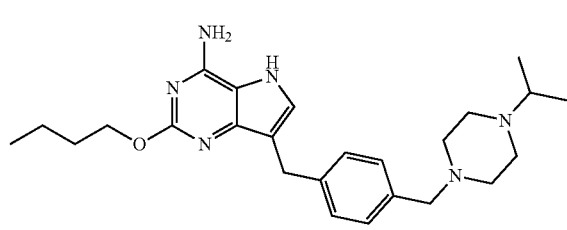
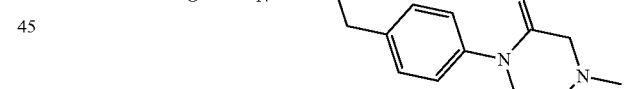
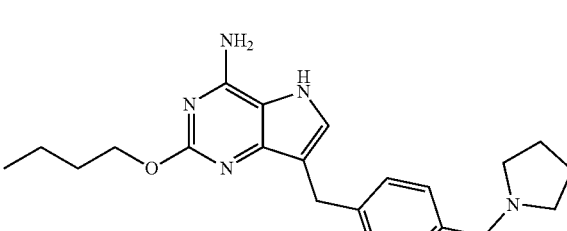
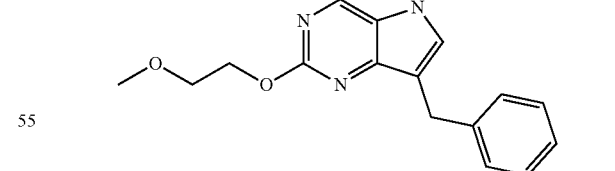
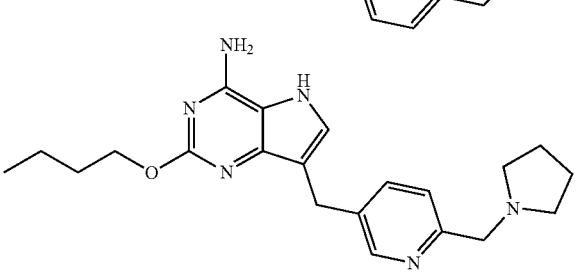
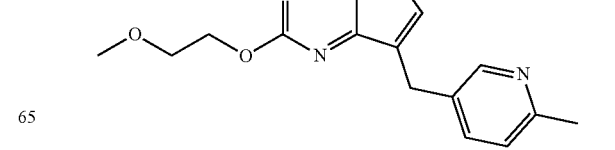

-continued
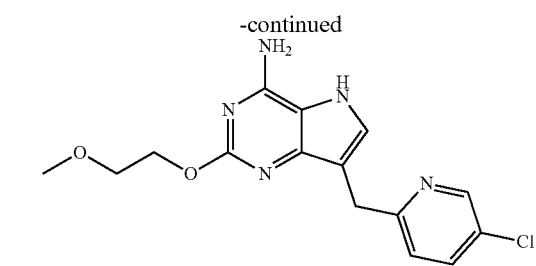
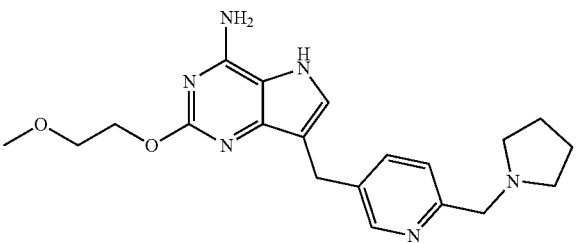
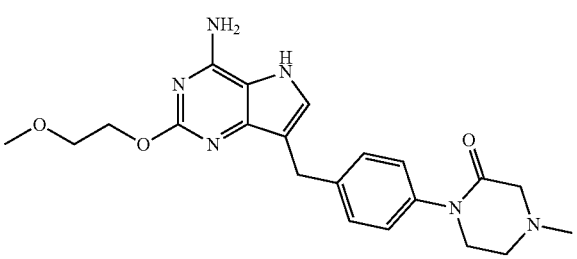
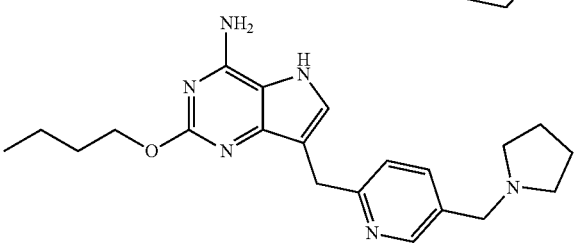
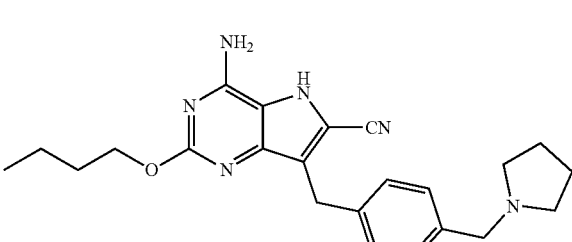
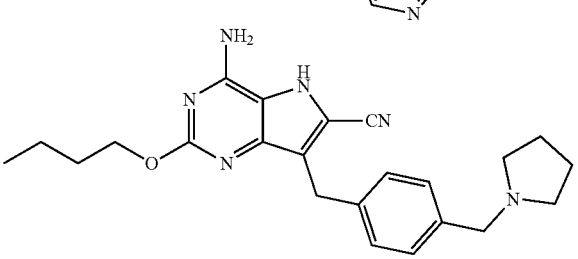
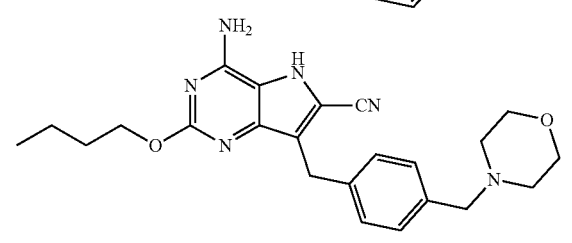
-continued
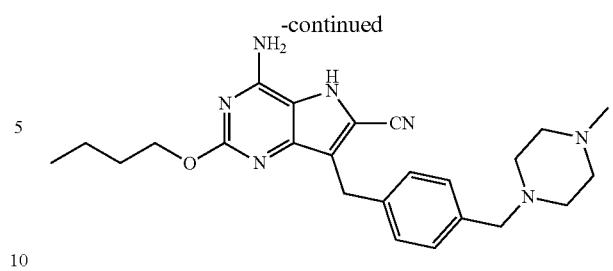
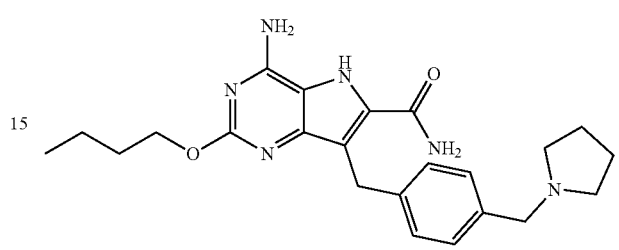
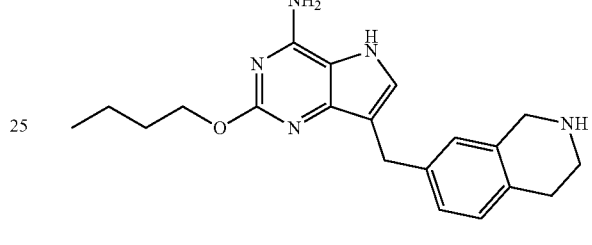
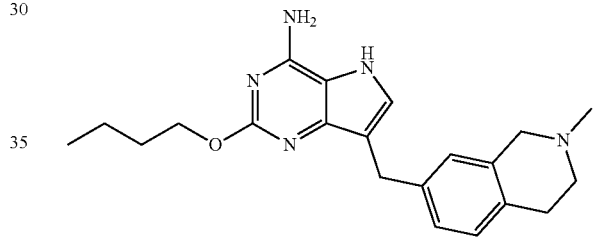
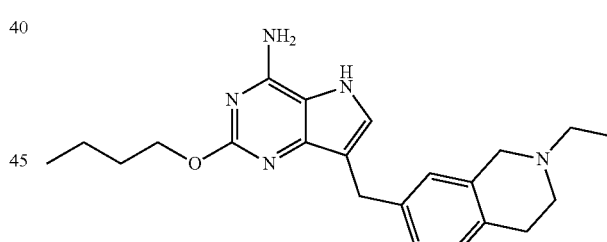
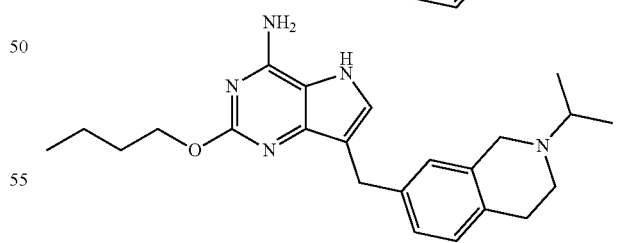
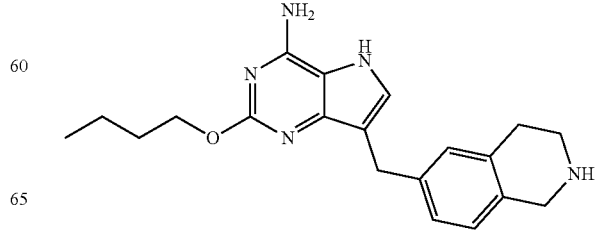

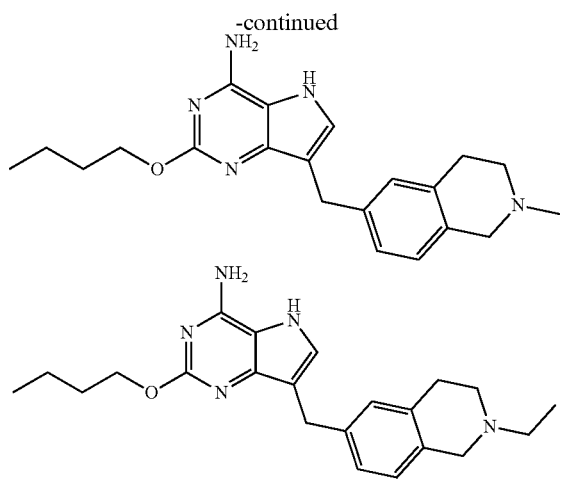

or pharmaceutically acceptable salts thereof.

In another aspect, provided is a method for treating viral infection, comprising administering a compound of formula (I) or a pharmaceutically acceptable salt thereof in therapeutically effective amount.

In yet another aspect, provided is use of a compound of formula (I) or a pharmaceutically acceptable salt thereof for the manufacture of a medicament for treating viral infection.

In some embodiments, the viral infection is the infection of dengue fever virus, yellow fever virus, west nile virus, Japanese encephalitis virus, tick borne encephalitis virus, Kunjin virus, Murray Valley encephalitis virus, St Louis encephalitis virus, Omsk Hemorrhagic Fever virus, bovine viral diarrhea virus, Zika virus, hepatitis virus. In an embodiment, the viral infection is hepatitis virus infection. In a further embodiment, the viral infection is hepatitis b or hepatitis c virus infection.

In another aspect, provided is a pharmaceutical composition, comprising a compound of formula (I) or a pharmaceutically acceptable salt in therapeutically effective amount and one or more pharmaceutically acceptable carriers or excipients. The pharmaceutical composition may further comprise one or more additional therapeutical agents.

The pharmaceutical composition according to the invention may be prepared by combining the compound according to the invention or the salt thereof with a pharmaceutically acceptable carrier. For example, it may be formulated into solid, semi-solid, liquid or gas formulation, such as tablet, pill, capsule, powder, granule, ointment, emulsion, suspension, solution, suppository, injection, inhalant, gel, microsphere, aerosol or the like.

Typical routes for administering the compound according to the invention or the pharmaceutically acceptable salt thereof or the stereoisomer thereof or the pharmaceutical composition thereof comprise but not limited to oral, rectal, transmucosal, enteral administration or local, transcutaneous, inhalant, parenteral, sublingual, intravaginal, intranasal, intraocular, intraperitoneal, intramuscular, subcutaneous, intravenous administration.

The pharmaceutical composition according to the invention may be prepared by the processes well-known in the art, such as conventional mixing, dissolution, granulation, dragee coating, levigation, emulsion, freeze-drying or the like.

As for oral administration, the active compounds may be mixed with the pharmaceutically acceptable carriers well-known in the art to prepare the pharmaceutical composition. The carriers may be used to prepare the compounds according to the invention into tablet, pill, troche, dragee, capsule, liquid, gel, slurry, suspension or the like useful for oral administration to the patient.

Solid oral composition may be prepared by conventional mixing, filling or compressing processes, for example, by the following processes: mixing the active compounds with solid excipients, optionally milling the resultant mixture, adding other proper adjuvants if necessary, and then processing the mixture into granules so as to obtain the core of tablet or dragee. The proper adjuvants comprise but not limited to binder, diluent, disintegrant, lubricant, glidant, sweetener, corrigent or the like. Additional examples comprise microcrystalline cellulose, glucose solution, acacia gel, gelatine solution, sucrose and starch paste; talcum, starch, magnesium stearate, calcium stearate or stearic acid; lactose, sucrose, starch, mannitol, sorbitol or dicalcium phosphate; silicon dioxide; croscarmellose sodium, pregelatinized starch, sodium starch glycolate, alginic acid, maize starch, potato starch, methylcellulose, agar, carboxymethyl cellulose, crosslinked polyvinylpyrrolidone or the like. The core of dragee may be optionally coated through well-known processes, especially by an enteric coating.

The pharmaceutical composition may be useful for parenteral administration, for example as appropriate unit dosage form like sterile solution, suspension or freeze dried product. Proper excipients may be used, such as filler, buffer or surfactant.

The compound of formula (I) or the pharmaceutically acceptable salt thereof described herein may be administered by any suitable route and process, for example by oral or parenteral administration (e.g. intravenous administration). The effective amount of the compound of formula (I) may range from about 0.0001 to 20 mg/Kg bodyweight/day, for example, 0.001 to 10 mg/Kg bodyweight/day.

The frequency of the compound of formula (I) depends on requirements of the individual patient, for example one or two or more times per day. Administration may be intermittent, for example, during the period of several days, the patient receives the daily dosage of the compound of formula (I), and then during the period of several days or a longer time, the patient does not receive the daily dosage of the compound of formula (I).

Definition

Unless stated otherwise, the terms and phrases used herein have the following meaning. A specific term or phrase shall not be considered as unclear or indefinite when it is not specifically defined. It should be understood according to the general meaning. The trade name used herein refers to the corresponding product or the active ingredient.

The term "optional" or "optionally" means the event described subsequent thereto may or may not happen. This term encompasses the cases that the event may or may not happen. For example, the expression that ethyl is "optionally" substituted by halogen means the ethyl is unsubstituted ($CH_2CH_3$), mono-substituted (e.g. $CH_2CH_2F$), poly-substituted (e.g. $CHFCH_2F$, $CH_2CHF_2$ or the like) or completely substituted ($CF_2CF_3$). A person skilled in the art will know that with respect to any group containing one or more substitutes, a substitution or substitution mode which cannot exist and/or cannot be synthesized will not be introduced.

The expression $C_{m-n}$ used herein means that it has m-n carbon atoms. For example, "$C_{3-10}$ cycloalkyl" means said cycloalkyl has 3-10 carbon atoms. "$C_{0-6}$ alkylene" means said alkylene has 0-6 carbon atoms, wherein the alkylene is a bond when it has 0 carbon atom.

The numerical range herein refers to each of the integers therein. For example, "$C_{1-10}$" means said group may have 1 carbon atom, 2 carbon atoms, 3 carbon atoms, 4 carbon atoms, 5 carbon atoms, 6 carbon atoms, 7 carbon atoms, 8 carbon atoms, 9 carbon atoms or 10 carbon atoms.

The term "substituted" means that one or more hydrogen atoms on a given atom are replaced by a substituent, provided that the valence of the particular atom is normal and the compound after substitution is stable. When the substituent is a ketone group (i.e. =O), two hydrogen atoms are replaced, and the ketone substitution will not occur at an aromatic group.

When any variable (e.g. R) occurs at the composition or structure over one time, it is defined independently at each case. Therefore, for example, if a group is substituted by 0-2 R, the group may be optionally substituted by at most two R and R has independent option at each case. Additionally, a combination of substituents and/or the variants thereof are allowed only if such a combination will result in a stable compound.

Unless stated otherwise, the term "hetero" means heteroatom or heteroatom radical (i.e. a radical containing heteroatom), i.e. the atoms beyond carbon and hydrogen atoms or the radical containing such atoms, wherein the heteroatom is independently selected from the group consisting O, N, S, P, Si, Ge, Al and B. In an embodiment wherein two or more heteroatoms are involved, the two or more heteroatoms may be the same or part or all of the two or more heteroatoms may be different.

The term "halo" or "halogen" refers to F, Cl, Br and I.
The term "hydroxyl" refers to —OH group.
The term "cyano" refers to —CN group.
The term "thiol" refers to —SH group.
The term "amino" refers to —NH$_2$ group.
The term "alkyl" refers to a linear or branched saturated aliphatic hydrocarbyl group consisting of carbon and hydrogen atoms, which is linked to rest of the molecule via a single bond. Non-limiting examples of alkyl comprise but not limited to methyl, ethyl, propyl, 2-propyl, n-butyl, isobutyl, t-butyl, n-pentyl, 2-methylbutyl, neopentyl, n-hexyl, 2-methylhexyl, —CH$_2$-cyclopropyl or the like.

The term "alkylene" refers to a linear, branched or cyclic saturated hydrocarbyl group, which has a residue group derived from removal of two hydrogen atoms from the same carbon atom or two different carbon atoms of the parent alkyl. Non-limiting examples of alkylene comprise but not limited to methylene (—CH$_2$—), 1,1-ethylene (—CH(CH$_3$)—), 1,2-ethylene (—CH$_2$CH$_2$—), 1,1-propylene (—CH(CH$_2$CH$_3$)—), 1,2-propylene (—CH$_2$CH(CH$_3$)—), 1,3-propylene (—CH$_2$CH$_2$CH$_2$—), 1,4-butylene (—CH$_2$CH$_2$CH$_2$CH$_2$—) or the like.

The term "imino" refers to —NH—.
The term "alkenyl" refers to a linear or branched unsaturated aliphatic hydrocarbyl group consisting of carbon and hydrogen atoms, which has at least one double bond. Non-limiting examples of alkenyl comprise but not limited to vinyl, 1-propenyl, 2-propenyl, 1-butenyl, isobutenyl, 1,3-butadienyl or the like.

The term "alkynyl" refers to a linear or branched unsaturated aliphatic hydrocarbyl group consisting of carbon and hydrogen atoms, which has at least one triple bond. Non-limiting examples of alkynyl comprise but not limited to ethynyl (—C≡CH), 1-propynyl (—C≡C—CH$_3$), 2-propynyl (—CH$_2$—C≡CH), 1,3-butadiynyl (—C≡C—C≡CH) or the like.

The term "cyclohydrocarbyl" refers to a saturated or unsaturated non-aromatic cyclic hydrocarbyl group consisting of carbon and hydrogen atoms, which preferably contains one or two rings. The cyclohydrocarbyl may has a monocyclic, fused polycyclic, bridge cyclic or spirocyclic structure. Non-limiting examples of cyclohydrocarbyl comprise but not limited to cyclopropyl, cyclobutyl, cyclopentyl, cyclohexyl, cycloheptyl, bicyclo[2.2.1]heptyl, spiro[3.3]heptyl or the like.

The term "heterocyclohydrocarbyl" refers to a non-aromatic monocyclic, fused polycyclic, bridge cyclic or spirocyclic system group, wherein part of the ring atoms are heteroatoms selected from the group consisting of N, O, S(O)$_n$ (wherein n is 0, 1 or 2), and rest of the ring atoms are C. Such ring may be saturated or unsaturated (for example, has one or more double bonds but does not have a complete conjugated π-electron system. Examples of 3 membered heterocyclohydrocarbyl comprise but not limited to oxiranyl, thiiranyl, aziranyl. Examples of 4 membered heterocyclohydrocarbyl comprise but not limited to azetidinyl, oxetanyl, thietanyl. Examples of 5 membered heterocyclohydrocarbyl comprise but not limited to tetrahydrofuranyl, tetrahydrothiophenyl, pyrrolidinyl, isoxazolidinyl, oxazolidinyl, isothiazolidinyl, 1,1-dioxoisothiazolidinyl, thiazolidinyl, imidazolidinyl, tetrahydropyrazolyl, pyrrolinyl, dihydrofuranyl, dihydrothiophenyl. Examples of 6 membered heterocyclohydrocarbyl comprise but not limited to piperidinyl, tetrahydropyranyl, tetrahydrothiopyranyl, morpholinyl, piperazinyl, 1,4-thioxanyl, 1,4-dioxanyl, thiomorpholinyl, 1,2-/1,4-dithianyl, dihydropyridyl, tetrahydropyridyl, dihydropyranyl, tetrahydropyranyl, dihydrothiopyranyl. Examples of 7 membered heterocyclohydrocarbyl comprise but not limited to azacycloheptanyl, oxacycloheptanyl, thiepanyl, oxaazabicyclo[2.2.1]heptyl, azaspiro[3.3]heptyl or the like.

The term "aryl" refers to monocyclic or fused polycyclic aromatic cyclic group which has conjugated it electronic system and all the ring atoms are carbon. For example, aryl may have 6-20 carbon atoms, 6-14 carbon atoms or 6-12 carbon atoms. Non-limiting examples of aryl comprise but not limited to phenyl, naphthyl, anthryl or the like.

The term "heteroaryl" refers to monocyclic or fused polycyclic system containing at least one ring atom selected from the group consisting of N, O and S with other ring atoms being C and containing at least one aromatic ring. Non-limiting examples of heteroaryl comprise but not limited to pyrrolyl, furyl, thienyl, imidazolyl, oxazolyl, pyrazolyl, pyridyl, pyrimidinyl, pyrazinyl, quinolinyl, isoquinolinyl, tetrazolyl, triazolyl, triazinyl, benzofuranyl, benzothienyl, indolyl, isoindolyl or the like.

The term "pharmaceutically acceptable" refers to the compound, material, composition and/or dosage form, which are within the scope of reliable medical judgment, suitable for contact with human and animal tissues, without over toxicity, irritation, allergic reaction or other problems or complications and has acceptable benefit/risk ratio.

As pharmaceutically acceptable salt, for example, the following examples may be mentioned: metal salts, ammonium salts, salts formed with organic bases, inorganic acids, organic salts, basic or acidic amino acids or the like. Non-limiting examples of metal salts comprise but not limited to salts of alkaline metals, for example sodium salt, potassium salt or the like; salts of alkaline earth metals, for example calcium salt, magnesium salt, barium salt or the like; aluminum salt or the like. Non-limiting examples of the salts formed with organic bases comprise but not limited to those formed with trimethylamine, triethylamine, pyridine, methylpyridine, 2,6-dimethylpyridine, ethanolamine, diethanolamine, triethanolamine, cyclohexylamine, dicyclohexylamine or the like. Non-limiting examples of the salts formed with inorganic acids comprise but not limited to those formed with hydrochloric acid, hydrobromic acid, nitric acid, sulphuric acid, phosphoric acid or the like. Non-limiting examples of the salts formed with organic acids comprise but not limited to those formed with formic acid, acetic acid, trifluoroacetic acid, fumaric acid, oxalic acid, malic acid, maleic acid, tartaric acid, citric acid, succinic acid, methanesulfonic acid, benzene sulfonic acid, p-toluenesulfonic acid or the like. Non-limiting examples of the salts formed with basic amino acids comprise but not limited to those formed with arginine, lysine, ornithine or the like. Non-limiting examples of the salts formed with acidic amino acids comprise but not limited to those formed with aspartic acid, glutamic acid or the like.

The pharmaceutically acceptable salts according to the invention may be prepared from the parent compound containing acidic or basic group through conventional chemical procedures. Generally, such salts may be prepared through the reaction of the compounds in the form of free acid or base with stoichiometric appropriate base or acid in water, organic solvent or the mixture thereof. Typically, nonaqueous medium like ether, ethyl acetate, ethanol, isopropanol, acetonitrile etc. are preferable.

Some compounds according to the invention may exist in unsolvated or solvated forms, including hydrate form. In general, the solvated forms are equivalent to unsolvated forms and both of them are encompassed within the scope of the invention. Some compounds according to the invention may exist in polymorphic or amorphous forms.

Some compounds according to the invention may have asymmetric carbon atom (optical center) or double bond. Racemate, diastereomer, geometric isomer and individual isomer are encompassed within the scope of the invention.

The graphic representations of racemic, ambiscalemic and scalemic or enantiomerically pure compounds used herein are taken from Maehr, J. Chem. Ed. 1985, 62: 114-120. Unless stated otherwise, solid and broken wedges are used to denote the absolute configuration of a stereocenter. When the compound according to the invention contains ethylenical double bond(s) or other geometric asymmetry center(s), unless stated otherwise, E and Z geometric isomer are encompassed. Likewise, all the tautomeric forms are encompassed with the scope of the invention.

The compound according to the invention may have special geometric isomer or stereoisomer form. Such compounds are encompassed by the invention, including cis and trans isomers, (−)- and (+)-enantiomers, (R)- and (S)-enantiomers, diastereomer, (D)-isomer, (L)-isomer, and racemic mixture or other mixture thereof, such as the mixture enriched in enantiomer or diastereomer, and all the mixtures are encompassed within the scope of the invention. The substituent like alkyl may have other asymmetric carbon atom. All the isomers and the mixture thereof are encompassed within the scope of the invention.

Optical (R)- and (S)-isomers as well as D and L isomers may be prepared through chiral synthesis or chiral agent or other conventional technology. An enantiomer of the compound according to the invention may be prepared through asymmetric synthesis or derivatization with chiral auxiliary, wherein the resultant diastereomer mixture is separated and the desired pure enantiomer is obtained by cleavage of the auxiliary group. Alternatively, when there is basic functional group (e.g. amino) or acidic functional group (e.g. carboxyl) in the molecule, the diastereomeric salt may be formed with appropriate optical acid or base and then the diastereomeric resolution is performed with fractional crystallization or chromatography which is well-known in the art so as to recover the pure enantiomer. Additionally, separation of enantiomer from diastereomer is generally performed with chromatography, which uses chiral stationary phase and is optionally combined with chemical derivatization (for example, carbamate formed from amine).

The compound according to the invention may contain atomic isotope in non-natural ratio at one or more atoms constituting said compound. For example, the compound may be labeled with radioisotope, such as Tritium ($^3H$), Iodine-125 ($^{125}I$) or C-14 ($^{14}C$). Alternation of all the radioisotopes of the compound, either radioactive or not, is encompassed within the scope of the invention.

The term "pharmaceutically acceptable carrier" refers to those carriers which have no significant irritation and do not impair the bioactivity and property of the active compound. The "pharmaceutically acceptable carrier" refers to inert substance which is administered with active ingredient and is beneficial to the administration thereof, and comprises but not limited to any of the following substances approved by State Food and Drug Administration for use in human or animal (e.g. livestock): glidant, sweetening agent, diluent, preservative, dye/colorant, flavoring agent, surfactant, wetting agent, dispersant, disintegrant, suspending agent, stabilizing agent, isotonic agent, solvent or emulsifying agent. Non-limiting examples of the carriers comprise calcium carbonate, calcium phosphate, various sugars and starches, cellulose derivative, gelatine, vegetable oil and polyethylene glycol or the like. Other information regarding the carriers may be found in Remington: The Science and Practice of Pharmacy, 21st Ed., Lippincott, Williams & Wilkins (2005), of which the contents are incorporated herein by reference.

The term "excipient" generally refers to the carrier, diluent and/or medium used to formulate effective pharmaceutical composition.

As for pharmaceutical or pharmacological active agent, the term "effective amount" or "therapeutically effective amount" refers to the amount of the medicament or agent which is not toxic but sufficient to achieve the desired effect. With respect to the oral formulation herein, the "effective amount" for an active substance in the composition refers to the amount required to achieve the desired effect in combination with another active substance in the composition. The effective amount may be determined individually and depends on the age and general condition of the receptor as well as specific active substance. The effective amount in specific case can be determined by a person skilled in the art through conventional test.

The term "active ingredient", "therapeutic agent", "active substance" or "active agent" refers to a chemical entity useful for treating target disorder, disease or condition effectively.

The compound according to the invention can be prepared through various synthesis processes well-known to a person skilled in the art, including the specific embodiments illustrated below, the embodiments through combination of such specific embodiments with other chemical synthesis processes as well as equivalents well-known to a person skilled in the art. The preferable embodiments comprise but not limited to the working Examples herein.

The chemical reaction of the specific embodiment according to the invention is performed in appropriate solvent which should be suitable for the chemical change and required reagent and material according to the invention. To obtain the compound according to the invention, a person skilled in the art sometimes needs to perform modification or selection to synthesis step or reaction procedure based on the known embodiments.

One important factor in designing any synthesis scheme in the art lies in selecting an appropriate protective group for reactive group (e.g. amino in the invention). A person skilled in the art may refer to Protective Groups In Organic Synthesis, Wiley and Sons, 1991 by Greene and Wuts. The above cited references above are incorporated herein by reference in entirety.

The compound of general formula (II) may be prepared by a person skilled in the field of organic synthesis with standard procedures according to the following scheme 1:

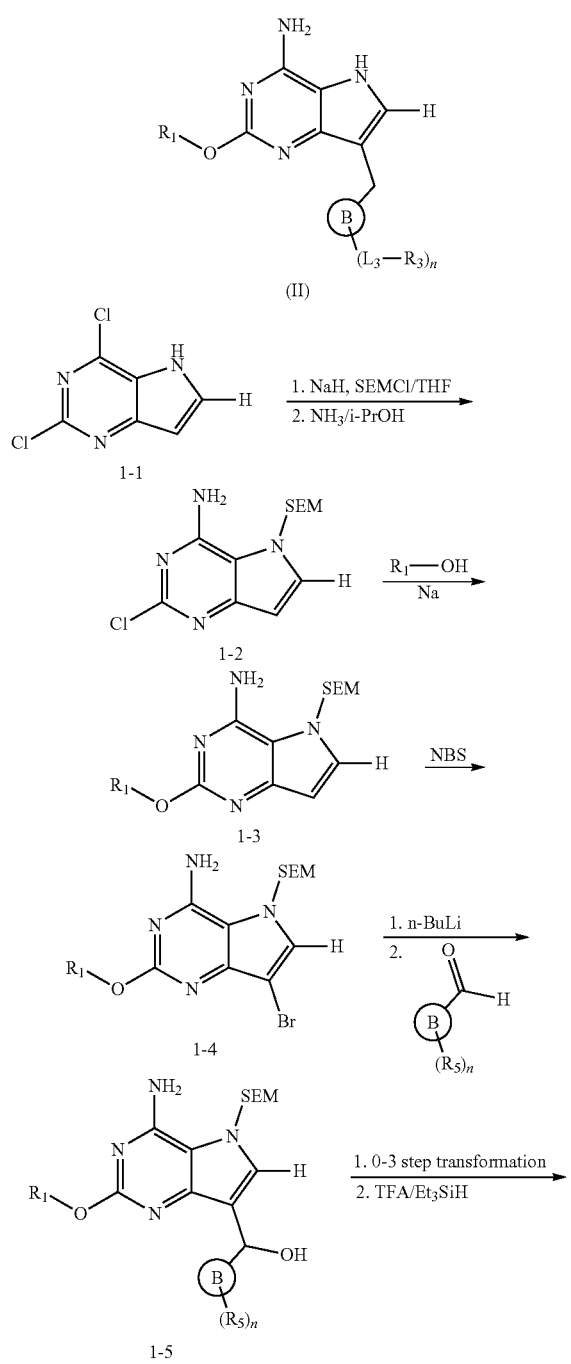

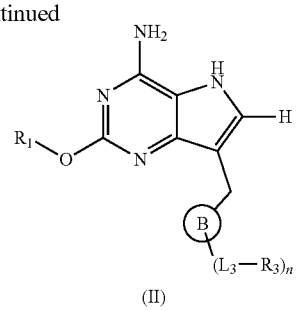

General Scheme 1

Starting from 2,4-dichloro-5H-pyrrolo[3,2-d]pyrimidine (1-1) (commercial reagent), SEM protection and then substitution with $NH_3$ are performed to give 2-chloro-5-((2-(trimethylsilyl)ethoxy)methyl)-5H-pyrrolo[3,2-d]pyrimidine-4-amine (1-2). Various alcohols (general formula $R_1OH$) like n-butanol are used to form sodium alkoxide in the presence of sodium, which is then substituted to give intermediate (1-3). The intermediate is reacted with NBS to give bromide (1-4). The bromide (1-4) under the action of n-butyllithium is converted into lithium salt with the exchange of Br. The lithium salt is reacted with aldehyde ($R_5$ is selected from the group consisting of formaldehyde group or $L_3$-$R_3$ with an optional protective group) to give secondary alcohol (1-5). The secondary alcohol (1-5) is subject to 0-3 step transformation, reduction with trifluoroacetic acid, triethylsilane and deprotection to give final product (II).

The compound of general formula (III) according to the invention may be prepared via the following scheme 2 according to standard procedures by a person skilled in field of organic synthesis.

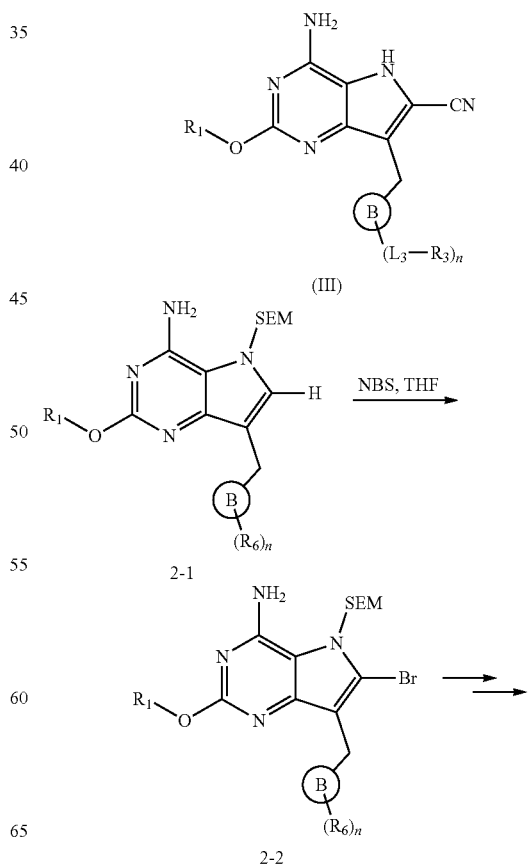

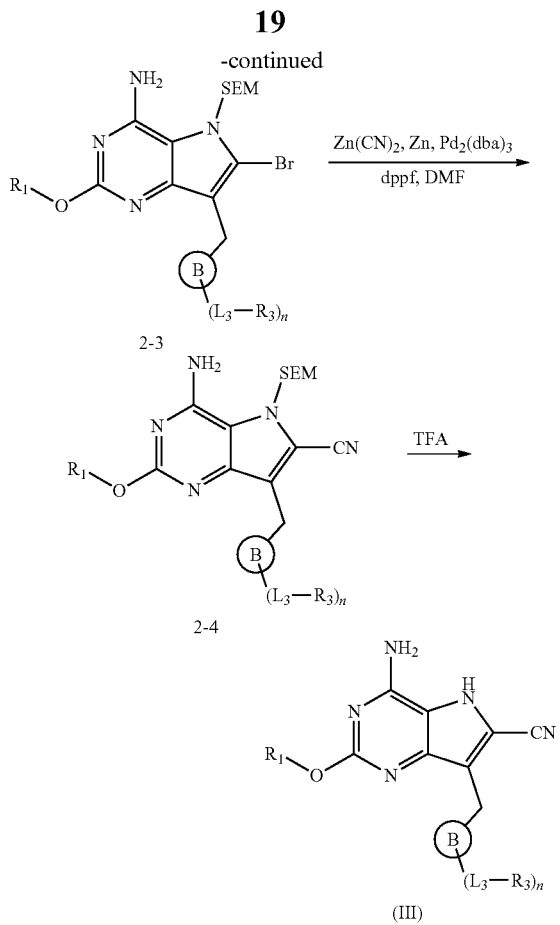

General Scheme 2

Starting from intermediate (2-1) ($R_6$ is selected from the group consisting of carboxylate methyl ester), the bromide (2-2) is obtained through reaction with NBS. The bromide (2-2) is further subjected to 1-3 step reaction (such as reduction to aldehyde with DIBAL-H, followed by amination with pyrrole in methanol solvent via $NaBH_3CN$ reduction) to give another bromide (2-3). The bromide (2-3) is transferred to 2-cyano compound (2-4) under the condition of $Zn(CN)_2/Zn/Pd_2$ $(dba)_3$/dppf/DMF. SEM is removed with trifluoroacetic acid to give the final product (III).

A person skilled in the art will know, to prepare the compound according to the invention, the order of the steps in schemes 1 and 2 may be different, which are also within the scope of the invention.

The Examples are used to illustrate the invention and should not be considered as limitation thereto.

The solvents used herein are commercially available and can be used without further purification. The reactions are generally performed under inert atmosphere in anhydrous solvent. Data of proton magnetic resonance is recoded in Bruker Avance III 400 (400 MHz) spectrometer, with the chemical shift shown as (ppm) at tetramethylsilane low field. Mass spectrometry is determined on Agilent 1200 plus 6110 (&1956A). LC/MS or Shimadzu MS includes a DAD: SPD-M20A(LC) and Shimadzu Micromass 2020 detector. Mass spectrometer is equipped with an electrospray ionization (ESI) operated at positive or negative mode.

The following abbreviations are used herein: aq: aqueous; SEMCl: (2-(chloromethoxyl)ethyl)trimethylsilane; eq: equivalent; 1,3-DPPP: 1,3-bis(diphenylphosphino)propane; DCM: dichloromethane; PE: petroleum ether; DMF: N,N-dimethylformamide; NMP: N-methylpyrrolidinone; EtOAc: ethyl acetate; i-PrOH: isopropanol; EtOH: ethanol; MeOH: methanol; THF: tetrahydrofuran; BPO: benzoyl peroxide; BOC: t-butyloxy carbonyl; HOAc: acetic acid; $NaCNBH_3$: sodium cyanoborohydride; LAH: lithium aluminium hydride; 9-BBN: 9-borabicyclononane; MSCl: methanesulfonyl chloride; RT: room temperature; O/N: overnight; $Boc_2O$: di-tert-butyl dicarbonate; TFA: trifluoroacetic acid; TFAA: trifluoroacetic acid anhydride; TEA: triethylamine; DIBAL-H: diisobutyl aluminium hydride; NBS: bromosuccinimide; DPPF: 1,1'-bis(diphenylphosphino)ferrocene; $Ph_3P$: triphenylphosphine; $Pd(OAc)_2$: palladium acetate; $Pd(PPh_3P)_2CL_2$: bis(triphenylphosphine)palladium chloride; $Pd_2$ $(dba)_3$: tris(benzylideneacetone)dipalladium; XANTPHOS: 4,5-bis(diphenylphosphino)-9,9-dimethylxanthene; n-BuLi: n-butyllithium.

The compounds are nominated manually or by the ChemDraw® software. The names of commercially available compounds provided in the catalog of the supplier are used.

High performance liquid chromatographic analysis is performed with Shimadzu LC20AB system equipped with Shimadzu SIL-20A auto-sampler and Japanese Shimadzu DAD: SPD-M20A detector on Xtimate C18 (3 m filler, 2.1×300 mm) chromatographic column. 0-60AB_6 min method: linear gradient is applied, wherein elution is initiated with 100% A (A is 0.0675% TFA aqueous solution) and terminated with 60% B (B is 0.0625% TFA in MeCN) (the whole process is 4.2 min), and then 60% B is used for elution for 1 min. The chromatographic column is further equilibrated for 0.8 min to reach 100:0 and the total operational time is 6 min. 10-80AB_6 method: linear gradient is applied, wherein elution is initiated with 90% A (A is 0.0675% TFA aqueous solution) and terminated with 80% B (B is 0.0625% TFA in acetonitrile) (the whole process is 4.2 min) and then 80% B is used for elution for 1 min. The chromatographic column is further equilibrated for 0.8 min to reach 90:10 and the total operational time is 6 min. The column temperature is 50° C. and velocity is 0.8 mL/min. The scanning wave of diode array detector is 200-400 nm.

Thin layer chromatographic (TLC) analysis is performed on silica gel GF254 of Sanpont-group. Speckles are detected with UV light and in some cases other processes may also be used. In these cases, the thin layer is spread with iodine (about 1 g iodine is added into 10 g silica gel with complete mixing), vanillin aldehyde (about 1 g vanillin aldehyde is dissolved in 100 mL 10% $H_2SO_4$), ninhydrin (available from Aldrich) or particular developer (($NH_4)_6Mo_7O_{24}.4H_2O$, 5 g $(NH_4)_2Ce(IV)(NO_3)_6$, 450 mL $H_2O$ and 50 mL concentrated $H_2SO_4$ are completely mixed) and the compound is detected. With a process similar as that described in Still, W. C.; Kahn, M.; and Mitra, M. Journal of Organic Chemistry, 1978, 43, 2923-2925, the flash column chromatography is performed on 40-63 μm (230-400#) silica gel from Silicycle. Common solvents in flash column chromatography or thin layer chromatography comprise dichloromethane/methanol, ethyl acetate/methanol and hexan/ethyl acetate mixture.

Preparative chromatographic analysis is performed on Gilson-281 Prep LC 322 system with Gilson UV/VIS-156 detector and the chromatographic column is Agella Venusil ASB Prep C18, 5 m, 150×21.2 mm; Phenomenex Gemini C18, 5 m, 150×30 mm; Boston Symmetrix C18, 5 m, 150×30 mm; or Phenomenex Synergi C18, 4 m, 150×30 mm. Low gradient acetonitrile/water is used to elute the compound when the velocity is about 25 mL/min, wherein the water contains 0.05% HCl, 0.25% HCOOH or 0.5% NH₃.H₂O, and the total operational time is 8-15 min.

EXAMPLES

Figure 1:
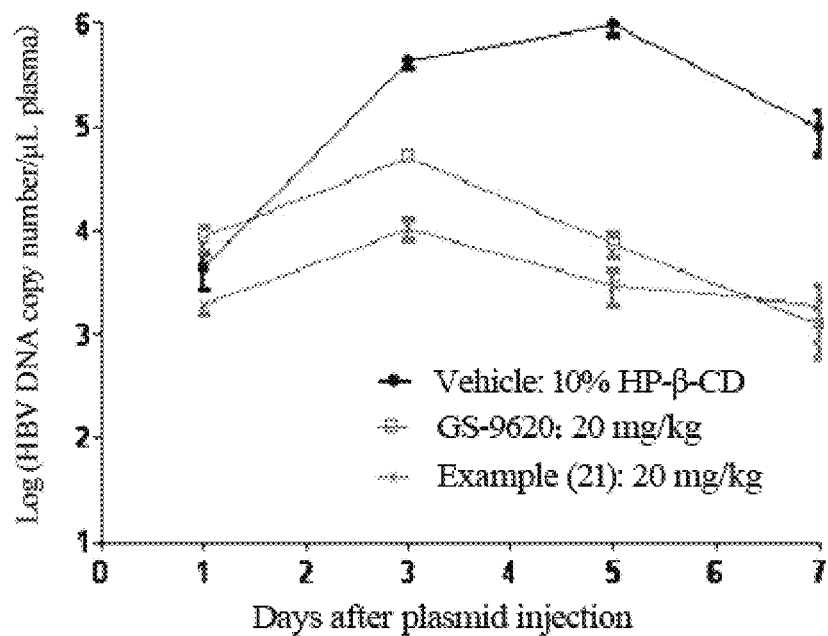
FIG. 1: in vivo pharmacodynamics in HDI mouse model infected with hepatitis b virus (plasma).

The following Examples are intended to illustrate the invention and should not be understood as a limitation to the scope thereof.

Example 1

2-butoxy-7-(3-((4-methylpiperazine-1-yl)methyl) benzyl)-5H-pyrrolo[3,2-d]pyrimidine-4-amine

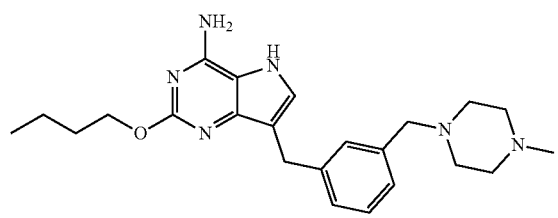

Scheme:

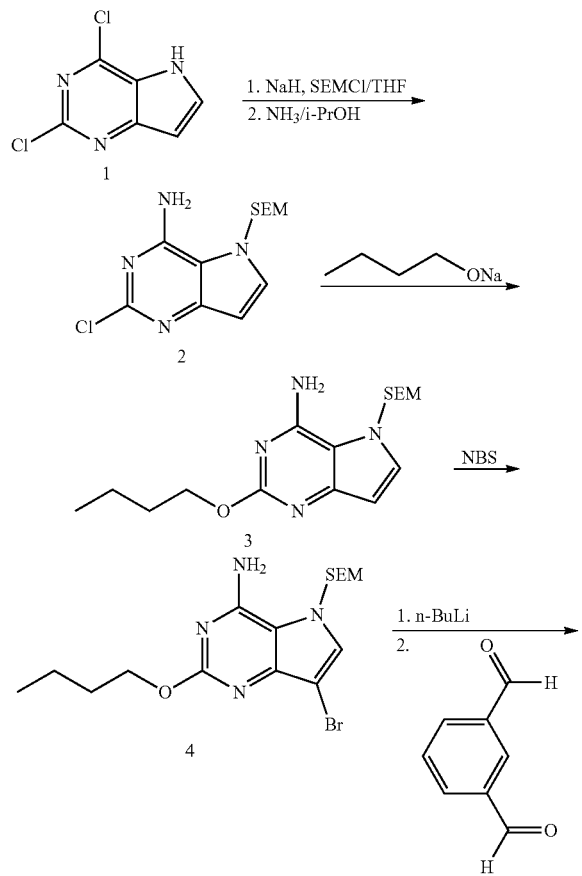

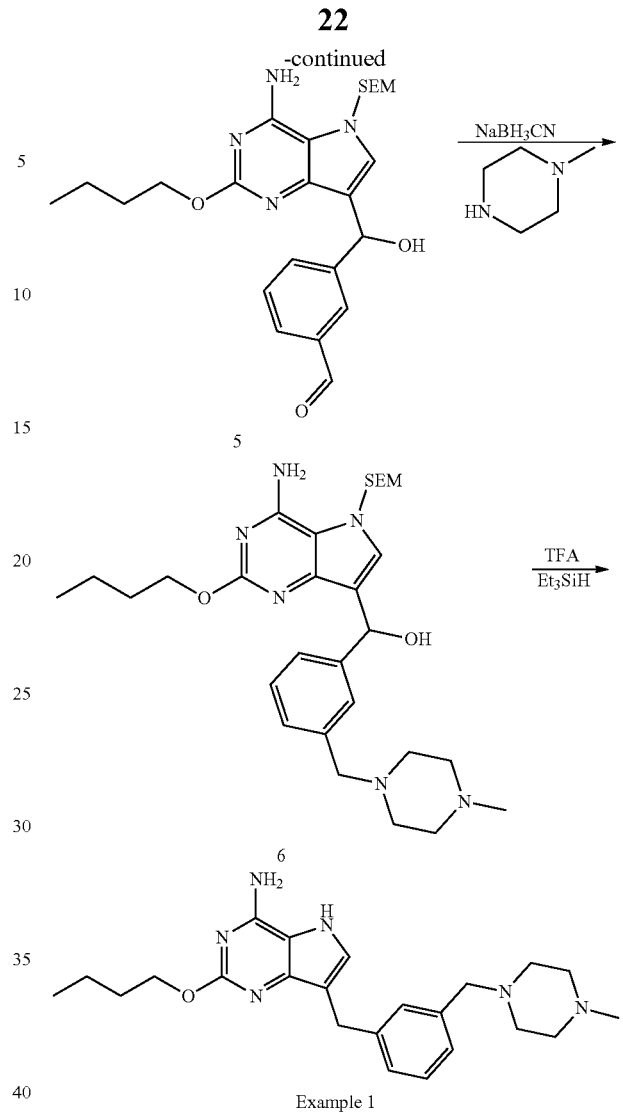

Example 1

Example 1 Procedures

Step A: 2,4-dichloro-5H-pyrrolo[3,2-d]pyrimidine (4 g, 21.4 mmol) was dissolved in anhydrous tetrahydrofuran (30 mL), to which was added sodium hydride (1.03 g, 60% mineral oil mixture, 25.6 mmol) in portions at 0° C. The reaction liquid was stirred at room temperature for 30 min and (2-(chloromethoxyl)ethyl)trimethylsilane (3.9 g, 23.5 mmol) was added dropwise. The mixture was further stirred at room temperature for 2 h and was diluted with water (120 mL) and extracted with ethyl acetate (100 mL×2). The combined organic layer was washed with saturated aqueous sodium carbonate solution and saline, dried with anhydrous sodium sulfate, and concentrated under reduced pressure. The residue was purified with silica gel column chromatography (eluent: ethyl acetate/petroleum ether 5% to 10%) to give 2,4-dichloro-5-((2-(trimethylsilyl)ethoxyl)methyl)-5H-pyrrolo[3,2-d]pyrimidine (5.8 g, 85%) as yellow solid.

MS(ESI) M/Z: 318 [M+H⁺].

Step B: In 1000 mL high pressure reactor, 2,4-dichloro-5-((2-(trimethylsilyl)ethoxyl)methyl)-5H-pyrrolo[3,2-d]pyrimidine (5 g, 15.8 mmol), isopropanol (15 mL) and aqueous ammonia (250 mL) were mixed and the mixture was stirred at 100-110° C. for 3 h. After the mixture was cooled to room temperature, it was diluted with water (250 mL) and filtered to give 2-chloro-5-((2-(trimethylsilyl)ethoxyl)methyl)-5H-pyrrolo[3,2-d]pyrimidine-4-amine (4 g, 85%), which was not further purified.

MS(ESI) M/Z: 299[M+H$^+$].

Step C: 2-chloro-5-((2-(trimethylsilyl)ethoxyl)methyl)-5H-pyrrolo[3,2-d]pyrimidine-4-amine (4 g, 13.4 mmol) and sodium butoxide (5.15 g, 53.6 mmol) were dissolved in n-butanol (55 mL). The mixture was heated to 100° C. under nitrogen atmosphere and stirred for 8 h. After the mixture was cooled to room temperature, it was diluted with water (200 mL), extracted with ethyl acetate (100 mL×3). The combined organic layer was washed with saline, dried with anhydrous sodium sulfate, and concentrated under reduced pressure. The residue was purified with silica gel column chromatography (eluent: ethyl acetate/petroleum ether 15% to 25%) to give 2-butoxy-5-((2-(trimethylsilyl)ethoxyl)methyl)-5H-pyrrolo[3,2-d]pyrimidine-4-amine (4.1 g, 91%) as yellow solid.

MS(ESI) M/Z: 337 [M+H$^+$].

Step D: 2-butoxy-5-((2-(trimethylsilyl)ethoxyl)methyl)-5H-pyrrolo[3,2-d]pyrimidine-4-amine (4 g, 12 mmol) was dissolved in anhydrous tetrahydrofuran (40 mL). NBS (2.2 g, 12.5 mmol) was formulated as saturated solution in anhydrous tetrahydrofuran, which was added into the above solution over 20 min at a temperature below 0° C. After addition, the reaction mixture was stirred for 30 min at 0° C., and diluted with saline (150 mL), and extracted with ethyl acetate (100 mL×3). The combined organic layer was dried with anhydrous sodium sulfate and concentrated under reduced pressure. The residue was purified with silica gel column chromatography (eluent: ethyl acetate/petroleum ether 5% to 15%) to give 7-bromo-2-butoxy-5-(2-(trimethylsilyl)ethoxyl)methyl)-5H-pyrrolo[3,2-d]pyrimidine-4-amine (3.85 g, 78%) as white solid.

MS(ESI) M/Z: 415, 417[M+H$^+$].

Step E: At −78° C., n-butyllithium (2.5 M, 12 mL, 30 mmol) was added into a solution of 7-bromo-2-butoxy-5-((2-(trimethylsilyl)ethoxyl)methyl)-5H-pyrrolo[3,2-d]pyrimidine-4-amine (3 g, 7.25 mmol) in anhydrous tetrahydrofuran (40 mL) under nitrogen atmosphere with stirring. The reaction mixture was stirred at −78° C. for 1 h and then a solution of 1,3-benzenedialdehyde (1.26 g, 9 mmol) in anhydrous tetrahydrofuran (5 mL) was added slowly. The mixture was further stirred for 30 min at −78° C., then poured into saturated ammonium chloride aqueous solution (15 mL) and was extracted with ethyl acetate (60 mL×2). The combined organic layer was concentrated under reduced pressure and the residue was purified with preparative HPLC to give 1.1 g of 3-((4-amino-2-butoxy-5-((2-(trimethylsilyl)ethoxyl)methyl)-5H-pyrrolo[3,2-d]pyrimidine-7-yl) (hydroxyl) methyl)benzaldehyde salt.

MS(ESI) M/Z: 471[M+H$^+$].

Step F: At 0° C., to a solution of 3-((4-amino-2-butoxy-5-((2-(trimethylsilyl)ethoxyl)methyl)-5H-pyrrolo[3,2-d]pyrimidine-7-yl) (hydroxyl) methyl)benzaldehyde (200 mg, 0.43 mmol) and 1-methylpiperazine (87 mg, 0.87 mmol) in ethanol (2.5 mL) was added sodium cyanoborohydride (40 mg, 0.64 mmol) in portions with stirring. The reaction mixture was stirred at room temperature for 2 h, diluted with water (10 ml) and extracted with ethyl acetate (15 mL×2). The combined organic layer was dried with anhydrous sodium sulfate and concentrated under reduced pressure to give crude (4-amino-2-butoxy-5-((2-(trimethylsilyl)ethoxyl)methyl)-5H-pyrrolo[3,2-d]pyrimidine-7-yl)(3-((4-methyl-piperazine-1-yl)methyl)phenyl)methanol, which was used for the next step directly.

MS(ESI) M/Z: 555[M+H$^+$].

Step G: To a solution of (4-amino-2-butoxy-5-((2-(trimethylsilyl)ethoxyl)methyl)-5H-pyrrolo[3,2-d]pyrimidine-7-yl)(3-((4-methylpiperazine-1-yl)methyl)phenyl)methanol (100 mg) in trifluoroacetic acid (2 mL) was added triethylsilane (0.4 mL) in portions with stirring. The reaction mixture was stirred at 55° C. for 1 h under nitrogen atmosphere and concentrated under reduced pressure. The residue was dissolved in an anhydrous solution of potassium carbonate (100 mg) in methanol (5 mL). The mixture was further stirred at 50° C. for 30 min and filtered. The filtrate was concentrated under reduced pressure and the residue was purified with preparative HPLC to give 36 mg of 2-butoxy-7-(3-((4-methylpiperazine-1-yl)methyl)benzyl)-5H-pyrrolo[3,2-d]pyrimidine-4-amine trifluoroacetate.

$^1$HNMR (Methanol-d4, 400 MHz): δ 7.33-7.21 (m, 4H), 4.55 (t, J=6.8 Hz, 2H), 4.01 (s, 2H), 3.67 (s, 2H), 3.29-3.24 (m, 4H), 2.87-2.80 (m, 7H), 1.87-1.80 (m, 2H), 1.56-1.49 (m, 2H), 1.02 (t, J=6.8 Hz, 3H).

MS(ESI) m/z: 409[M+H$^+$].

Example 2

2-butoxy-7-(3-(morpholinomethyl)benzyl)-5H-pyrrolo[3,2-d]pyrimidine-4-amine

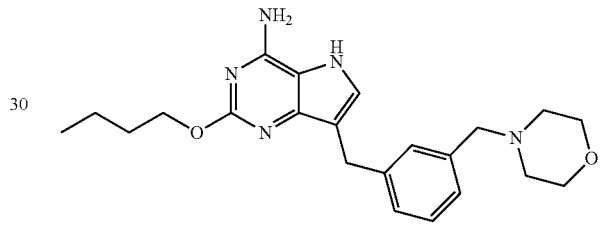

Step A: (4-amino-2-butoxy-5-((2-(trimethylsilyl)ethoxyl)methyl)-5H-pyrrolo[3,2-d]pyrimidine-7-yl)(3-(morpholinomethyl)phenyl)methanol was prepared according to Example 1, wherein morpholine was used instead of 1-methylpiperazine in Step F.

LCMS(ESI) m/z: 542[M+H$^+$].

Step B: 2-butoxy-7-(3-(morpholinomethyl)benzyl)-5H-pyrrolo[3,2-d]pyrimidine-4-amine formate was prepared with the procedures of Step G according to Example 1.

$^1$HNMR (Methanol-4, 400 MHz): δ 8.41 (s, 2H), 7.35-7.24 (m, 5H), 4.49 (t, J=6.8 Hz, 2H), 4.03 (s, 2H), 3.82 (s, 2H), 3.77-3.75 (m, 4H), 2.77-2.73 (m, 4H), 1.83-1.79 (m, 2H), 1.55-1.49 (m, 2H), 1.01 (t, J=6.8 Hz, 3H).

MS(ESI) m/z: 396[M+H$^+$].

Example 3

7-(3-(aminomethyl)benzyl)-2-butoxy-5H-pyrrolo[3,2-d]pyrimidine-4-amine

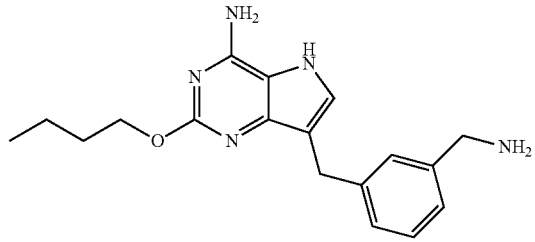 [SMILES: CCCCOc1nc(N)c2[nH]cc(Cc3cccc(CN)c3)c2n1]

Step A: (4-amino-2-butoxy-5-((2-(trimethylsilyl)ethoxyl)methyl)-5H-pyrrolo[3,2-d]pyrimidine-7-yl)(3-(aminomethyl)phenyl)methanol was prepared according to Example 1, wherein ammonium acetate was used instead of 1-methylpiperazine in Step F.

LCMS(ESI) m/z: 472[M+H⁺].

Step B: 7-(3-(aminomethyl)benzyl)-2-butoxy-5H-pyrrolo[3,2-d]pyrimidine-4-amine was prepared with the procedures of Step G according to Example 1.

¹HNMR (Methanol-4, 400 MHz): δ 7.31-7.15 (m, 4H), 7.06 (s, 1H), 4.32 (t, J=6.6 Hz, 2H), 4.00 (s, 2H), 3.80 (s, 2H), 1.79-1.73 (m, 2H), 1.56-1.50 (m, 2H), 1.01 (t, J=7.4 Hz, 3H).

MS(ESI) m/z: 326[M+H⁺].

Example 4

2-butoxy-7-(3-(pyrrolidine-1-ylmethyl)benzyl)-5H-pyrrolo[3,2-d]pyrimidine-4-amine

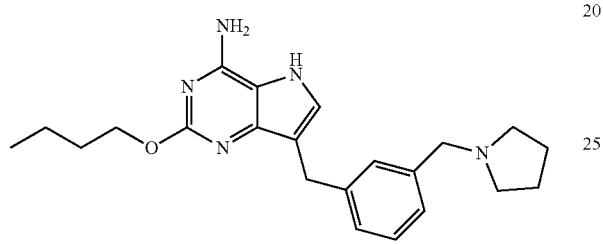

Step A: (4-amino-2-butoxy-5-((2-(trimethylsilyl)ethoxyl)methyl)-5H-pyrrolo[3,2-d]pyrimidine-7-yl) (3-(pyrrolidine-1-ylmethyl)phenyl)methanol was prepared according to Example 1, wherein pyrrolidine was used instead of 1-methylpiperazine in Step F.

Step B: 2-butoxy-7-(3-(pyrrolidine-1-ylmethyl)benzyl)-5H-pyrrolo[3,2-d]pyrimidine-4-amine formate was prepared with the procedures of Step G according to Example 1.

¹HNMR (Methanol-4, 400 MHz): δ 8.50 (s, 2H), 7.41-7.28 (m, 5H), 4.45 (t, J=6.8 Hz, 2H), 4.31 (s, 2H), 4.06 (s, 2H), 3.31-3.29 (m, 4H), 2.10-2.07 (m, 4H), 1.81-1.76 (m, 2H), 1.54-1.49 (m, 2H), 1.01 (t, J=6.8 Hz, 3H).

MS(ESI) m/z: 380[M+H⁺].

Example 5

2-butoxy-7-(4-((3,3-difluoropyrrolidin-1-yl)methyl)benzyl-5H-pyrrolo[3,2-d]pyrimidine-4-amine

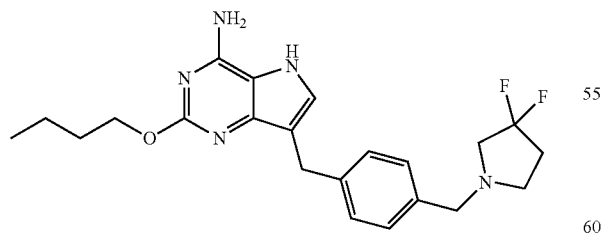

Step A: 4-((4-amino-2-butoxy-5-((2-(trimethylsilyl)ethoxyl)methyl)-5H-pyrrolo[3,2-d]pyrimidine-7-yl) (hydroxyl) methyl)benzaldehyde was prepared according to Example 1, wherein 1,4-benzenedialdehyde was used instead of 1,3-benzenedialdehyde in Step E.

LCMS(ESI) m/z: 471[M+H⁺].

Step B: (4-amino-2-butoxy-5-((2-(trimethylsilyl)ethoxyl)methyl)-5H-pyrrolo[3,2-d]pyrimidine-7-yl)(4-((3,3-difluoropyrrolidine-1-yl)methyl)phenyl)methanol was prepared according to Example 1, wherein 3,3-difluoropyrrolidine was used instead of 1-methylpiperazine in Step F.

LCMS(ESI) m/z: 562[M+H⁺].

Step C: 2-butoxy-7-(4-((3,3-difluoropyrrolidine-1-yl)methyl)benzyl)-5H-pyrrolo[3,2-d]pyrimidine-4-amine was prepared with the procedures of Step G according to Example 1.

¹HNMR (Methanol-4, 400 MHz): δ 7.28-7.15 (m, 4H), 7.04 (s, 1H), 4.30 (t, J=6.4 Hz, 2H), 3.97 (s, 2H), 3.59 (s, 2H), 2.88-2.71 (m, 4H), 2.30-2.19 (m, 2H), 1.78-1.71 (m, 2H), 1.55-1.46 (m, 2H), 0.98 (t, J=7.2 Hz, 3H).

MS(ESI) m/z: 416[M+H⁺].

Example 6

2-butoxy-7-(4-((3-fluoropyrrolidine-1-yl)methyl)benzyl)-5H-pyrrolo[3,2-d]pyrimidine-4-amine

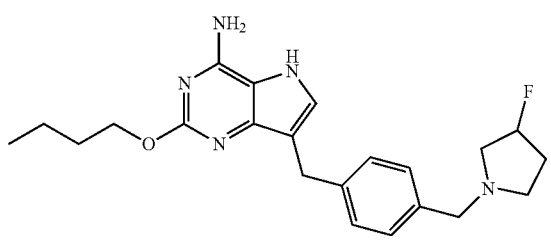 [SMILES: CCCCOc1nc(N)c2[nH]cc(Cc3ccc(CN4CCC(F)C4)cc3)c2n1]

Step A: (4-amino-2-butoxy-5-((2-(trimethylsilyl)ethoxyl)methyl)-5H-pyrrolo[3,2-d]pyrimidine-7-yl)(4-((3-fluoropyrrolidine-1-yl)methyl)phenyl)methanol was prepared according to Example 5, wherein 3-fluoropyrrolidine was used instead of 3,3-difluoropyrrolidine in Step B.

LCMS(ESI) m/z: 544[M+H⁺].

Step B: 2-butoxy-7-(4-((3-fluoropyrrolidine-1-yl)methyl)benzyl)-5H-pyrrolo[3,2-d]pyrimidine-4-amine was prepared with the procedures of Step C according to Example 5.

¹HNMR (Methanol-4, 400 MHz): δ 7.30-7.24 (m, 4H), 7.06 (s, 1H), 5.24-5.08 (m, 1H), 4.32 (t, J=6.4 Hz, 2H), 3.99 (s, 2H), 3.69-3.57 (m, 2H), 2.88-2.65 (m, 4H), 2.45-2.43 (m, 1H), 2.25-2.11 (m, 1H), 2.02-1.91 (m, 1H), 1.78-1.73 (m, 2H), 1.57-1.50 (m, 2H), 1.01 (t, J=7.2 Hz, 3H).

MS(ESI) m/z: 398 [M+H⁺].

Example 7

1-(4-((4-amino-2-butoxy-5H-pyrrolo[3,2-d]pyrimidine-7-yl)methyl)benzyl)pyrrolidine-3-ol

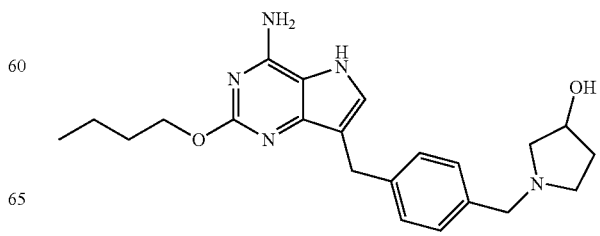

Step A: 1-(4-((4-amino-2-butoxy-5-((2-(trimethylsilyl)ethoxyl)methyl)-5H-pyrrolo[3,2-d]pyrimidine-7-yl)(hydroxyl)methyl)benzyl)pyrrolidine-3-ol was prepared according to Example 5, wherein pyrrolidine-3-ol was used instead of 3,3-difluoropyrrolidine in Step B.

LCMS(ESI) m/z: 542[M+H$^+$].

Step B: 1-(4-((4-amino-2-butoxy-5H-pyrrolo[3,2-d]pyrimidine-7-yl)methyl)benzyl)pyrrolidine-3-ol formate was prepared with the procedures of Step C according to Example 5.

$^1$HNMR (Methanol-4, 400 MHz): δ 8.43 (s, 2H), 7.45-7.39 (m, 4H), 7.25 (s, 1H), 4.53 (m, 1H), 4.44-4.27 (m, 2H), 4.04 (s, 2H), 3.54-3.47 (m, 1H), 3.38-3.36 (m, 4H), 3.22-3.19 (m, 1H), 2.28-2.24 (m, 1H), 2.05-2.01 (m, 1H), 1.82-1.76 (m, 2H), 1.56-1.50 (m, 2H), 1.01 (t, J=7.2 Hz, 3H).

MS(ESI) m/z: 396[M+H$^+$].

Example 8

2-butoxy-7-(4-(piperidine-1-ylmethyl)benzyl)-5H-pyrrolo[3,2-d]pyrimidine-4-amine

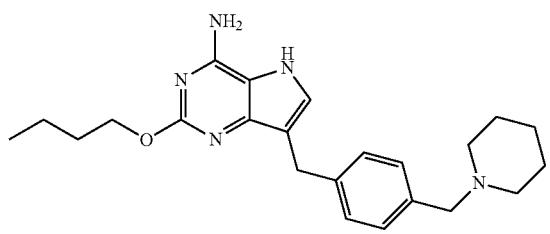 [SMILES: CCCCOc1nc(N)c2[nH]cc(Cc3ccc(CN4CCCCC4)cc3)c2n1]

Step A: (4-amino-2-butoxy-5-((2-(trimethylsilyl)ethoxyl)methyl)-5H-pyrrolo[3,2-d]pyrimidine-7-yl)(4-(piperidine-1-ylmethyl)phenyl)methanol was prepared according to Example 5, wherein piperidine was used instead of 3,3-difluoropyrrolidine in Step B.

LCMS(ESI) m/z: 540[M+H$^+$].

Step B: 2-butoxy-7-(4-(piperidine-1-ylmethyl)benzyl)-5H-pyrrolo[3,2-d]pyrimidine-4-amine was prepared with the procedures of Step C according to Example 5.

$^1$HNMR (Methanol-4, 400 MHz): δ 7.28 (d, J=8.0 Hz, 2H), 7.22 (d, J=8.0 Hz, 2H), 7.04 (s, 1H), 4.30 (t, J=6.6 Hz, 2H), 3.98 (s, 2H), 3.47 (s, 2H), 2.42 (s, 4H), 1.77-1.73 (m, 2H), 1.60-1.57 (m, 4H), 1.52-1.46 (m, 4H), 0.99 (t, J=7.4 Hz, 3H).

MS (ESI) m/z: 394 [M+H$^+$].

Example 9

2-butoxy-7-(4-(morpholinomethyl)benzyl)-5H-pyrrolo[3,2-d]pyrimidine-4-amine

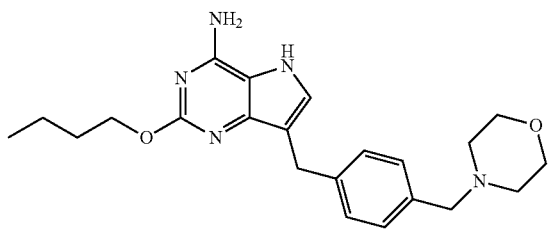 [SMILES: CCCCOc1nc(N)c2[nH]cc(Cc3ccc(CN4CCOCC4)cc3)c2n1]

Step A: (4-amino-2-butoxy-5-((2-(trimethylsilyl)ethoxyl)methyl)-5H-pyrrolo[3,2-d]pyrimidine-7-yl)(4-(morpholinomethyl)phenyl)methanol was prepared according to Example 5, wherein morpholine is used instead of 3,3-difluoropyrrolidine in Step B.

LCMS(ESI) m/z: 542[M+H$^+$].

Step B: 2-butoxy-7-(4-(morpholinomethyl)benzyl)-5H-pyrrolo[3,2-d]pyrimidine-4-amine was prepared with the procedures of Step C according to Example 5.

$^1$HNMR (Methanol-4, 400 MHz): δ 7.28 (d, J=8.0 Hz, 2H), 7.22 (d, J=8.0 Hz, 2H), 7.03 (s, 1H), 4.29 (t, J=6.6 Hz, 2H), 3.96 (s, 2H), 3.67-3.64 (m, 4H), 3.46 (s, 2H), 2.43 (s, 4H), 1.77-1.72 (m, 2H), 1.55-1.45 (m, 2H), 0.98 (t, J=7.4 Hz, 3H).

MS(ESI) m/z: 396[M+H$^+$].

Example 10

2-butoxy-7-(4-((4-methylpiperazine-1-yl)methyl)benzyl)-5H-pyrrolo[3,2-d]pyrimidine-4-amine

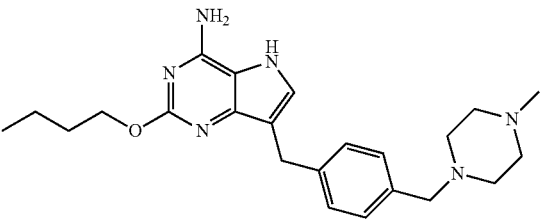 [SMILES: CCCCOc1nc(N)c2[nH]cc(Cc3ccc(CN4CCN(C)CC4)cc3)c2n1]

Step A: (4-amino-2-butoxy-5-((2-(trimethylsilyl)ethoxyl)methyl)-5H-pyrrolo[3,2-d]pyrimidine-7-yl)(4-((4-methylpiperazine-1-yl)methyl)phenyl)methanol was prepared according to Example 5, wherein 1-methylpiperazine was used instead of 3,3-difluoropyrrolidine in Step B.

LCMS(ESI) m/z: 555[M+H$^+$].

Step B: 2-butoxy-7-(4-((4-methylpiperazine-1-yl)methyl)benzyl)-5H-pyrrolo[3,2-d]pyrimidine-4-amine was prepared with the procedures of Step C according to Example 5.

$^1$HNMR (Methanol-4, 400 MHz): δ 7.29 (d, J=8.0 Hz, 2H), 7.22 (d, J=8.0 Hz, 2H), 7.04 (s, 1H), 4.31 (t, J=6.6 Hz, 2H), 3.97 (s, 2H), 3.50 (s, 2H), 2.49-2.26 (m, 11H), 1.79-1.72 (m, 2H), 1.56-1.47 (m, 2H), 0.99 (t, J=7.4 Hz, 3H).

MS(ESI) m/z: 409[M+H$^+$].

Example 11

2-butoxy-7-(4-((dimethylamino)methyl)benzyl)-5H-pyrrolo[3,2-d]pyrimidine-4-amine

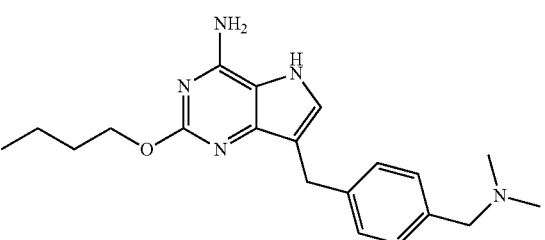

Step A: (4-amino-2-butoxy-5-((2-(trimethylsilyl)ethoxyl)methyl)-5H-pyrrolo[3,2-d]pyrimidine-7-yl)(4-((dimethylamino)methyl)phenyl)methanol was prepared according to Example 5, wherein dimethylamine was used instead of 3,3-difluoropyrrolidine in Step B.

LCMS(ESI) m/z: 500[M+H$^+$].

Step B: 2-butoxy-7-(4-(((dimethylamino)methyl)benzyl)-5H-pyrrolo[3,2-d]pyrimidine-4-amine formate was prepared with the procedures of Step C according to Example 5.

$^1$HNMR (Methanol-4, 400 MHz): δ 8.48 (s, 2H), 7.41 (s, 4H), 7.26 (s, 1H), 4.43 (t, J=6.8 Hz, 2H), 4.22 (s, 2H), 4.06 (s, 2H), 2.79 (s, 6H), 1.79 (m, J=6.8 Hz, 2H), 1.55-1.49 (m, 2H), 1.01 (t, J=6.8 Hz, 3H).

MS(ESI) m/z: 354[M+H$^+$].

Example 12

2-butoxy-7-(4-(((diethylamino)methyl)benzyl)-5H-pyrrolo[3,2-d]pyrimidine-4-amine

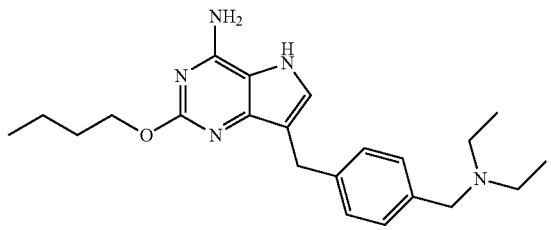 [SMILES: CCCCOc1nc(N)c2[nH]cc(Cc3ccc(CN(CC)CC)cc3)c2n1]

Step A: (4-amino-2-butoxy-5-((2-(trimethylsilyl)ethoxyl) methyl)-5H-pyrrolo[3,2-d]pyrimidine-7-yl)(4-((diethylamino)methyl)phenyl)methanol was prepared according to Example 5, wherein diethylamine was used instead of 3,3-difluoropyrrolidine in Step B.

LCMS(ESI) m/z: 528[M+H$^+$].

Step B: 2-butoxy-7-(4-(((diethylamino)methyl)benzyl)-5H-pyrrolo[3,2-d]pyrimidine-4-amine formate was prepared with the procedures of Step C according to Example 5.

$^1$HNMR (Methanol-4, 400 MHz): δ 8.48 (s, 2H), 7.42 (s, 4H), 7.25 (s, 1H), 4.41 (t, J=6.8 Hz, 2H), 4.28 (s, 2H), 4.06 (s, 2H), 3.20-3.15 (m, 4H), 1.82-1.77 (m, 2H), 1.55-1.49 (m, 2H), 1.34 (t, J=6.8 Hz, 6H), 1.01 (t, J=6.8 Hz, 3H).

MS(ESI) m/z: 382[M+H$^+$].

Example 13

2-butoxy-7-(4-(((dipropylamino)methyl)benzyl)-5H-pyrrolo[3,2-d]pyrimidine-4-amine

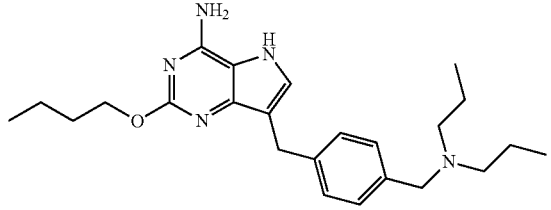 [SMILES: CCCCOc1nc(N)c2[nH]cc(Cc3ccc(CN(CCC)CCC)cc3)c2n1]

Step A: (4-amino-2-butoxy-5-((2-(trimethylsilyl)ethoxyl) methyl)-5H-pyrrolo[3,2-d]pyrimidine-7-yl)(4-((dipropylamino)methyl)phenyl)methanol was prepared according to Example 5, wherein dipropylamine was used instead of 3,3-difluoropyrrolidine in Step B.

LCMS(ESI) m/z: 556[M+H$^+$].

Step B: 2-butoxy-7-(4-(((dipropylamino)methyl)benzyl)-5H-pyrrolo[3,2-d]pyrimidine-4-amine was prepared with the procedures of Step C according to Example 5.

$^1$HNMR (Methanol-4, 400 MHz): δ 7.29-7.19 (m, 4H), 7.04 (s, 1H), 4.32 (t, J=6.5 Hz, 1H), 3.99 (s, 2H), 3.55 (s, 2H), 2.41-2.37 (m, 4H), 1.78-1.74 (m, 2H), 1.57-1.47 (m, 6H), 1.00 (t, J=7.4 Hz, 3H), 0.87 (t, J=7.4 Hz, 6H).

MS(ESI) m/z: 410[M+H$^+$].

Example 14

7-(4-(azetidin-1-ylmethyl)benzyl)-2-butoxy-5H-pyrrolo[3,2-d]pyrimidine-4-amine

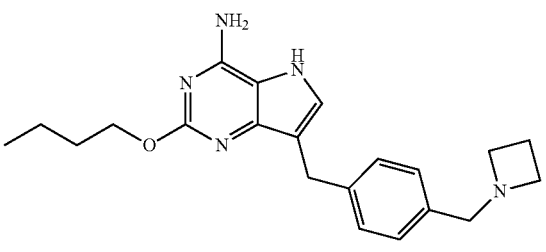 [SMILES: CCCCOc1nc(N)c2[nH]cc(Cc3ccc(CN4CCC4)cc3)c2n1]

Step A: (4-amino-2-butoxy-5-((2-(trimethylsilyl)ethoxyl) methyl)-5H-pyrrolo[3,2-d]pyrimidine-7-yl) (4-(azetidin-1-ylmethyl)phenyl)methanol was prepared according to Example 5, wherein azetidin was used instead of 3,3-difluoropyrrolidine in Step B.

LCMS (ESI) m/z: 512 [M+H$^+$].

Step B: 7-(4-(azetidin-1-ylmethyl)benzyl)-2-butoxy-5H-pyrrolo[3,2-d]pyrimidine-4-amine was prepared with the procedures of Step C according to Example 5.

$^1$HNMR (Methanol-4, 400 MHz): δ 7.28 (d, J=8.0 Hz, 2H), 7.18 (d, J=8.0 Hz, 2H), 7.04 (s, 1H), 4.31 (t, J=6.8 Hz, 2H), 3.98 (s, 2H), 3.59 (s, 2H), 3.30-3.27 (m, 4H), 2.15-2.10 (m, 2H), 1.78-1.73 (m, 2H), 1.56-1.52 (m, 2H), 1.01 (t, J=6.8 Hz, 3H).

MS(ESI) m/z: 366[M+H$^+$].

Example 15

2-butoxy-7-(4-((3-methoxylazetidin-1-yl)methyl)benzyl)-5H-pyrrolo[3,2-d]pyrimidine-4-amine

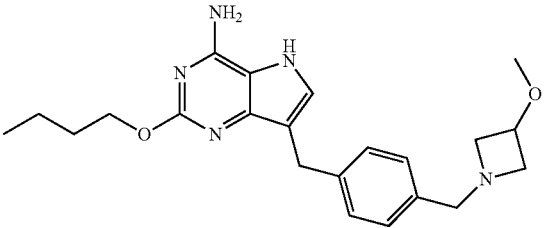 [SMILES: CCCCOc1nc(N)c2[nH]cc(Cc3ccc(CN4CC(OC)C4)cc3)c2n1]

Step A: (4-amino-2-butoxy-5-((2-(trimethylsilyl)ethoxyl) methyl)-5H-pyrrolo[3,2-d]pyrimidine-7-yl)(4-((3-methoxylazetidin-1-yl)methyl)phenyl)methanol was prepared according to Example 5, wherein 3-methoxylazetidin was used instead of 3,3-difluoropyrrolidine in Step B.

LCMS(ESI) m/z: 542[M+H$^+$].

Step B: 2-butoxy-7-(4-((3-methoxylazetidin-1-yl)methyl)benzyl)-5H-pyrrolo[3,2-d]pyrimidine-4-amine was prepared with the procedures of Step C according to Example 5.

¹HNMR (Methanol-4, 400 MHz): δ 7.28 (d, J=8.0 Hz, 2H), 7.18 (d, J=8.0 Hz, 2H), 7.04 (s, 1H), 4.31 (t, J=6.8 Hz, 2H), 4.06-4.04 (m, 1H), 3.98 (s, 2H), 3.60 (s, 2H), 3.54-3.52 (m, 2H), 3.24 (s, 3H), 3.04-3.02 (m, 2H), 1.78-1.73 (m, 2H), 1.56-1.52 (m, 2H), 1.01 (t, J=6.8 Hz, 3H).
MS (ESI) m/z: 396 [M+H⁺].

Example 16

2-butoxy-7-(4-((4-methyl-1,4-diazepan-1-yl)methyl)benzyl)-5H-pyrrolo[3,2-d]pyrimidine-4-amine

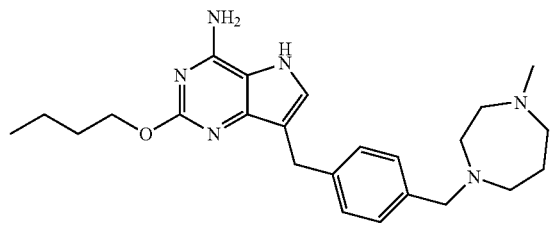 [SMILES: CCCCOc1nc(N)c2[nH]cc(Cc3ccc(CN4CCCN(C)CC4)cc3)c2n1]

Step A: ((4-amino-2-butoxy-5-((2-(trimethylsilyl)ethoxyl)methyl)-5H-pyrrolo[3,2-d]pyrimidine-7-yl)(4-((4-methyl-1,4-diazepan-1-yl)methyl)phenyl)methanol was prepared according to Example 5, wherein 1-methyl-1,4-diazepane was used instead of 3,3-difluoropyrrolidine in Step B.
LCMS(ESI) m/z: 569[M+H⁺].
Step B: 2-butoxy-7-(4-((4-methyl-1,4-diazepan-1-yl)methyl)benzyl)-5H-pyrrolo[3,2-d]pyrimidine-4-amine formate was prepared with the procedures of Step C according to Example 5.
¹HNMR (Methanol-4, 400 MHz): δ 8.41 (s, 3H), 7.34-7.24 (m, 5H), 4.52 (t, J=6.8 Hz, 2H), 3.99 (s, 2H), 3.76 (s, 2H), 3.38-3.36 (m, 2H), 3.29-3.27 (m, 2H), 2.95 (s, 2H), 2.87-2.84 (m, 5H), 2.07-2.05 (m, 2H), 1.84-1.80 (m, 2H), 1.55-1.49 (m, 2H), 1.03-0.99 (t, J=8.0 Hz, 3H).
MS(ESI) m/z: 423[M+H⁺].

Example 17

2-butoxy-7-(4-((2,6-dimethylmorpholinyl)methyl)benzyl)-5H-pyrrolo[3,2-d]pyrimidine-4-amine

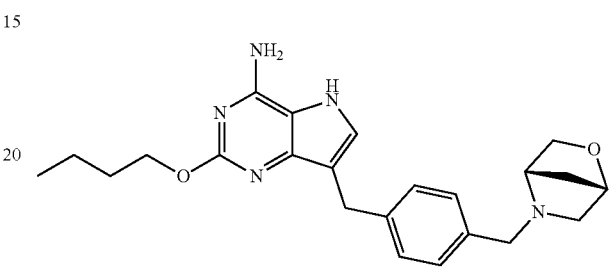

Step A: (4-amino-2-butoxy-5-((2-(trimethylsilyl)ethoxyl)methyl)-5H-pyrrolo[3,2-d]pyrimidine-7-yl)(4-((2,6-dimethylmorpholinyl)methyl)phenyl)methanol was prepared according to Example 5, wherein 2,6-dimethylmorpholine was used instead of 3,3-difluoropyrrolidine in Step B.
LCMS(ESI) m/z: 570 [M+H⁺].
Step B: 2-butoxy-7-(4-((2,6-dimethylmorpholinyl)methyl)benzyl)-5H-pyrrolo[3,2-d]pyrimidine-4-amine was prepared with the procedures of Step C according to Example 5.

¹HNMR (Methanol-4, 400 MHz): δ 7.30-7.28 (d, J=8.0 Hz, 2H), 7.23-7.21 (d, J=8.0 Hz, 2H), 7.06 (s, 1H), 4.34-4.30 (t, J=8.0 Hz, 2H), 3.99 (s, 2H), 3.69-3.64 (m, 2H), 3.47 (s, 2H), 2.73 (d, J=12.0 Hz, 2H), 1.77-1.70 (m, 4H), 1.54-1.51 (m, 2H), 1.11 (d, J=10.4 Hz, 6H), 1.00 (t, J=8.0 Hz, 3H).
MS(ESI) m/z: 424[M+H⁺].

Example 18

7-(4-(((1S,4S)-2-oxa-5-azabicyclo[2.2.1]heptane-5-ylmethyl)benzyl)-2-butoxy-5H-pyrrolo[3,2-d]pyrimidine-4-amine

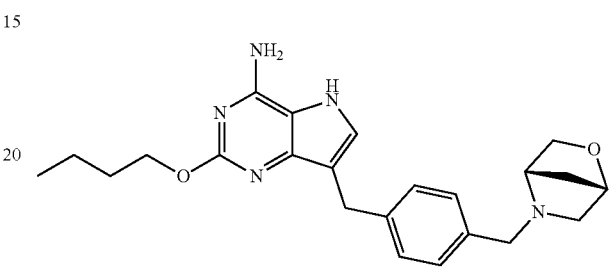

Step A: (4-((1S,4S)-2-oxa-5-azabicyclo[2.2.1]heptane-5-ylmethyl)phenyl)(4-amino-2-butoxy-5-((2-(trimethylsilyl)ethoxyl)methyl)-5H-pyrrolo[3,2-d]pyrimidine-7-yl)methanol was prepared according to Example 5, wherein (1S,4S)-2-oxa-5-azabicyclo[2.2.1]heptane was used instead of 3,3-difluoropyrrolidine in Step B.
LCMS(ESI) m/z: 554[M+H⁺].
Step B: 7-(4-((1S,4S)-2-oxa-5-azabicyclo[2.2.1]heptane-5-ylmethyl)benzyl)-2-butoxy-5H-pyrrolo[3,2-D]pyrimidine-4-amine formate was prepared with the procedures of Step C according to Example 5.
¹HNMR (Methanol-4, 400 MHz): δ:8.38 (brs, 2H), 7.45 (d, J=8.4 Hz, 2H), 7.37 (d, J=8.4 Hz, 2H), 7.29 (s, 1H), 4.66 (s, 1H), 4.47 (t, J=6.8 Hz, 2H), 4.36-4.27 (m, 1H), 4.24-4.23 (m, 2H), 4.16-4.13 (m, 1H), 4.04 (s, 2H), 3.82-3.81 (m, 1H), 3.33-3.31 (m, 2H), 2.33-2.29 (m, 1H), 2.14-2.11 (m, 1H), 1.83-1.76 (m, 2H), 1.56-1.48 (m, 2H), 1.01 (t, J=7.2 Hz, 3H).
MS(ESI) m/z: 408[M+H⁺].

Example 19

2-butoxy-7-(4-((4-methoxylpiperidine-1-yl)methyl)benzyl)-5H-pyrrolo[3,2-d]pyrimidine-4-amine

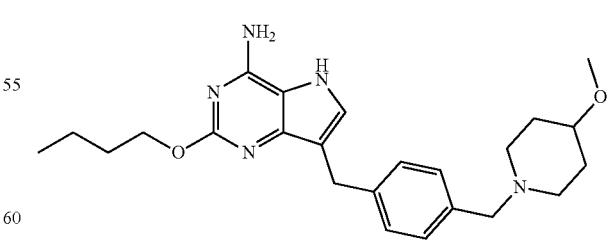

Step A: (4-amino-2-butoxy-5-((2-(trimethylsilyl)ethoxyl)methyl)-5H-pyrrolo[3,2-d]pyrimidine-7-yl)(4-((4-methoxylpiperidine-1-yl)methyl)phenyl)methanol was prepared according to Example 5, wherein 4-methoxylpiperidine was used instead of 3,3-difluoropyrrolidine in Step B.

LCMS(ESI) m/z: 570[M+H$^+$].

Step B: 2-butoxy-7-(4-((4-methoxylpiperidine-1-yl) methyl)benzyl)-5H-pyrrolo[3,2-d]pyrimidine-4-amine formate with the procedures of Step C according to Example 5.

$^1$HNMR (Methanol-4, 400 MHz): δ: 8.45 (s, 2H), 7.43-7.38 (m, 4H), 7.28 (s, 1H), 4.45 (t, J=6.4 Hz, 2H), 4.21 (s, 2H), 4.05 (s, 2H), 3.52-3.53 (m, 1H), 3.33-3.39 (m, 3H), 3.26-3.24 (m, 2H), 3.13-3.10 (m, 2H), 1.99-1.92 (m, 4H), 1.84-1.77 (m, 2H), 1.56-1.50 (m, 2H), 1.01 (t, J=7.2 Hz, 3H).

MS(ESI) m/z: 424[M+H$^+$].

Example 20

2-butoxy-7-(4-((4-isopropylpiperazine-1-yl)methyl) benzyl)-5H-pyrrolo[3,2-d]pyrimidine-4-amine

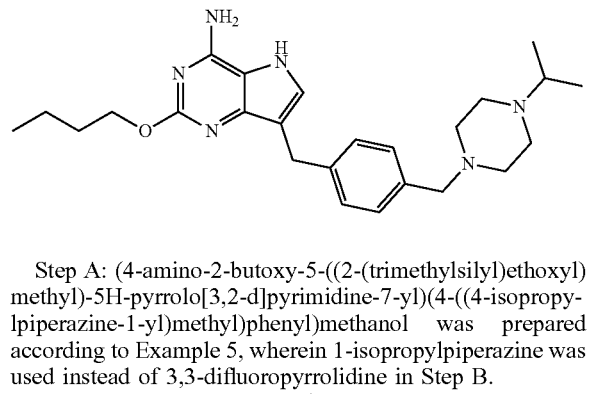

Step A: (4-amino-2-butoxy-5-((2-(trimethylsilyl)ethoxyl) methyl)-5H-pyrrolo[3,2-d]pyrimidine-7-yl)(4-((4-isopropylpiperazine-1-yl)methyl)phenyl)methanol was prepared according to Example 5, wherein 1-isopropylpiperazine was used instead of 3,3-difluoropyrrolidine in Step B.

LCMS(ESI) m/z: 583[M+H$^+$].

Step B: 2-butoxy-7-(4-((4-isopropylpiperazine-1-yl) methyl)benzyl)-5H-pyrrolo[3,2-d]pyrimidine-4-amine formate was prepared with the procedures of Step C according to Example 5.

$^1$H NMR (Methanol-4, 300 MHz): δ: 8.45 (s, 2H), 7.31-7.25 (m, 5H), 4.49 (t, J=8.4 Hz, 2H), 3.99 (s, 2H), 3.64 (s, 2H), 3.42-3.40 (m, 1H), 3.21-3.25 (m, 4H), 2.66-2.82 (m, 4H), 1.84-1.79 (m, 2H), 1.56-1.51 (m, 2H), 1.35 (d, J=8.8 Hz, 6H), 1.04-0.99 (t, J=10.0 Hz, 3H).

MS(ESI) m/z: 437[M+H$^+$].

Example 21

2-butoxy-7-(4-(pyrrolidine-1-ylmethyl)benzyl)-5H-pyrrolo[3,2-d]pyrimidine-4-amine Step A: (4-amino-2-butoxy-5-((2-(trimethylsilyl)ethoxyl) methyl)-5H-pyrrolo[3,2-d]pyrimidine-7-yl)(4-(pyrrolidine-1-ylmethyl)phenyl)methanol was prepared according to Example 5, wherein pyrrole was used instead of 3,3-difluoropyrrolidine in Step B.

LCMS(ESI) m/z: 526[M+H$^+$].

Step B: 2-butoxy-7-(4-(pyrrolidine-1-ylmethyl)benzyl)-5H-pyrrolo[3,2-d]pyrimidine-4-amine formate was prepared with the procedures of Step C according to Example 5.

$^1$H NMR (Methanol-4, 400 MHz): δ 8.41 (s, 2H), 7.46 (d, J=8.0 Hz, 2H), 7.40 (d, J=8.0 Hz, 2H), 7.30 (s, 1H), 4.48 (t, J=6.8 Hz, 2H), 4.33 (s, 2H), 4.05 (s, 2H), 3.32-3.30 (m, 4H), 2.10-2.06 (m, 4H), 1.83-1.89 (m, 2H), 1.55-1.48 (m, 2H), 1.02 (t, J=7.2 Hz, 3H).

MS(ESI) m/z: 380[M+H$^+$].

Example 22

2-butoxy-7-((6-(pyrrolidine-1-ylmethyl)pyridine-3-yl)methyl)-5H-pyrrolo[3,2-d]pyrimidine-4-amine

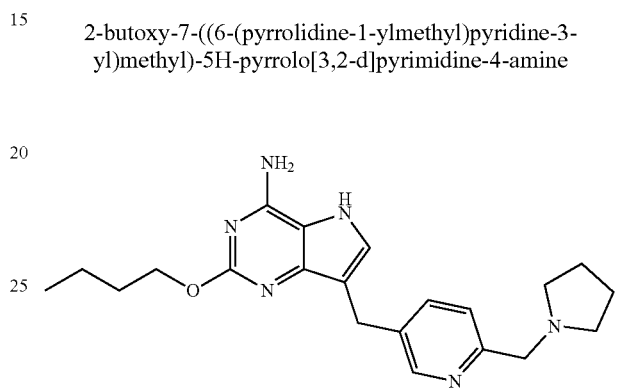

Scheme for Preparing 6-(pyrrolidine-1-ylmethyl)nicotinaldehyde

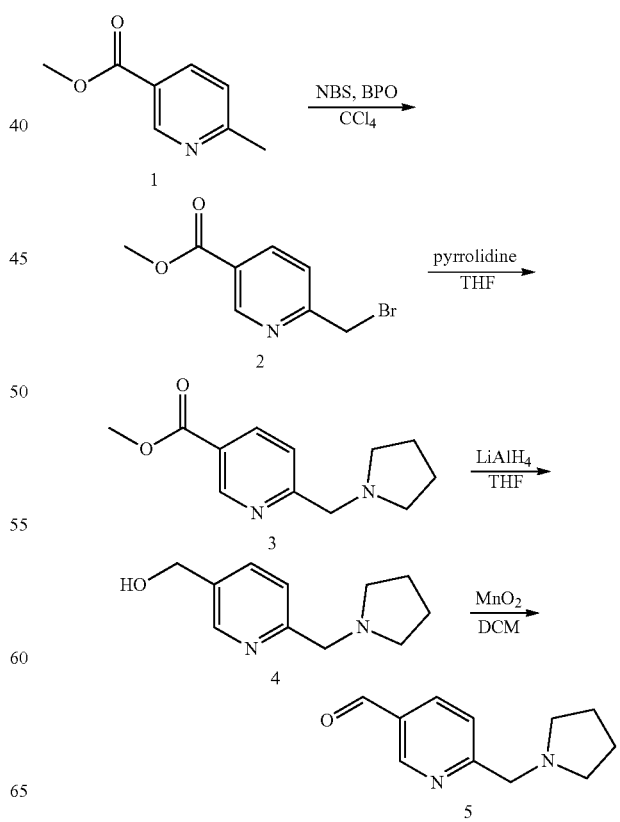

Step A: At room temperature, to a solution of methyl 6-methylnicotinate (10 g, 0.0662 mol) in CCl$_4$ (100 mL) was added NBS (13.0 g, 0.0728 mol) and BPO (1.6 g, 0.0066 mol). The reaction mixture was heated to 75° C. and stirred for 12 h. After cooling, water was added (80 mL) and the mixture was extracted with ethyl acetate (200 mL×2). The organic layer was washed with saturated sodium thiosulfate aqueous solution (80 mL), dried with anhydrous sodium sulfate, and concentrated under reduced pressure. The residue was purified with silica gel column chromatography (eluent: petroleum ether/ethyl acetate=20/1) to give methyl 6-(bromomethyl)nicotinate (5.2 g, yield 34%) as brown solid.

$^1$HNMR(CD Cl$_3$, 400 MHz): δ 9.18 (d, J=1.6 Hz, 1H), 8.32 (dd, J$_1$=8.0 Hz, J$_2$=2.0 Hz, 1H), 7.55 (d, J=8.0 Hz, 1H), 4.60 (s, 2H), 3.97 (s, 3H).

MS(ESI) m/z: 230, 232[M+H$^+$].

Step B: At 0° C., to a solution of pyrrolidine (3.09 g, 43.47 mmol) and triethylamine (3 mL, 21.73 mmol) in anhydrous tetrahydrofuran (100 mL) was added methyl 6-(bromomethyl)nicotinate (5.0 g, 21.73 mmol) in portions. After addition, the reaction mixture was stirred at room temperature for 16 h, diluted with water (80 mL) and extracted with ethyl acetate (100 mL). The organic layer was dried with anhydrous sodium sulfate and concentrated under reduced pressure. The residue was purified with silica gel column chromatography (eluent: petroleum ether/ethyl acetate=10/1) to give methyl 6-(pyrrolidine-1-ylmethyl)nicotinate (4.1 g, yield 86%) as brown solid.

$^1$HNMR(CDCl$_3$, 400 MHz): δ 9.11 (d, J=2.0 Hz, 1H), 8.22 (dd, J$_1$=8.0 Hz, J$_2$=2 0.0 Hz, 1H), 7.48 (d, J=8.0 Hz, 1H), 3.91 (s, 3H), 3.81 (s, 2H), 2.58-2.53 (m, 4H), 1.81-1.77 (m, 4H).

MS(ESI) m/z: 221[M+H$^+$].

Step C: At a temperature below 0° C., to a solution of methyl 6-(pyrrolidine-1-ylmethyl)nicotinate (3.0 g, 13.62 mmol) in anhydrous tetrahydrofuran (70 mL) was added lithium aluminum hydride (1.03 g, 27.24 mmol) in portions with stirring. The reaction was performed at about 0° C. for 2 h and at room temperature for a further 30 min. TLC showed disappearance of reactants. The mixture was cooled to 0° C. and water (1 mL) was added very slowly. Then 15% sodium hydroxide aqueous solution (1 mL) and water (3 mL) were added with vigor stirring. The resultant mixture was filtered. The filtrate was dried with anhydrous Mg$_2$SO$_4$ and concentrated to dryness under reduced pressure to give (6-(pyrrolidine-1-ylmethyl)pyridine-3-yl)methanol (2.5 g).

$^1$HNMR (CD Cl$_3$, 400 MHz): δ 8.41 (d, J=1.6 Hz, 1H), 7.67 (dd, J$_1$=8.0 Hz, J$_2$=2 0.0 Hz, 1H), 7.37 (d, J=8.0 Hz, 1H), 4.67 (s, 2H), 3.75 (s, 2H), 2.57-2.543 (m, 4H), 1.81-1.76 (m, 4H).

Step D: (6-(pyrrolidine-1-ylmethyl)pyridine-3-yl)methanol (2.5 g, 13 mmol) was dissolved in anhydrous dichloromethane (50 mL). At 0° C., manganese dioxide (5.0 g, 58 mmol) was added in portions. The reaction mixture was stirred at room temperature for 24 h and filtered. The filtrate was concentrated under vacuum and the residue was purified with silica gel column chromatography (eluent: 15% ethyl acetate in petroleum ether) to give 6-(pyrrolidine-1-ylmethyl)nicotinaldehyde (2.2 g, crude) as yellow oil.

LCMS(ESI) m/z: 191 [M+H$^+$].

Scheme for Preparing 2-butoxy-7-((6-(pyrrolidine-1-ylmethyl)pyridine-3-yl)methyl)-5H-pyrrolo[3,2-d]pyrimidine-4-amine

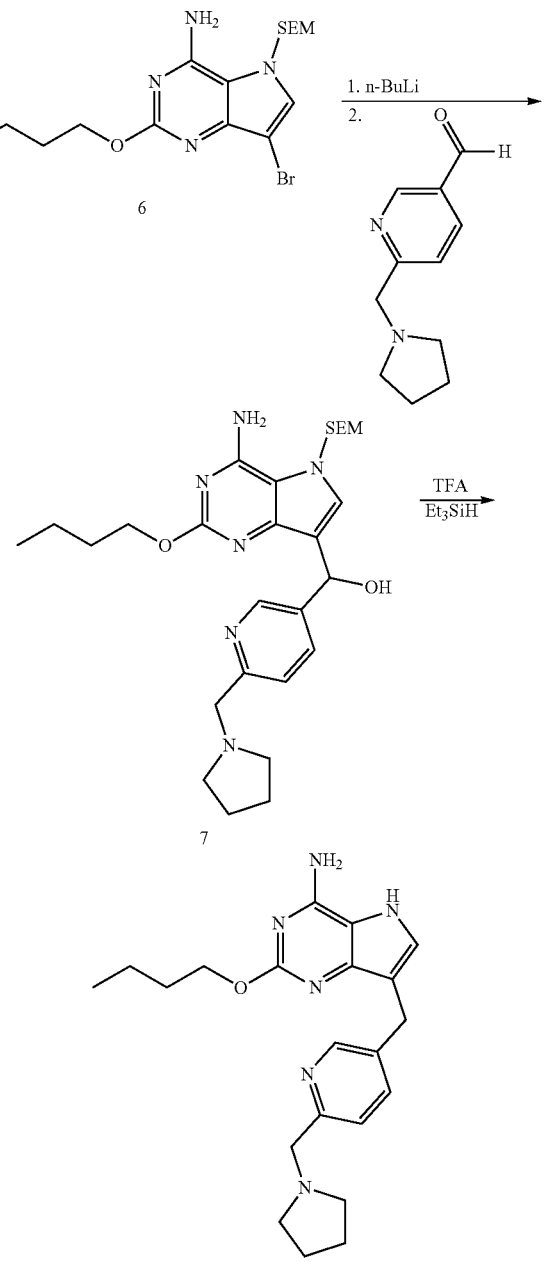

Example 22

Example 22 Procedure

Step E: (4-amino-2-butoxy-5-((2-(trimethylsilyl)ethoxy)methyl)-5H-pyrrolo[3,2-d]pyrimidine-7-yl) (6-(pyrrolidine-1-ylmethyl)pyridine-3-yl)methanol was prepared according to Example 1, wherein 6-(pyrrolidine-1-ylmethyl)nicotinaldehyde was used instead of 1,3-benzenedialdehyde in Step E.

LCMS(ESI) m/z: 527[M+H$^+$].

Step F: 2-butoxy-7-((6-(pyrrolidine-1-ylmethyl)pyridine-3-yl)methyl)-5H-pyrrolo[3,2-d]pyrimidine-4-amine formate was prepared as white solid with the procedures of Step G according to Example 1.

¹HNMR (Methanol-4, 400 MHz): δ 8.62 (s, 1H), 8.40 (brs, 1H), 7.77 (d, J=8.0 Hz, 1H), 7.40 (d, J=8.0 Hz, 1H), 7.35 (s, 1H), 4.48 (s, 2H), 4.45 (t, J=6.4 Hz, 2H), 4.08 (s, 2H), 3.42-3.38 (m, 4H), 2.13-2.10 (m, 4H), 1.83-1.76 (m, 2H), 1.55-1.49 (m, 2H), 1.01 (t, J=7.2 Hz, 3H).

MS(ESI) m/z: 381 [M+H⁺].

Example 23

2-butoxy-7-(3-(2-(pyrrolidine-1-yl)ethyl)benzyl)-5H-pyrrolo[3,2-d]pyrimidine-4-amine

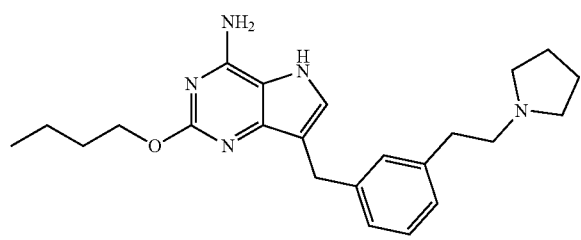 [SMILES: CCCCOc1nc(N)c2[nH]cc(Cc3cccc(CCN4CCCC4)c3)c2n1]

Scheme for Preparing 3-(2-(pyrrolidine-1-yl)ethyl)benzaldehyde

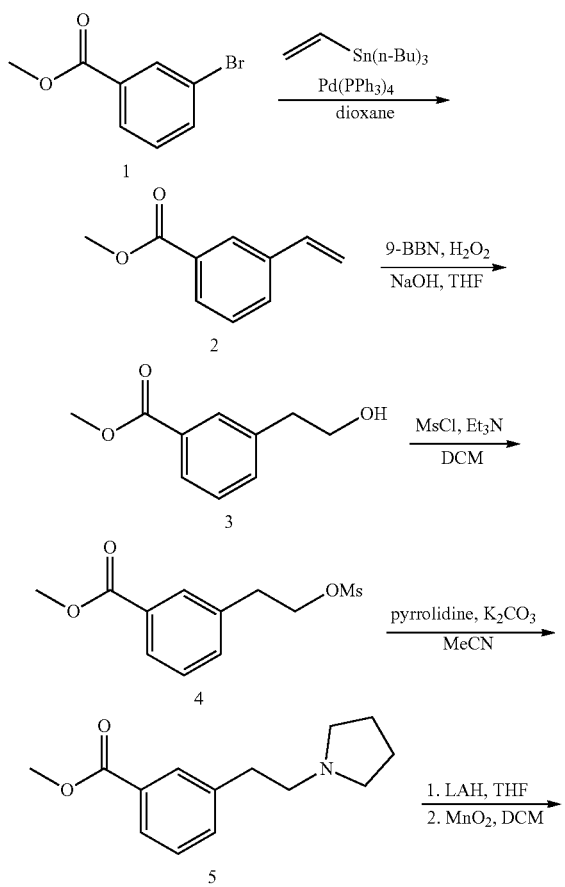

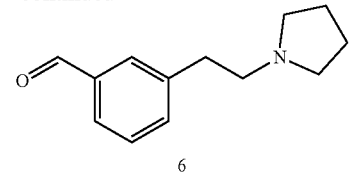

Step A: Under nitrogen atmosphere, a solution of methyl 3-bromobenzoate (17.0 g, 79.0 mmol), tributylvinyltin (33 g, 102 mmol) and Pd(PPh₃)₄ (4.5 g, 4 mmol) in dioxan (200 mL) was stirred at 110° C. for 6 h and the reaction was quenched with addition of 10% potassium fluoride aqueous solution (100 mL). The resultant mixture was stirred at room temperature for a further 10 min and extracted with ethyl acetate (150 mL×3). The combined organic layer was washed with saline, dried with anhydrous sodium sulfate and concentrated under reduced pressure. The residue was purified with silica gel column chromatography (eluent: 25% ethyl acetate in petroleum ether) to give 15 g of crude methyl 3-vinylbenzoate as yellow oil.

MS (ESI) m/z: 163 [M+H⁺].

Step B: Under nitrogen atmosphere, to a solution of methyl 3-vinylbenzoate in anhydrous tetrahydrofuran (100 mL) was added 9-BBN (0.5M, 166 mL, 83 mmol) through a dropping funnel with stirring and the temperature was kept below -30° C. After addition, the reaction mixture was warmed to room temperature and stirred for 16 h. Then the mixture was cooled to -30° C., to which was added H₂O₂ aqueous solution (30 mass %, 19 mL) dropwise and 15% sodium hydroxide aqueous solution (40 mL) dropwise slowly. The resultant mixture was stirred for a further 1 h at ambient temperature, diluted with water (200 mL) and extracted with ethyl acetate (200 mL×2). The combined organic layer was washed with saline, dried with anhydrous sodium sulfate and concentrated under reduced pressure to give 9 g of crude methyl 3-(2-hydroxylethyl)benzoate as yellow oil, which was used for the next step directly.

¹HNMR (CDCl₃, 400 MHz): δ 7.92-7.90 (m, 2H), 7.45-7.37 (m, 2H), 3.92 (s, 3H), 3.89 (t, J=6.5 Hz, 2H), 2.93 (t, J=6.5 Hz, 2H).

MS(ESI) m/z: 181[M+H⁺].

Step C: At about 0° C., to a solution of methyl 3-(2-hydroxylethyl)benzoate (10 g) in anhydrous dichloromethane (90 mL) were added methanesulfonyl chloride (34 g, 299 mmol) and triethylamine (12 g, mmol) with stirring. The reactants were stirred at 0° C. for 1 h, quenched with water (50 mL) and extracted with ethyl acetate (100 mL×3). The combined organic layer was dried with anhydrous sodium sulfate and concentrated under reduced pressure. The residue was purified with silica gel column chromatography (eluent: 10% ethyl acetate in petroleum ether) to give 2.7 g of methyl 3-(2-((methylsulfonyl)oxy)ethyl)benzoate as colorless oil.

MS (ESI) m/z: 259 [M+H⁺].

Step D: pyrrolidine (2.3 g, 31.3 mmol) and potassium carbonate (2.2 g, 16 mmol) were dissolved in anhydrous acetonitrile (20 mL), to which was added a solution of methyl 3-(2-((methylsulfonyl)oxy)ethyl)benzoate (2.7 g, 10.4 mmol) in acetonitrile (5 mL) over 10 min. The reaction liquid was stirred at 70° C. for 16 h, which after being cooled to room temperature was diluted with water (20 mL) and extracted with ethyl acetate (20 mL×3). The combined organic layer was dried with anhydrous sodium sulfate and concentrated under reduced pressure. The residue was purified with silica gel column chromatography (eluent: methanol/dichloromethane is 2%-5%) to give methyl 3-(2-(pyrrolidine-1-yl)ethyl)benzoate (1.7 g, 71%) as yellow oil.

MS(ESI) m/z: 234[M+H$^+$].

Step E: 3-(2-(pyrrolidine-1-yl)ethyl)benzaldehyde was prepared with the procedures of Step C, D according to Example 22.

MS(ESI) m/z: 204[M+H$^+$].

Step F: 2-butoxy-7-(3-(2-(pyrrolidine-1-yl)ethyl)benzyl)-5H-pyrrolo[3,2-d]pyrimidine-4-amine formate was prepared with the procedures of Step E, F according to Example 22.

$^1$HNMR (Methanol-4, 400 MHz): δ 8.42 (s, 2H), 7.30-7.13 (m, 5H), 4.38 (t, J=6.4 Hz, 2H), 4.01 (s, 1H), 3.41 (t, J=7.6 Hz, 2H), 3.35-3.32 (m, 4H), 3.01 (t, J=7.6 Hz, 2H), 2.09-2.05 (m, 4H), 1.81-1.74 (m, 2H), 1.57-1.48 (m, 2H), 1.01 (t, J=7.6 Hz, 3H).

MS (ESI) m/z: 394 [M+H$^+$].

Example 24

2-butoxy-7-(4-(1-(pyrrolidine-1-yl)ethyl)benzyl)-5H-pyrrolo[3,2-d]pyrimidine-4-amine

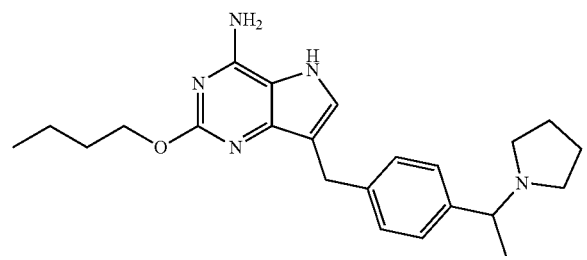 [SMILES: CCCCOc1nc(N)c2[nH]cc(Cc3ccc(C(C)N4CCCC4)cc3)c2n1]

Scheme for Preparing
4-(1-(pyrrolidine-1-yl)ethyl)benzaldehyde

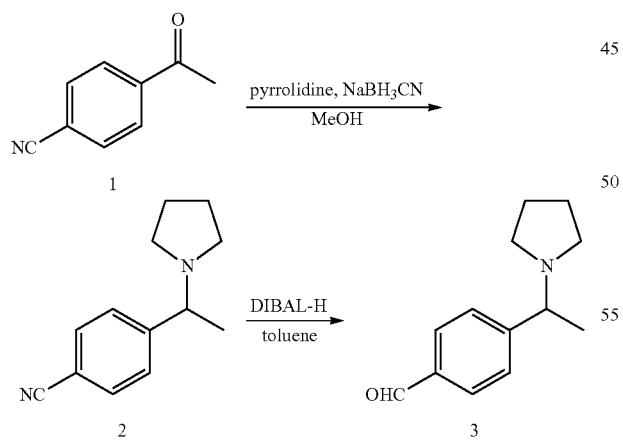

Step A: To a solution of 4-cyanoacetophenone (4 g, 27.56 mmol) and pyrrolidine (2.94 g, 41.33 mmol) in methanol (100 mL) were added acetic acid (0.5 mL) and sodium cyanoborohydride (5.2 g, 82.67 mmol) with stirring and the temperature was kept below 0° C. The reactants were stirred at room temperature for 16 h and concentrated under reduce pressure. The resultant oil was purified with silica gel column chromatography (eluent: petroleum ether/ethyl acetate=1/3) to give 2.8 g of 4-(1-(pyrrolidine-1-yl)ethyl)benzonitrile as colorless oil.

MS(ESI) m/z: 201[M+H$^+$].

Step B: At −20 to −10° C., to a solution of 4-(1-(pyrrolidine-1-yl)ethyl)benzonitrile (2 g, 10 mmol) in anhydrous toluene (100 mL) was added a solution of DIBAL-H (1 M, 20 mL, 20 mmol) over 1 h. The reaction liquid was stirred for a further 3 h, quenched with saturated ammonium chloride aqueous solution and extracted with ethyl acetate. The organic layer was washed with saline, dried with anhydrous sodium sulfate and concentrated under reduced pressure. The resultant solid was purified with silica gel column chromatography (eluent: petroleum ether/ethyl acetate=50/1-10/1) to give 4-(1-(pyrrolidine-1-yl)ethyl)benzaldehyde (680 mg, 33.5%) as colorless oil.

(ESI) m/z: 204[M+H$^+$].

Step C: 2-butoxy-7-(4-(1-(pyrrolidine-1-yl)ethyl)benzyl)-5H-pyrrolo[3,2-d]pyrimidine-4-amine formate was prepared with the procedures of Step E, F according to Example 22.

$^1$HNMR (Methanol-4, 400 MHz): δ 8.50 (s, 2H), 7.44-7.38 (m, 4H), 7.27 (s, 1H), 4.45 (t, J=6.4, 2H), 4.33-4.28 (m, 1H), 4.04 (s, 2H), 3.37-3.33 (m, 2H), 3.14-3.11 (m, 2H), 2.04-2.02 (m, 4H), 1.83-1.78 (m, 2H), 1.72- 1.70 (m, 3H), 1.55-1.49 (m, 2H), 1.01 (t, J=7.4, 3H).

MS (ESI) m/z: 394 [M+H$^+$].

Example 25

2-butoxy-7-(4-(1-methylpiperidine-4-yl)benzyl)-5H-pyrrolo[3,2-d]pyrimidine-4-amine

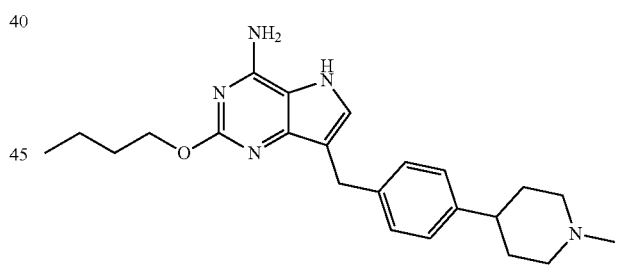

Scheme for Preparing tert-butyl
4-(4-formylphenyl)piperidine-1-formate

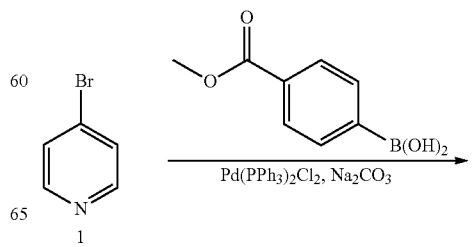

-continued

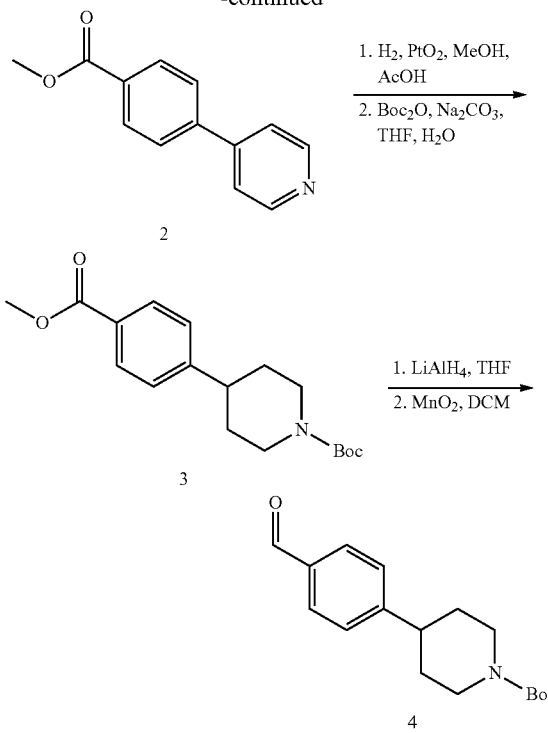

Step A: Under nitrogen atmosphere, a mixture of 4-bromopyridine (3.0 g, 19.0 mmol), (4-(methoxycarbonyl)phenyl)boric acid (2.63 g, 14.6 mmol), Pd(PPh$_3$)$_2$Cl$_2$ (0.35 g, 0.5 mmol) and sodium carbonate (6.91 g, 65.2 mmol) in 1,2-dimethoxyethane (40 mL) was heated to 90° C. and stirred for 10 h. The resultant mixture was concentrated under reduced pressure and the residue was purified with silica gel column chromatography (eluent: petroleum ether/ethyl acetate=6/1-2/1) to give methyl 4-(pyridine-4-yl)benzoate (2.7 g, yield: 86.8%) as white solid.

MS(ESI) m/z: 214[M+H$^+$].

Step B: To a solution of methyl 4-(pyridine-4-yl)benzoate (3.8 g, 17.8 mmol) and PtO$_2$ (0.2 g) in methanol (40 mL) was added 2 mL hydrochloric acid and the mixture was heated to about 50° C. and stirred under hydrogen atmosphere (50 psi) for 16 h. The resultant mixture was filtered and the filtrate was concentrated under reduced pressure to give crude methyl 4-(piperidine-4-yl)benzoate (4.0 g) as hydrochloride without further purification.

MS(ESI) m/z: 220[M+H$^+$].

Step C: To a mixed solution of methyl 4-(piperidine-4-yl)benzoate (5.0 g, 22.8 mmol) and potassium carbonate (25.0 g, 182.2 mmol) in tetrahydrofuran (50 mL)/water (50 mL) was added di-tert-butyl dicarbonate (10.0 g, 45.8 mmol) in portions with stirring and the temperature was kept below 10° C. After addition, the reaction mixture was stirred at room temperature for a further 0.5 h, diluted with water (50 mL) and extracted with ethyl acetate (50 mL×2). The combined organic layer was washed with saline, dried with anhydrous sodium sulfate and concentrated under vacuum. The residue was purified with silica gel column chromatography (eluent: petroleum ether/ethyl acetate=6/1-1/1) to give tert-butyl 4-(4-(methoxycarbonyl)phenyl)piperidine-1-formate (1.9 g, yield: 26.4%) as white solid.

$^1$HNMR(CDCl$_3$, 400 MHz): δ 7.98 (d, J=8.4 Hz, 2H), 7.28 (d, J=7.6 Hz, 2H), 4.27 (s, 1H), 3.91 (s, 3H), 2.84-2.68 (m, 3H), 1.85 (d, J=12.8 Hz, 2H), 1.66-1.59 (m, 2H), 1.49 (s, 9H).

MS(ESI) m/z: 320[M+H$^+$].

Step D: tert-butyl 4-(4-formylphenyl)piperidine-1-formate was prepared with the procedures of Step C, D according to Example 22.

MS(ESI) m/z: 312.1[M+Na$^+$].

Step F: 2-butoxy-7-(4-(piperidine-4-yl)benzyl)-5H-pyrrolo[3,2-d]pyrimidine-4-amine was prepared with the procedures of Step E, F according to Example 22.

MS(ESI) m/z: 380.2 [M+H$^+$].

Preparation of 2-butoxy-7-(4-(1-methylpiperidine-4-yl)benzyl)-5H-pyrrolo[3,2-d]pyrimidine-4-amine

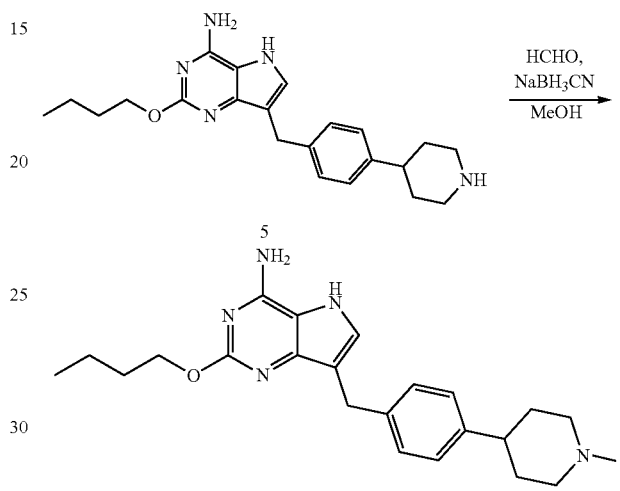

Example 25

Step G: After stirring for 5 min, to a solution of 2-butoxy-7-(4-(piperidine-4-yl)benzyl)-5H-pyrrolo[3,2-d]pyrimidine-4-amine (100 mg, 0.264 mmol) and HCHO (20 mg, 0.666 mmol) in methanol (5 mL) was added sodium cyanoborohydride (50 mg, 0.796 mmol). The reactants were stirred at room temperature for 0.5 h, diluted with water and extracted with ethyl acetate. The organic layer was concentrated under vacuum and the residue was purified with preparative HPLC to give 7.48 mg of 2-butoxy-7-(4-(1-methylpiperidine-4-yl)benzyl)-5H-pyrrolo[3,2-d]pyrimidine-4-amine.

$^1$HNMR (Methanol, 400 MHz): δ 7.21 (d, J=8.0 Hz, 2H), 7.11 (d, J=8.0 Hz, 2H), 7.00 (s, 1H), 4.32-4.28 (m, 2H), 3.94 (s, 2H), 3.00-2.97 (m, 2H), 2.52-2.47 (m, 1H), 2.32 (s, 3H), 2.19-2.15 (m, 2H), 1.80-1.72 (m, 6H), 1.53-1.48 (m, 2H), 0.98 (t, J=7.4 Hz, 3H).

MS (ESI) m/z: 394 [M+H$^+$].

Example 26

2-butoxy-7-(4-(1-methylpyrrolidine)benzyl)-5H-pyrrolo[3,2-d]pyrimidine-4-amine

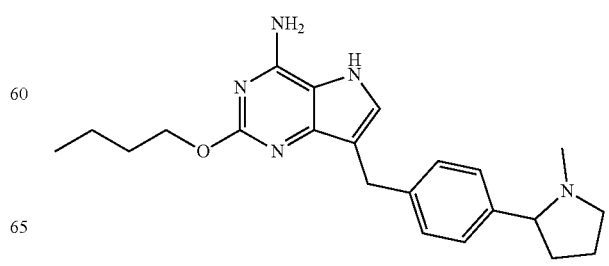

Scheme for Preparing tert-butyl 2-(4-formylphenyl)pyrrolidine-1-formate

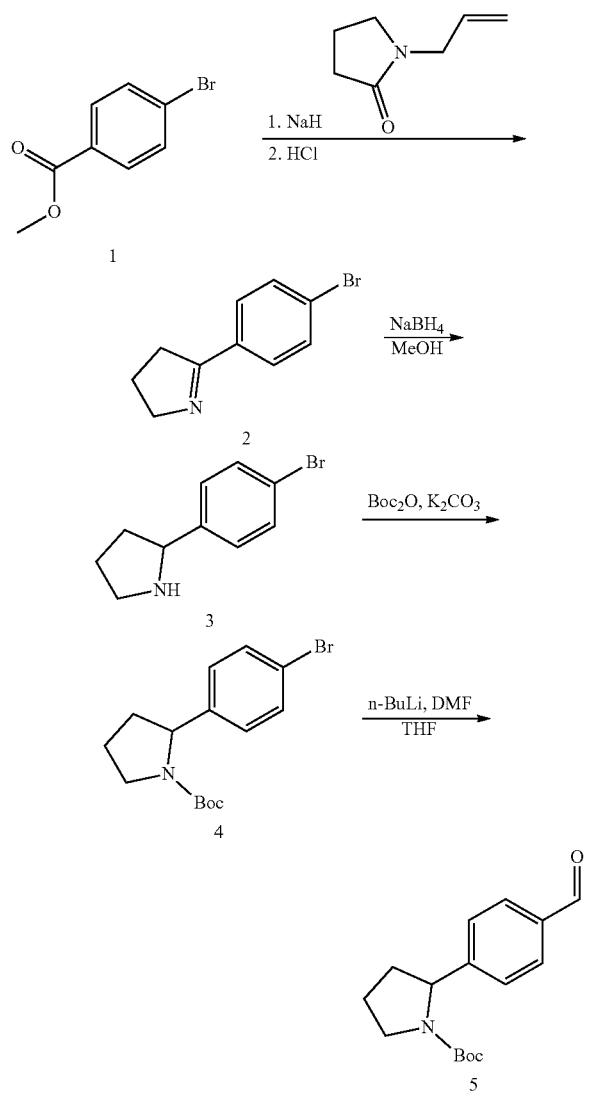

Step A: At 0° C. under N₂ atmosphere, to a mixture of NaH (446 mg, 18.6 mmol) in anhydrous tetrahydrofuran (20 mL) was added 1-allyl-pyrrole-2-one (1.14 g, 9.11 mmol) and then a solution of methyl 4-bromobenzoate in anhydrous tetrahydrofuran (10 mL) slowly. The mixture was stirred at 90° C. for 2 h, then cooled to room temperature, and diluted with 6N hydrochloric acid. The resultant mixture was stirred at 110° C. for 12 h and the aqueous phase was washed with ethyl acetate (50 mL). The mixture was basified with 1N sodium hydroxide until pH was about 9 and then extracted with ethyl acetate (50 mL×2). The combined organic layer was concentrated to dryness under vacuum to give 2.0 g of 5-(4-bromophenyl)-3,4-dihydro-2H-pyrrole as yellow solid, which was used for the next step directly.

Step B: At 0° C. to a solution of 5-(4-bromophenyl)-3,4-dihydro-2H-pyrrole (2.0 g, 9.0 mmol) in methanol (20 mL) was slowly added sodium borohydride (684 mg, 18.1 mmol) with stirring. After addition, the reaction mixture was stirred at room temperature for 1 h. TLC (petroleum ether/ethyl acetate=2:1) showed depletion of starting materials. The resultant mixture was diluted with water (30 mL). To the mixture of the above step was added potassium carbonate (1.51 g, 10.9 mmol) and Boc₂O (2.3 g, 10.5 mmol). The mixture was stirred at 20° C. for 2 h and thin-layer chromatography plate (developing agent: petroleum ether/ethyl acetate=2/1) showed depletion of starting materials. The mixture was then extracted with ethyl acetate (50 mL×2) and the extract was concentrated under reduced pressure. The residue was purified with silica gel column chromatography to give tert-butyl 2-(4-bromophenyl)pyrrolidine-1-formate (1.5 g, yield: 51.1%) as yellow solid.

Step C: At −78° C. under nitrogen atmosphere, to a solution of tert-butyl 2-(4-bromophenyl)pyrrolidine-1-formate (0.6 g, 1.839 mmol) in anhydrous tetrahydrofuran (20 mL) was added n-BuLi (1.5 mL, 2.76 mmol) with stirring. The reaction mixture was stirred at −78° C. for 30 min, to which was slowly added N,N-dimethylformamide (192 mg, 2.63 mmol). The resultant mixture was warmed to room temperature, stirred for a further 30 min and quenched with 3 mL sodium bicarbonate aqueous solution. The mixture was diluted with water (30 mL) and extracted with ethyl acetate (25 mL×3). The combined organic layer was washed with saline, dried with sodium sulfate, filtered and distilled to dryness. The residue was purified with silica gel column chromatography (petroleum ether: ethyl acetate=15:1-10:1) to give tert-butyl 2-(4-formylphenyl)pyrrolidine-1-formate (0.4 g, yield: 79.1%) as colorless oil.

MS (ESI) m/z: 276.0 [M+1⁺].

Preparation of 2-butoxy-7-(4-(pyrrolidine-2-yl)benzyl)-5H-pyrrolo[3,2-d]2pyrimidine-4-amine Step D: 2-butoxy-7-(4-(pyrrolidine-2-yl)benzyl)-5H-pyrrolo[3,2-d]pyrimidine-4-amine was prepared with the procedures of Step E, F according to Example 22.

MS(ESI) m/z: 366.2[M+1⁺].

Preparation of 2-butoxy-7-(4-(1-methylpyrrolidine-2-yl)benzyl)-5H-pyrrolo[3,2-d]pyrimidine-4-amine Step E: 2-butoxy-7-(4-(1-methylpyrrolidine-2-yl)benzyl)-5H-pyrrolo[3,2-d]pyrimidine-4-amine was prepared with the procedures of Step G according to Example 25.

¹HNMR (Methanol-d4, 400 MHz): δ 7.27 (d, J=8.0 Hz, 2H), 7.22 (d, J=8.0 Hz, 2H), 7.03 (s, 1H), 4.30 (t, J=7.4 Hz, 2H), 3.97 (s, 2H), 3.31-3.19 (m, 1H), 3.07-3.03 (m, 1H), 2.31-2.87 (m, 1H), 2.18-2.15 (m, 1H), 2.13 (s, 3H), 1.89-1.72 (m, 5H), 1.54-1.48 (m, 2H), 0.98 (t, J=7.4 Hz, 3H).

MS(ESI) m/z: 380 [M+1⁺].

Example 27

1-(4-((4-amino-2-butoxy-5H-pyrrolo[3,2-d]pyrimidine-7-yl)methyl)phenyl)-4-methylpiperazine-2-one

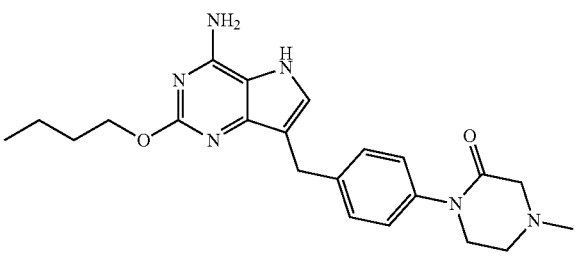 [SMILES: CCCCOc1nc(N)c2[nH]cc(Cc3ccc(N4CCN(C)CC4=O)cc3)c2n1]

Preparation of 4-(4-methyl-2-oxopiperazine-1-yl)benzaldehyde

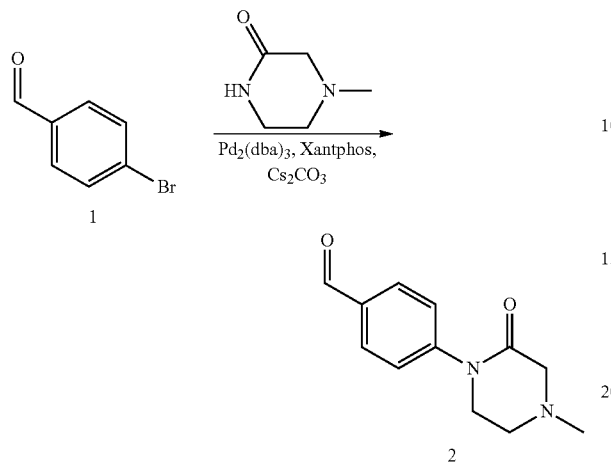

Step A: To a solution of 4-bromo-benzaldehyde (1.8 g, 9.73 mmol), 4-methylpiperazine-2-one (1.44 g, 12.6 mmol), $Pd_2(dba)_3$ (768 mg, 0.84 mmol), Xantphos (435 mg, 0.75 mmol) and cesium carbonate (5.48 g, 16.8 mmol) in dioxan (30 mL) was added water (1 drop). The mixture was stirred under nitrogen atmosphere at 90° C. for 1.5 h. After cooling, the mixture was filtered. The filtrate was concentrated to dryness under vacuum. The residue was purified with silica gel chromatography to give 4-(4-methyl-2-oxopiperazine-1-yl)benzaldehyde (1.8 g, 84.8%) as white solid.

MS(ESI) m/z: 219[M+H$^+$].

Preparation of 1-(4-((4-amino-2-butoxy-5H-pyrrolo[3,2-d]pyrimidine-7-yl)methy)phenyl)-4-methylpiperazine-2-one Step B: 1-(4-((4-amino-2-butoxy-5H-pyrrolo[3,2-d]pyrimidine-7-yl)methyl)phenyl)-4-methylpiperazine-2-one was prepared with the procedures of Step E, F according to Example 22.

$^1$HNMR (Methanol-d4, 400 MHz) δ 7.36 (s, 1H), 7.30 (d, J=8.4 Hz, 2H), 7.22 (d, J=8.4 Hz, 2H), 4.52 (t, J=6.4 Hz, 2H), 4.02 (s, 2H), 3.72-3.69 (m, 2H), 3.27 (s, 2H), 2.89-2.86 (m, 2H), 2.44 (s, 3H), 1.83-1.79 (m, 2H), 1.54-1.48 (m, 2H), 1.00 (t, J=7.4 Hz, 3H).

MS(ESI) m/z: 409[M+H$^+$].

Example 28

2-butoxy-7-((1,2,3,4-tetrahydroisoquinoline-7-yl)methyl)-5H-pyrrolo[3,2-d]pyrimidine-4-amine

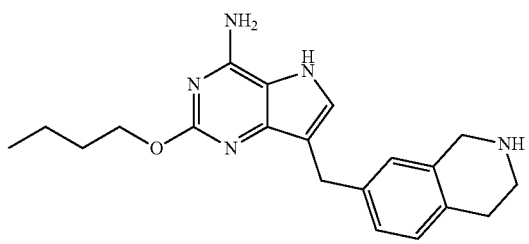 [SMILES: CCCCOc1nc(N)c2[nH]cc(Cc3ccc4c(c3)CNCC4)c2n1]

Scheme for Preparing tert-butyl 7-formyl-3,4-dihydroisoquinoline-2(1H)-carboxylate

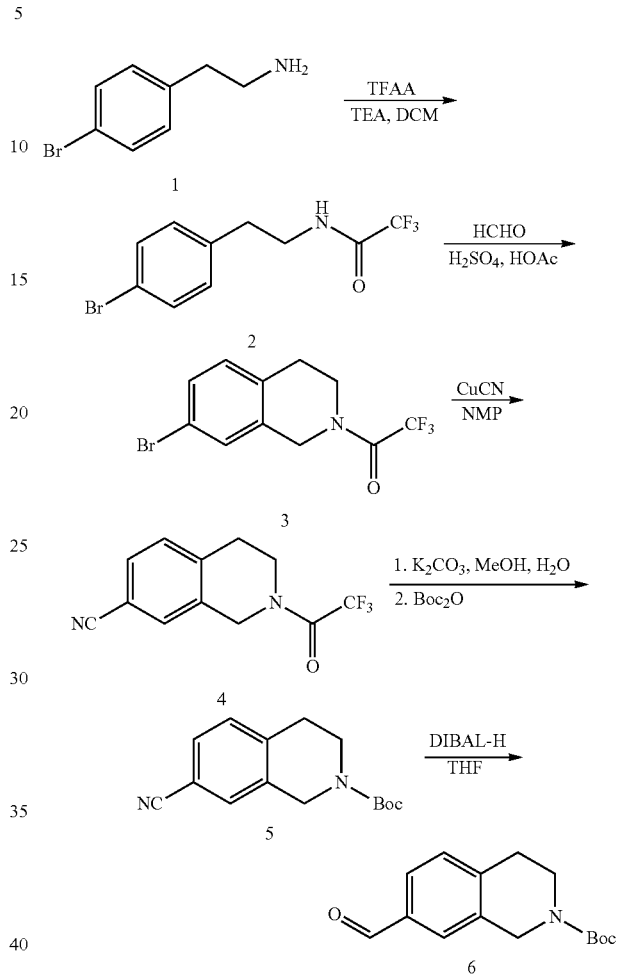

Step A: Under nitrogen atmosphere at 0° C., to a solution of 2-(4-bromophenyl)ethylamine (27 g, 0.13 mol) and triethylamine (16.4 g, 0.16 mol) in anhydrous dichloromethane (300 mL) was added trifluoroacetic acid anhydride (34 g, 0.16 mol) dropwise. The reaction mixture was stirred at room temperature for 1 h and then diluted with water. The organic layer was isolated and concentrated to dryness under vacuum to give N-(4-bromophenethyl)-trifluoroacetamide (37 g, 96.1%) as white solid.

MS(ESI) m/z: 296, 298 [M+H$^+$].

Step B: To a suspension of N-(4-bromophenethyl)-trifluoroacetamide (37 g, 0.12 mmol) in concentrated sulfuric acid (200 mL)/acetic acid (300 mL) was added paraformaldehyde (10.2 g, 0.34 mol) in portions with stirring. After addition, the mixture was stirred at room temperature for 12 h, then poured into ice water (1 L) and extracted with ethyl acetate (400 mL×2). The combined organic layer was successively washed with saturated sodium bicarbonate aqueous solution and saline, dried with anhydrous magnesium sulfate and concentrated under reduced pressure. The residue was purified with silica gel column chromatography (eluent: 5% ethyl acetate in petroleum ether) to give 1-(7-bromo-3,4-dihydroisoquinoline-2 (1H)-yl)-trifluoroethyl ketone (33 g, 89.3%).

MS(ESI) m/z: 308, 310 [M+H$^+$].

Step C: To a solution of 1-(7-bromo-3,4-dihydroisoquinoline-2 (1H)-yl)-trifluoroethyl ketone (30 g, 0.1 mol) in anhydrous methylpyrrolidine-2-one (300 mL) was added cuprous cyanide (18 g, 0.2 mol). The reaction mixture was stirred at 180° C. under nitrogen atmosphere for 4 h. After being cooled to room temperature, the mixture was slowly poured into ice water (500 mL) and extracted with ethyl acetate (200 mL×2). The combined organic layer was washed with water, dried with anhydrous sodium sulfate and concentrated under vacuum to give 25 g of crude 2-trifluoroacetyl-tetrahydroisoquinoline-7-carbonitrile, which was used for the next step directly.

MS(ESI) m/z: 255 [M+H⁺].

Step D: 2-trifluoroacetyl-tetrahydroisoquinoline-7-carbonitrile (25 g, 0.1 mol) and potassium carbonate (25 g, 0.18 mol) were dissolved in mix solvents of methanol (300 mL) and water (60 mL) and the mixture was stirred at room temperature for 2 h. di-tert-butyl dicarbonate (26 g, 0.12 mol) was added in portions over 10 min. The reaction mixture was stirred for a further 4 h, diluted with water (200 mL) and extracted with ethyl acetate (200 mL×2). The combined organic layer was washed with saline, dried with anhydrous sodium sulfate and concentrated under vacuum. The residue was purified with silica gel column chromatography (eluent: 5% ethyl acetate in petroleum ether) to give tert-butyl 7-cyano-3,4-dihydroisoquinoline-2 (1H)-carboxylate (14 g, 54%) as white solid.

MS (ESI) m/z: 259 [M+H⁺].

Step E: Under nitrogen atmosphere at −10° C., to a solution of tert-butyl 7-cyano-3,4-dihydroisoquinoline-2 (1H)-carboxylate (1 g, 3.9 mmol) in anhydrous tetrahydrofuran (20 mL) was added diisobutyl aluminium hydride (1 M, 6 mL, 6.0 mmol) dropwise. After addition, the reaction mixture was stirred at 0° C. for 5 h and quenched with water (0.24 mL). Then 15% sodium hydroxide aqueous solution (0.24 mL) was added followed by 0.6 mL water. The resultant mixture was stirred at room temperature for a further 15 min, dried with anhydrous magnesium sulfate and filtered. The filtrate was concentrated under vacuum and the residue was purified with silica gel column chromatography (eluent: 10% ethyl acetate in petroleum ether) to give tert-butyl 7-formyl-3,4-dihydroisoquinoline-2 (1H)-carboxylate (700 mg, 70%) as yellow oil.

MS(ESI) m/z: 262[M+H⁺].

Preparation of 2-butoxy-7-((1,2,3,4-tetrahydroisoquinoline-7-yl)methyl)-5H-pyrrolo[3,2-d]pyrimidine-4-amine Step F: 2-butoxy-7-((1,2,3,4-tetrahydroisoquinoline-7-yl)methyl)-5H-pyrrolo[3,2-d]pyrimidine-4-amine formate was prepared with the procedures of Step E, F according to Example 22.

¹HNMR (Methanol-4, 400 MHz): δ 8.49 (s, 2H), 7.23-7.15 (m, 3H), 7.10 (s, 1H), 4.44 (t, J=6.5 Hz, 2H), 4.30 (s, 2H), 3.98 (s, 2H), 3.47 (t, J=6.1 Hz, 2H), 3.08 (t, J=6.1 Hz, 2H), 1.83-1.76 (m, 2H), 1.55-1.49 (m, 2H), 1.01 (t, J=7.4 Hz, 3H).

MS(ESI) m/z: 352 [M+H⁺].

Example 29

2-butoxy-7-((2-methyl-1,2,3,4-tetrahydroisoquinoline-7-yl)methyl)-5H-pyrrolo[3,2-d]pyrimidine-4-amine

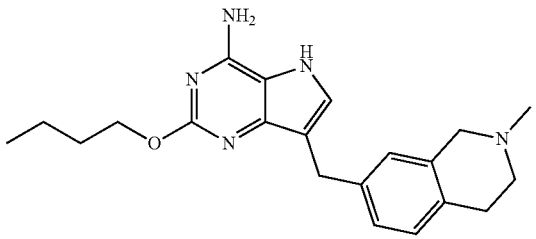 [SMILES: CCCCOc1nc(N)c2[nH]cc(Cc3ccc4c(c3)CN(C)CC4)c2n1]

Using 2-butoxy-7-((1,2,3,4-tetrahydroisoquinoline-7-yl)methyl)-5H-pyrrolo[3,2-d]pyrimidine-4-amine as starting material, with the procedures of Step G according to Example 25, 2-butoxy-7-((2-methyl-1,2,3,4-tetrahydroisoquinoline-7-yl)methyl)-5H-pyrrolo[3,2-d]pyrimidine-4-amine was prepared.

¹HNMR (Methanol-4, 400 MHz): δ 7.11-7.09 (m, 1H), 7.03-7.00 (m, 3H), 4.32 (t, J=6.4 Hz, 2H), 3.92 (s, 2H), 3.55 (s, 2H), 2.91-2.88 (m, 2H), 2.73-2.71 (m, 2H), 2.43 (s, 3H), 1.80-1.73 (m, 2H), 1.56-1.52 (m, 2H), 1.01 (t, J=7.6 Hz, 3H).

MS(ESI) m/z: 366[M+H⁺].

Example 30

2-butoxy-7-((2-ethyl-1,2,3,4-tetrahydroisoquinoline-7-yl)methyl)-5H-pyrrolo[3,2-d]pyrimidine-4-amine

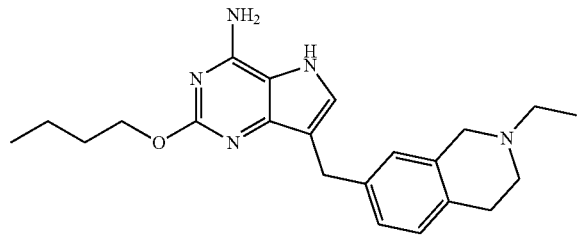 [SMILES: CCCCOc1nc(N)c2[nH]cc(Cc3ccc4c(c3)CN(CC)CC4)c2n1]

Using 2-butoxy-7-((1,2,3,4-tetrahydroisoquinoline-7-yl)methyl)-5H-pyrrolo[3,2-d]pyrimidine-4-amine as starting material, with the procedures of Step G according to Example 25, 2-butoxy-7-((2-ethyl-1,2,3,4-tetrahydroisoquinoline-7-yl)methyl)-5H-pyrrolo[3,2-d]pyrimidine-4-amine formate was prepared.

¹HNMR (Methanol-4, 400 MHz): δ 8.43 (s, 2H), 7.25-7.18 (m, 3H), 7.10 (s, 1H), 4.45 (t, J=6.4 Hz, 2H), 4.34 (s, 2H), 3.99 (s, 2H), 3.51 (t, J=6.0 Hz, 2H), 3.32-3.26 (m, 2H), 3.15 (t, J=6.0 Hz, 2H), 1.84-1.77 (m, 2H), 1.58-1.48 (m, 2H), 1.42 (t, J=8.0 Hz, 3H), 1.01 (t, J=6.0 Hz, 3H).

MS(ESI) m/z: 380[M+H⁺].

Example 31

2-butoxy-7-((2-isopropyl-1,2,3,4-tetrahydroisoquinoline-7-yl)methyl)-5H-pyrrolo[3,2-d]pyrimidine-4-amine

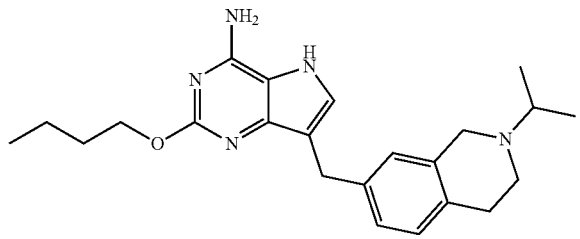 [SMILES: CCCCOc1nc(N)c2[nH]cc(Cc3ccc4c(c3)CN(C(C)C)CC4)c2n1]

Using 2-butoxy-7-((1,2,3,4-tetrahydroisoquinoline-7-yl)methyl)-5H-pyrrolo[3,2-d]pyrimidine-4-amine as starting material, with the procedures of Step G according to Example 25, 2-butoxy-7-((2-isopropyl-1,2,3,4-tetrahydroisoquinoline-7-yl)methyl)-5H-pyrrolo[3,2-d]pyrimidine-4-amine was prepared.

$^1$HNMR (Methanol-4, 400 MHz): δ 7.10-7.08 (m, 1H), 7.03-7.00 (m, 3H), 4.32 (t, J=6.4 Hz, 2H), 3.93 (s, 2H), 3.70 (s, 2H), 2.90-2.86 (m, 3H), 2.83-2.80 (m, 2H), 1.80-1.73 (m, 2H), 1.56-1.50 (m, 2H), 1.17 (d, J=6.4 Hz, 6H), 1.01 (t, J=7.6 Hz, 3H).

MS (ESI) m/z: 394 [M+H$^+$].

Example 32

2-butoxy-7-((1,2,3,4-tetrahydroisoquinoline-6-yl)methyl)-5H-pyrrolo[3,2-d]pyrimidine-4-amine

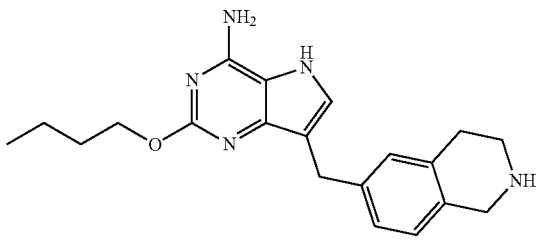 [SMILES: CCCCOc1nc(N)c2[nH]cc(Cc3ccc4c(c3)CCNC4)c2n1]

Scheme for Preparing N-t-butoxycarbonyl 1,2,3,4-tetrahydroisoquinoline-6-formaldehyde

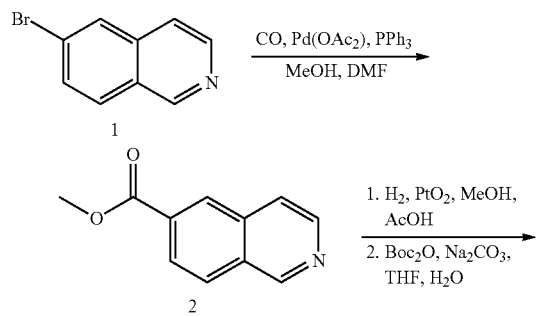

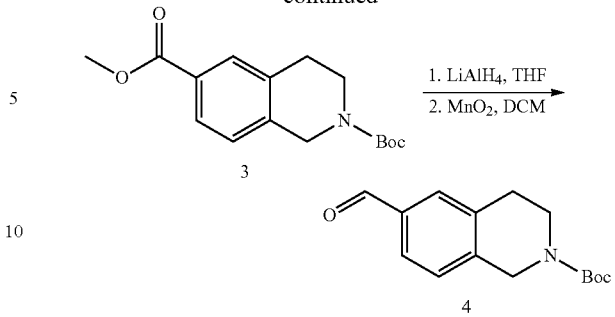

Step A: To a mixed solution of 6-bromoisoquinoline (10 g, 48 mmol) in N,N-dimethylformamide/methanol (V/V=1/1) (200 mL) were added sodium acetate (5.0 g, 61 mmol), triphenylphosphine (3.0 g, 11.4 mmol) and palladium acetate (2.8 g, 12 mmol). The mixture was place in a clave with CO at 300 kPa and heated to 100° C. After stirring for 15 h, completion of the reaction was determined by LC-MS and the reactants were filtered with diatomaceous earth (elution with ethyl acetate). The resultant mixture was concentrated under reduced pressure and purified with silica gel column chromatography (eluent: petroleum ether/ethyl acetate=5/1) to give methyl isoquinoline-6-carboxylate (8.9 g, yield: 98%).

MS(ESI) m/z: 188[M+H$^+$].

Step B: Under nitrogen atmosphere, to a solution of methyl isoquinoline-6-carboxylate (10 g, 53.5 mmol) in methanol (100 mL) were added acetic acid (2 mL) and PtO$_2$ (200 mg) with stirring. Under hydrogen atmosphere, the mixture was stirred at 40° C. for 3 h and the catalyst was filtered off with diatomaceous earth. The mixture was concentrated under vacuum to give methyl 1,2,3,4-tetrahydroisoquinoline-6-carboxylate (9 g, yield: 88%) without further purification.

MS(ESI) m/z: 192 [M+H$^+$].

Step C: methyl N-t-butoxycarbonyl 1,2,3,4-tetrahydroisoquinoline-6-carboxylate was prepared with the procedures of Step C according to Example 25.

MS(ESI) m/z: 292 [M+H$^+$].

Step D: N-t-butoxycarbonyl 1,2,3,4-tetrahydroisoquinoline-6-formaldehyde was prepared with the procedures of Step C, D according to Example 22.

MS(ESI) m/z: 262 [M+H$^+$].

Preparation of 2-butoxy-7-((1,2,3,4-tetrahydroisoquinoline-6-yl)methyl)-5H-pyrrolo[3,2-d]pyrimidine-4-amine Step E: 2-butoxy-7-((1,2,3,4-tetrahydroisoquinoline-6-yl)methyl)-5H-pyrrolo[3,2-d]pyrimidine-4-amine was prepared with the procedures of Step E, F according to Example 22.

$^1$HNMR (Methanol-4, 400 MHz): δ 7.12-7.09 (m, 1H), 7.08 (s, 1H), 7.04 (s, 1H), 6.96 (d, J=7.6 Hz, 1H), 4.32 (t, J=7.4 Hz, 2H), 3.98 (s, 2H), 3.93 (s, 2H), 3.13 (t, J=6.2 Hz, 2H), 2.85-2.82 (m, 2H), 1.79-1.73 (m, 2H), 1.58-1.48 (m, 2H), 1.01 (s, 3H).

MS (ESI) m/z: 352 [M+H$^+$].

Example 33

2-butoxy-7-((2-methyl-1,2,3,4-tetrahydroisoquinoline-6-yl)methyl)-5H-pyrrolo[3,2-d]pyrimidine-4-amine

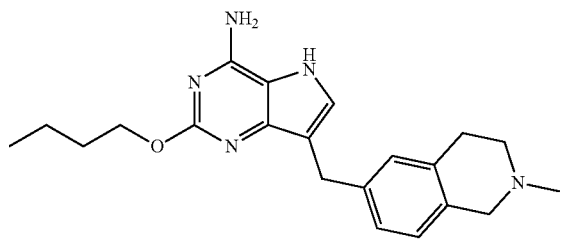 [SMILES: CCCCOc1nc(N)c2[nH]cc(Cc3ccc4c(c3)CCN(C)C4)c2n1]

Using 2-butoxy-7-((1,2,3,4-tetrahydroisoquinoline-6-yl)methyl)-5H-pyrrolo[3,2-d]pyrimidine-4-amine as starting material, with the procedures of Step G according to Example 25, 2-butoxy-7-((2-methyl-1,2,3,4-tetrahydroisoquinoline-6-yl)methyl)-5H-pyrrolo[3,2-d]pyrimidine-4-amine was prepared.

$^1$HNMR (Methanol-4, 400 MHz): δ 7.10-7.09 (m, 2H), 7.03 (s, 1H), 6.96 (d, J=8.4 Hz, 1H), 4.32 (t, J=6.6 Hz, 2H), 3.93 (s, 2H), 3.60 (s, 2H), 2.92-2.89 (m, 2H), 2.77-2.74 (m, 2H), 2.46 (s, 3H), 1.81-1.73 (m, 2H), 1.58-1.48 (m, 2H), 1.01 (t, J=7.4 Hz, 3H).

MS(ESI) m/z: 366[M+H$^+$].

Example 34

2-butoxy-7-((2-ethyl-1,2,3,4-tetrahydroisoquinoline-6-yl)methyl)-5H-pyrrolo[3,2-d]pyrimidine-4-amine

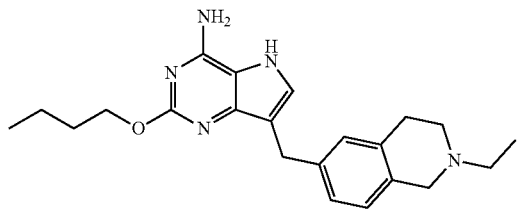 [SMILES: CCCCOc1nc(N)c2[nH]cc(Cc3ccc4c(c3)CCN(CC)C4)c2n1]

Using 2-butoxy-7-((1,2,3,4-tetrahydroisoquinoline-6-yl)methyl)-5H-pyrrolo[3,2-d]pyrimidine-4-amine as starting material, with the procedures of Step G according to Example 25, 2-butoxy-7-((2-ethyl-1,2,3,4-tetrahydroisoquinoline-6-yl)methyl)-5H-pyrrolo[3,2-d]pyrimidine-4-amine was prepared.

$^1$HNMR (Methanol-4, 400 MHz): δ 7.11-7.08 (m, 2H), 7.03 (s, 1H), 6.97 (d, J=8.0 Hz, 1H), 4.32 (t, J=6.6 Hz, 2H), 3.94 (s, 2H), 3.63 (s, 2H), 2.93-2.88 (m, 2H), 2.79-2.76 (m, 2H), 2.65-2.60 (m, 2H), 1.79-1.75 (m, 2H), 1.56-1.52 (m, 2H), 1.21 (t, J=7.2 Hz, 3H), 1.01 (t, J=7.2 Hz, 3H).

MS(ESI) m/z: 380 [M+H$^+$].

Example 35

7-benzyl-2-(2-methoxyethoxyl)-5H-pyrrolo[3,2-d]pyrimidine-4-amine

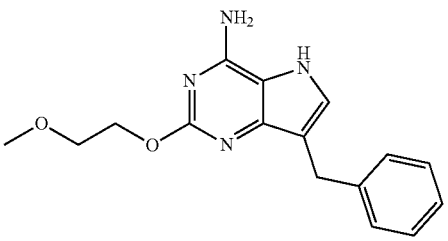 [SMILES: COCCOc1nc(N)c2[nH]cc(Cc3ccccc3)c2n1]

Step A: (4-amino-2-(2-methoxylethoxyl)-5-((2-(trimethylsilylethyl)-5H-pyrrole[3,2-d]pyrimidine-7-yl)(phenyl)methanol was prepared with the procedures of Step C, D, E according to Example 1.

MS(ESI) m/z: 445[M+H$^+$].

Step B: 7-benzyl-2-(2-methoxylethoxyl)-5H-pyrrolo[3,2-d]pyrimidine-4-amine formate was prepared with the procedures of Step G according to Example 1.

$^1$HNMR (Methanol-4, 400 MHz): δ 8.39 (s, 1H), 7.29-7.19 (m, 6H), 4.61-4.58 (m, 2H), 4.00 (s, 1H), 3.79-3.76 (m, 2H), 3.42 (s, 3H).

MS(ESI) m/z: 299[M+H$^+$].

Example 36

2-(2-methoxylethoxyl)-7-((6-methylpyridine-3-yl)methyl)-5H-pyrrolo[3,2-d]pyrimidine-4-amine

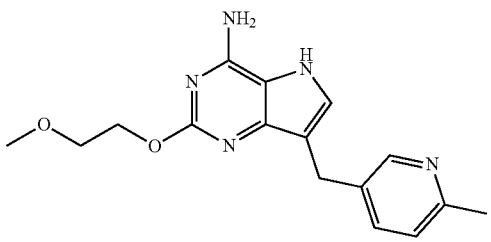

2-(2-methoxylethoxyl)-7-((6-methylpyridine-3-yl)methyl)-5H-pyrrolo[3,2-d]pyrimidine-4-amine formate was prepared with the procedures of Step A, B according to Example 35.

$^1$HNMR (Methanol-4, 400 MHz): δ 8.34 (s, 3H), 7.66 (dd, J=2.4 Hz/J=8.0 Hz, 1H), 7.31 (s, 1H), 7.24 (d, J=8.0 Hz, 1H), 4.57-4.55 (m, 2H), 4.01 (s, 2H), 3.77-3.75 (m, 2H), 3.41 (s, 3H), 2.51 (s, 3H).

MS(ESI) m/z: 314[M+H$^+$].

Example 37

7-((5-chloropyridine-2-yl)methyl)-2-(2-methoxy-lethoxyl)-5H-pyrrolo[3,2-d]pyrimidine-4-amine

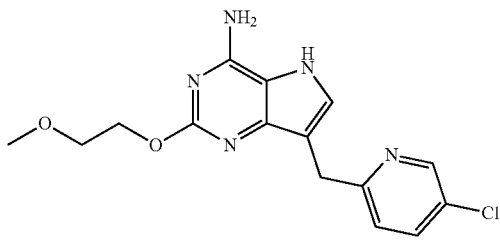 [SMILES: COCCOc1nc(N)c2[nH]cc(Cc3ccc(Cl)cn3)c2n1]

7-((5-chloropyridine-2-yl)methyl)-2-(2-methoxy-lethoxyl)-5H-pyrrolo[3,2-d]pyrimidine-4-amine formate was prepared with the procedures of Step A, B according to Example 35.

$^1$HNMR (Methanol-4, 400 MHz): δ 8.45 (s, 1H), 8.40 (s, 1H), 7.77 (dd, J=2.4 Hz/J=8.0 Hz, 1H), 7.38 (d, J=8.0 Hz, 1H), 7.32 (s, 1H), 4.52 (t, J=4.0 Hz, 2H), 4.17 (s, 2H), 3.75 (t, J=4.0 Hz, 2H), 3.42 (s, 3H).

MS(ESI) m/z: 334[M+H$^+$].

Example 38

2-(2-methoxyethoxyl-)-7-((6-(pyrrolidine-1-ylmethyl)pyridine-3-yl)methyl)-5H-pyrrolo[3,2-d]pyrimidine-4-amine

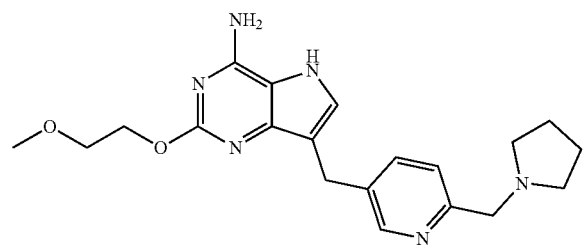 [SMILES: COCCOc1nc(N)c2[nH]cc(Cc3ccc(CN4CCCC4)nc3)c2n1]

2-(2-methoxyethoxyl)-7-((6-(pyrrolidine-1-ylmethyl)pyridine-3-yl)methyl)-5H-pyrrolo[3,2-d]pyrimidine-4-amine formate was prepared with the procedures of Step A, B according to Example 35.

$^1$HNMR (Methanol-4, 400 MHz): δ 8.62 (s, 1H), 8.41 (s, 2H), 7.79-7.76 (m, 1H), 7.36 (d, J=8.4 Hz, 1H), 7.28 (s, 1H), 4.49-4.44 (m, 4H), 4.05 (s, 2H), 3.74-3.72 (m, 2H), 3.39 (s, 3H), 3.33-3.30 (m, 4H), 2.10-2.07 (m, 4H).

MS(ESI) m/z: 383[M+H$^+$].

Example 39

1-(4-((4-amino-2-(2-methoxylethoxyl)-5H-pyrrolo[3,2-d]pyrimidine-7-yl)methyl)phenyl)-4-methylpiperazine-2-one

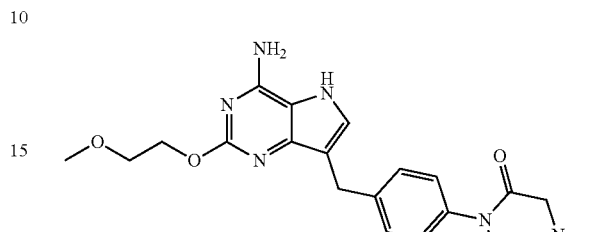

1-(4-((4-amino-2-(2-methoxylethoxyl)-5H-pyrrolo[3,2-d]pyrimidine-7-yl)methyl)phenyl)-4-methylpiperazine-2-one was prepared with the procedures of Step A, B according to Example 35.

$^1$HNMR (Methanol-4, 400 MHz): δ 7.35 (s, 1H), 7.31 (d, J=8.4 Hz, 2H), 7.22 (d, J=8.4 Hz, 2H), 4.65-4.62 (m, 2H), 4.01 (s, 2H), 3.77-3.76 (m, 2H), 3.70-3.67 (m, 2H), 3.35 (s, 3H), 3.32-3.28 (m, 2H), 2.90-2.88 (m, 2H), 2.45 (s, 3H).

MS(ESI) m/z: 411[M+H$^+$].

Example 40

2-butoxy-7-((5-(pyrrolidine-1-ylmethyl)pyridine-2-yl)methyl)-5H-pyrrolo[3,2-d]pyrimidine-4-amine

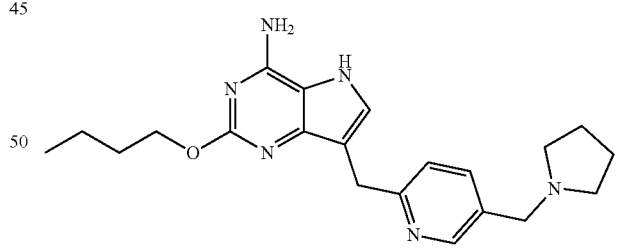

2-butoxy-7-((5-(pyrrolidine-1-ylmethyl)pyridine-2-yl)methyl)-5H-pyrrolo[3,2-d]pyrimidine-4-amine formate was prepared according the procedures of Example 22.

$^1$HNMR (Methanol-4, 400 MHz): δ 8.61 (s, 1H), 8.46 (brs, 2H), 7.91 (d, J=8.0 Hz, 1H), 7.47 (d, J=7.6 Hz, 1H), 7.37 (s, 1H), 4.44 (t, J=6.4 Hz, 2H), 4.35 (s, 2H), 4.22 (s, 2H), 3.33-3.27 (m, 4H), 2.09-2.06 (m, 4H), 1.83-1.76 (m, 2H), 1.57-1.50 (m, 2H), 1.01 (t, J=7.6 Hz, 3H).

MS(ESI) m/z: 381 [M+H$^+$].

Example 41

4-amino-2-butoxy-7-((6-(pyrrolidine-1-ylmethyl)pyridine-3-yl)methyl)-5H-pyrrolo[3,2-d]pyrimidine-6-carbonitrile

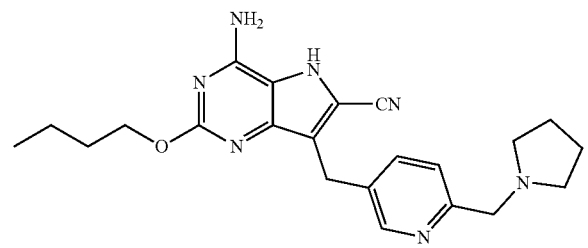 [SMILES: CCCCOc1nc(N)c2[nH]c(C#N)c(Cc3ccc(CN4CCCC4)nc3)c2n1]

Example 41 Procedures

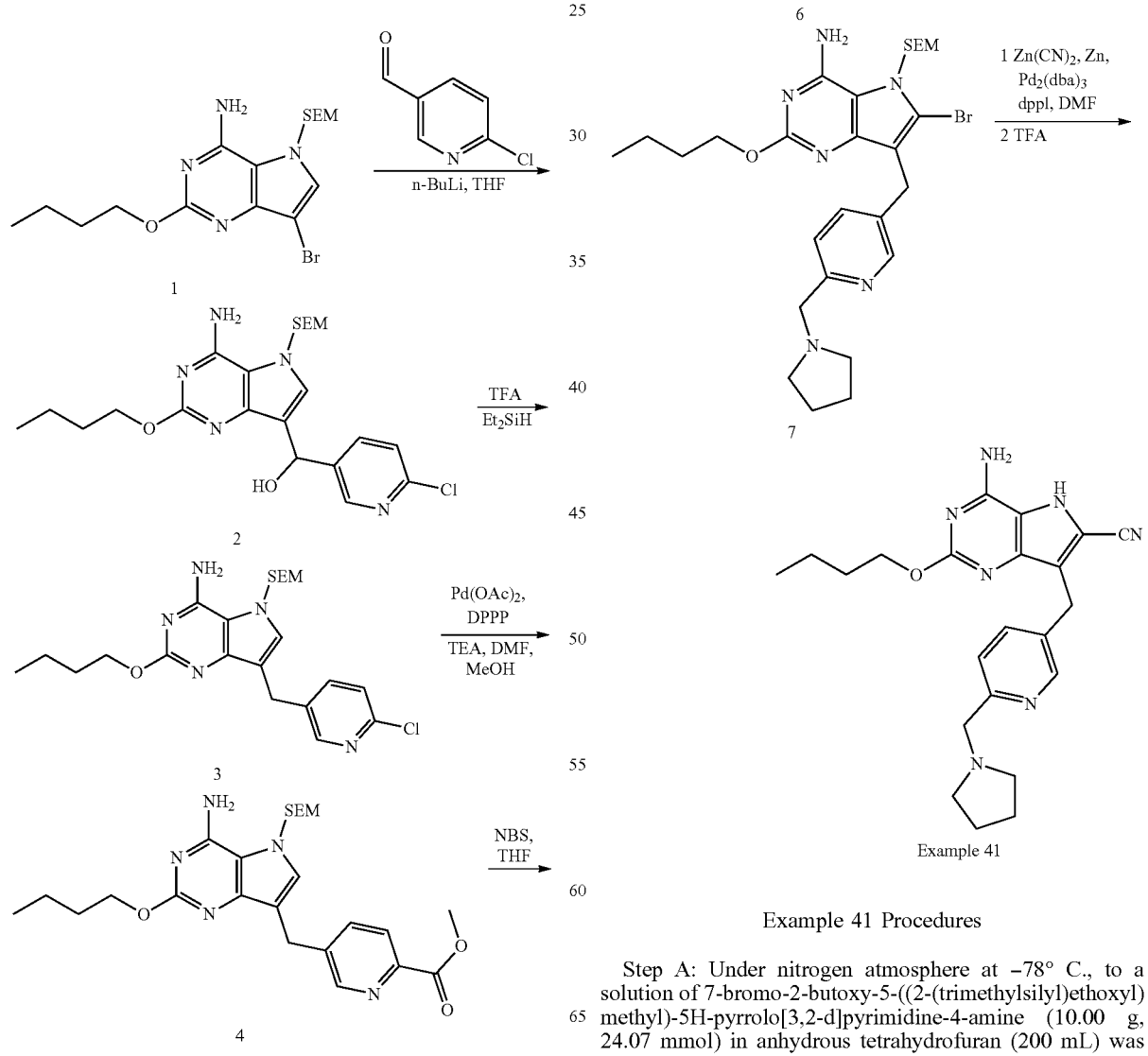

Example 41

Example 41 Procedures

Step A: Under nitrogen atmosphere at −78° C., to a solution of 7-bromo-2-butoxy-5-((2-(trimethylsilyl)ethoxy)methyl)-5H-pyrrolo[3,2-d]pyrimidine-4-amine (10.00 g, 24.07 mmol) in anhydrous tetrahydrofuran (200 mL) was added n-BuLi (6.17 g, 96.28 mmol). The mixture was stirred at −78° C. for 1 h, to which was added a solution of 6-chloronicotinaldehyde (10.22 g, 72.21 mmol) in tetrahydrofuran (200 mL) dropwise. The reaction mixture was stirred at −78° C. for a further 1 h, slowly poured into water (150 mL), stirred at room temperature for 20 min and extracted with ethyl acetate (100 mL×3). The combined organic phase was washed with saturated saline (50 mL×2), dried with anhydrous sodium sulfate, filtered and concentrated under vacuum. The residue was purified with silica gel chromatography (eluent: petroleum ether/ethyl acetate=5/1-1/3) to give (4-amino-2-butoxy-5-((2-(trimethylsilyl)ethoxyl)methyl)-5H-pyrrolo[3,2-d]pyrimidine-7-yl)(6-chloropyridine-3-yl)methanol (5.00 g, 43.45%) as yellow solid.

$^1$HNMR (400 MHz, CHLOROFORM-d) δ 8.52 (d, J=2.3 Hz, 1H), 7.87 (dd, J=2.4, 8.2 Hz, 1H), 7.34 (d, J=8.0 Hz, 1H), 6.65 (s, 1H), 6.14 (s, 1H), 5.97 (br.s., 2H), 5.39-5.26 (m, 2H), 4.31 (t, J=6.7 Hz, 2H), 3.62-3.49 (m, 2H), 1.86-1.71 (m, 2H), 1.51 (qd, J=7.5, 14.9 Hz, 2H), 1.28 (t, J=7.2 Hz, 1H), 1.06-0.87 (m, 5H), 0.00 (s, 9H).

MS(ESI) m/z: 478[M+H$^+$].

Step B: At room temperature, to a solution of (4-amino-2-butoxy-5-((2-(trimethylsilyl)ethoxyl)methyl)-5H-pyrrolo[3,2-d]pyrimidine-7-yl) (6-chloropyridinepyridine-3-yl)methanol (5.00 g, 10.46 mmol) in trifluoroacetic acid (50 mL) was added triethylsilane (6.08 g, 52.30 mmol) in portions. The reaction mixture was stirred at ambient temperature for 24 h, poured into sodium bicarbonate saturated aqueous solution (150 mL) and further stirred for 20 min followed by extraction with ethyl acetate (100 mL×3). The combined organic phase was washed with saline (20 mL×2), dried with anhydrous sodium sulfate, filtered and concentrated under vacuum. The residue was purified with silica gel chromatography (eluent: petroleum ether/ethyl acetate=3/1) to give 2-butoxy-7-((6-chloropyridine-3-yl)methyl)-5-((2-(trimethylsilyl)ethoxyl)methyl)-5H-pyrrolo[3,2-d]pyrimidine-4-amine (2.30 g, 47.59%) as yellow solid.

$^1$HNMR (300 MHz, CHLOROFORM-d) δ 8.52 (d, J=2.3 Hz, 1H), 7.88 (dd, J=2.4, 8.1 Hz, 1H), 7.35 (d, J=8.3 Hz, 1H), 6.64 (s, 1H), 6.14 (s, 1H), 5.89 (br.s., 2H), 5.40-5.23 (m, 2H), 4.31 (t, J=6.6 Hz, 2H), 3.66-3.47 (m, 2H), 1.88-1.70 (m, 2H), 1.60-1.46 (m, 2H), 1.07-0.82 (m, 5H), 0.00 (s, 9H).

MS(ESI) m/z: 462[M+H$^+$].

Step C: To a solution of 2-butoxy-7-((6-chloropyridine-3-yl)methyl)-5-((2-(trimethylsilyl)ethoxyl)methyl)-5H-pyrrolo[3,2-D]pyrimidine-4-amine (2.30 g, 4.98 mmol) in N,N-dimethylformamide (15 mL) was added palladium acetate (111.75 mg, 0.5 mmol), 1,3-bis(diphenylphosphino)propane (205.30 mg, 0.5 mmol), triethylamine (1.51 g, 14.93 mmol) and methanol (797.43 mg, 24.89 mmol). The suspension was vacuumized and aerated with CO several times. The mixture was heated to 100° C. and stirred under CO atmosphere (3 M Pa) for 24 h. Thin-layer chromatography plate (developing agent: petroleum ether/ethyl acetate=1/1) showed depletion of starting materials. Insolubles were filtered off and concentration was performed. The crude product was purified with silica gel chromatography (eluent: petroleum ether/ethyl acetate=1/1) to give methyl 5-((4-amino-2-butoxy-5-((2-(trimethylsilyl)ethoxyl)methyl)-5H-pyrrolo[3,2-d]pyrimidine-7-yl)methyl)picolinate (1.10 g, 45.48%) as yellow solid.

$^1$HNMR (400 MHz, CHLOROFORM-d) δ 8.76 (d, J=1.8 Hz, 1H), 8.06 (d, J=8.0 Hz, 1H), 7.85 (dd, J=2.0, 8.0 Hz, 1H), 6.82 (s, 1H), 5.71 (br.s., 2H), 5.35 (s, 2H), 4.33 (t, J=6.5 Hz, 2H), 4.19-4.08 (m, 3H), 4.00 (s, 3H), 3.60-3.51 (m, 2H), 1.85-1.74 (m, 2H), 1.53 (qd, J=7.4, 15.0 Hz, 2H), 1.28 (t, J=70.2 Hz, 2H), 1.02-0.90 (m, 5H), 0.00 (s, 9H).

MS (ESI) m/z: 486 [M+H$^+$].

Step D: At a temperature below 0° C., to a solution of methyl 5-((4-amino-2-butoxy-5-((2-(trimethylsilyl)ethoxyl)methyl)-5H-pyrrolo[3,2-d]pyrimidine-7-yl)methyl)picolinate (800.00 mg, 1.65 mmol) in tetrahydrofuran (10 mL) was added bromosuccinamide (293.18 mg, 1.65 mmol) in portions. The reaction mixture was stirred at 0° C. for 1 h, diluted with water (30 mL) and extracted with dichloromethane (20 mL×2). The combined organic phase was dried with magnesium sulfate and concentrated under vacuum. The residue was purified with thin-layer chromatography plate to give methyl 5-((4-amino-6-bromo-2-butoxy-5-((2-(trimethylsilyl)ethoxyl)methyl)-5H-pyrrolo[3,2-d]pyrimidine-7-yl)methyl)picolinate (160.00 mg, 17.18%) as yellow solid.

$^1$HNMR (400 MHz, CHLOROFORM-d) δ 8.83 (s, 1H), 8.03 (d, J=8.0 Hz, 1H), 7.86 (d, J=8.0 Hz, 1H), 5.85 (br.s., 2H), 5.55 (s, 2H), 4.34 (t, J=6.5 Hz, 2H), 4.10 (s, 2H), 4.00 (s, 3H), 3.71-3.60 (m, 2H), 1.84-1.72 (m, 4H), 1.59-1.47 (m, 2H), 0.98 (q, J=7.8 Hz, 5H), 0.01 (s, 9H).

MS (ESI) m/z: 565, 567 [M+H$^+$].

Step E: Under nitrogen atmosphere at −78° C., to a solution of methyl 5-((4-amino-6-bromo-2-butoxy-5-((2-(trimethylsilyl)ethoxyl)methyl)-5H-pyrrolo[3,2-d]pyrimidine-7-yl)methyl)picolinate (150.00 mg, 0.266 mmol) in anhydrous tetrahydrofuran (8 mL) was added diisobutyl aluminum hydride (56.28 mg, 0.396 mmol) dropwise with stirring. After addition, the reaction mixture was stirred at −78° C. for 1 h. Then the reaction mixture was quenched with methanol (5 mL), diluted with water (20 mL) and extracted with ethyl acetate (30 mL×2). The combined organic layer was concentrated to dryness under vacuum to give about 150 mg of crude 5-((4-amino-6-bromo-2-butoxy-5-((2-(trimethylsilyl)ethoxyl)methyl)-5H-pyrrolo[3,2-d]pyrimidine-7-yl)methyl)pyridinealdehyde without further purification.

$^1$HNMR (400 MHz, CHLOROFORM-d) δ 10.05 (s, 1H), 8.87 (s, 1H), 7.96-7.80 (m, 2H), 5.72 (br.s, 2H), 5.56 (s, 2H), 4.34 (t, J=6.5 Hz, 2H), 4.12 (s, 2H), 3.71-3.62 (m, 2H), 1.84-1.72 (m, 2H), 1.56-1.48 (m, 2H), 1.06-0.81 (m, 5H), 0.01 (s, 9H).

MS(ESI) m/z: 535, 537[M+H$^+$].

Step F: To a solution of 5-((4-amino-6-bromo-2-butoxy-5-((2-(trimethylsilyl)ethoxyl)methyl)-5H-pyrrolo[3,2-d]pyrimidine-7yl)methyl)pyridinealdehyde (150.00 mg, 0.281 mmol), pyrrolidine (29.94 mg, 0.421 mmol), acetic acid (0.2 mL) in tetrahydrofuran (5 mL) was added sodium cyanoborohydride (35.27 mg, 0.561 mmol) and the mixture was stirred at room temperature for 12 h. The mixture was poured into ice/water mixture (volume ratio=1/1, 15 mL), stirred for 20 min, and extracted with ethyl acetate (40 mL×3). The combined organic phase was washed with saline (20 mL×2), dried with anhydrous sodium sulfate, filtered, and concentrated under reduced pressure. The residue was purified with preparative HPLC to give 150 mg of 6-bromo-2-butoxy-7-((6-(pyrrolidine-1-ylmethyl)pyridine-3-yl)methyl)-5-((2-(trimethylsilyl)ethoxyl)methyl)-5H-pyrrolo[3,2-d]pyrimidine-4-amine as yellow solid.

MS(ESI) m/z: 589, 591[M+H$^+$].

Step G: To anhydrous N,N-dimethylformamide (2 mL) were added 6-bromo-2-butoxy-7-((6-(pyrrolidine-1-ylmethyl)pyridine-3-yl)methyl)-5-((2-(trimethylsilyl)ethoxyl)methyl)-5H-pyrrolo[3,2-d]pyrimidine-4-amine (150.00 mg, 254.39 µmol), Pd$_2$(dba)$_3$ (23.30 mg, 25.44 µmol), 1,1'-bis(diphenylphosphino)ferrocene (14.10 mg, 25.44 µmol), zinc cyanide (59.74 mg, 508.78 µmol) and Zn (33.27 mg, 508.78 µmol), and the mixture was replaced with nitrogen and heated under nitrogen atmosphere to 110° C. for 3 h. After cooling, the mixture was diluted with water (30 mL) and extracted with ethyl acetate (25 mL×3). The combined organic phase was washed with saline (30 mL), dried with anhydrous sodium sulfate and concentrated under vacuum. The residue was purified with preparative TLC to give 4-amino-2-butoxy-7-((6-(pyrrolidine-1-ylmethyl)pyridine-3-yl)methyl)-5-((2-(trimethylsilyl)ethoxyl)methyl)-5H-pyrrolo[3,2-d]pyrimidine-6-carbonitrile (120 mg, 88.05%).

MS(ESI) m/z: 536[M+H$^+$].

Step H: At 20° C. a solution of 4-amino-2-butoxy-7-((6-(pyrrolidine-1-ylmethyl)pyridine-3-yl)methyl)-5-((2-(trimethylsilyl)ethoxyl)methyl)-5H-pyrrolo[3,2-d]pyrimidine-6-carbonitrile (120 mg, 0.224 mmol) in trifluoroacetic acid (5 mL) was stirred at 20° C. for 12 h and concentrated to dryness under vacuum. The residue was purified with preparative HPLC to give 8.7 mg of 4-amino-2-butoxy-7-((6-(pyrrolidine-1-ylmethyl)pyridine-3-yl)methyl)-5H-pyrrolo[3,2-d]pyrimidine-6-carbonitrile.

$^1$HNMR (Methanol-4, 400 MHz): δ 8.52 (s, 1H), 7.79 (d, J=8.0 Hz, 1H), 7.43 (d, J=8.0 Hz, 1H), 4.33 (t, J=6.8 Hz, 2H), 4.17 (s, 2H), 3.76 (s, 2H), 2.61 (s, 4H), 1.82-1.72 (m, 6H), 1.54-1.49 (m, 2H), 1.02-0.99 (t, J=7.2 Hz, 3H).

MS(ESI) m/z: 406 [M+H$^+$].

Example 42

4-amino-2-butoxy-7-(4-(pyrrolidine-1-ylmethyl)benzyl)-5H-pyrrolo[3,2-d]pyrimidine-6-carbonitrile

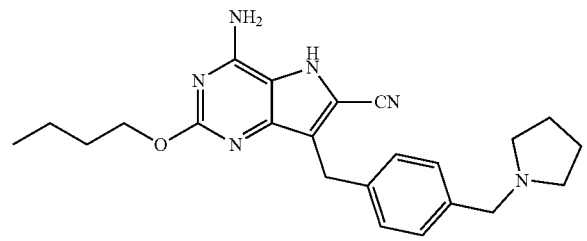 [SMILES: CCCCOc1nc(N)c2[nH]c(C#N)c(Cc3ccc(CN4CCCC4)cc3)c2n1]

4-amino-2-butoxy-7-(4-(pyrrolidine-1-ylmethyl)benzyl)-5H-pyrrolo[3,2-d]pyrimidine-6-carbonitrile was prepared according to the procedures of Example 41 and Step A, B, C, D, E, F, H of Example 41 were followed.

$^1$HNMR (Methanol-4, 400 MHz): δ 7.34-7.32 (d, J=8.4 Hz, 2H), 7.26-7.24 (d, J=8.4 Hz, 2H), 4.36-4.33 (t, J=6.8 Hz, 2H), 4.13 (s, 2H), 3.62 (s, 2H), 2.57 (brs, 4H), 1.82-1.77 (m, 6H), 1.52-1.49 (m, 2H), 1.00 (t, J=7.2 Hz, 3H).

MS(ESI) m/z: 405 [M+H$^+$].

Example 43

4-amino-2-butoxy-7-(4-(morpholinomethyl)benzyl)-5H-pyrrolo[3,2-d]pyrimidine-6-carbonitrile

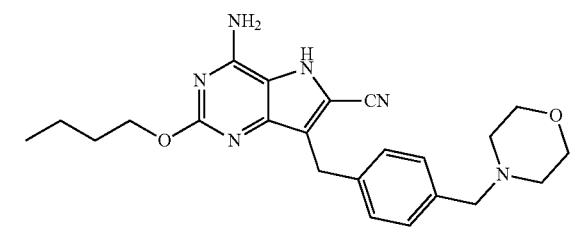 [SMILES: CCCCOc1nc(N)c2[nH]c(C#N)c(Cc3ccc(CN4CCOCC4)cc3)c2n1]

4-amino-2-butoxy-7-(4-(morpholinomethyl)benzyl)-5H-pyrrolo[3,2-d]pyrimidine-6-carbonitrile hydrochloride was prepared according to the procedures of Example 41 and Step A, B, C, D, E, F, G H of Example 41 were followed.

$^1$HNMR (Methanol-4, 400 MHz): δ: 7.55 (d, J=7.8 Hz, 2H), 7.43 (d, J=7.8 Hz, 2H), 4.60 (t, J=6.5 Hz, 2H), 4.38 (s, 2H), 4.23 (s, 2H), 4.06-4.02 (m, 2H), 3.80-3.73 (m, 2H), 3.47-3.35 (m, 2H), 3.28-3.14 (m, 2H), 1.89-1.82 (m, 2H), 1.59-1.51 (m, 2H), 1.03 (t, J=7.4 Hz, 3H).

LCMS(ESI) m/z: 421[M+H$^+$].

Example 44

4-amino-2-butoxy-7-(4-((4-methylpiperazine-1-yl)methyl)benzyl)-5H-pyrrolo[3,2-d]pyrimidine-6-carbonitrile

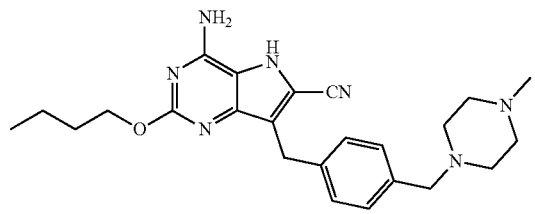 [SMILES: CCCCOc1nc(N)c2[nH]c(C#N)c(Cc3ccc(CN4CCN(C)CC4)cc3)c2n1]

4-amino-2-butoxy-7-(4-((4-methylpiperazine-1-yl)methyl)benzyl)-5H-pyrrolo[3,2-d]pyrimidine-6-carbonitrile hydrochloride was prepared according to the procedures of Example 41 and Step A, B, C, D, E, F, G H of Example 41 were followed.

$^1$HNMR (Methanol-4, 400 MHz): δ: 7.61 (d, J=7.8 Hz, 2H), 7.42 (d, J=7.8 Hz, 2H), 4.60 (t, J=6.5 Hz, 2H), 4.47 (s, 2H), 4.23 (s, 2H), 3.89-3.45 (m, 8H), 3.02 (s, 3H), 1.92-1.80 (m, 2H), 1.61-1.44 (m, 2H), 1.03 (t, J=7.3 Hz, 3H).

LCMS(ESI) m/z: 434 [M+H$^+$].

Example 45

4-amino-2-butoxy-7-(4-(pyrrolidine-1-ylmethyl)benzyl)-5H-pyrrolo[3,2-d]pyrimidine-6-formamide

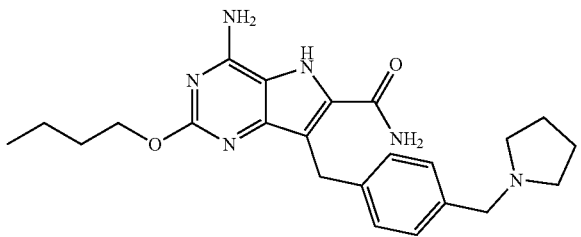 [SMILES: CCCCOc1nc(N)c2[nH]c(C(N)=O)c(Cc3ccc(CN4CCCC4)cc3)c2n1]

Example 45 Procedures

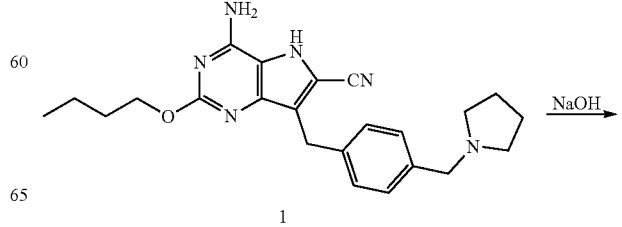

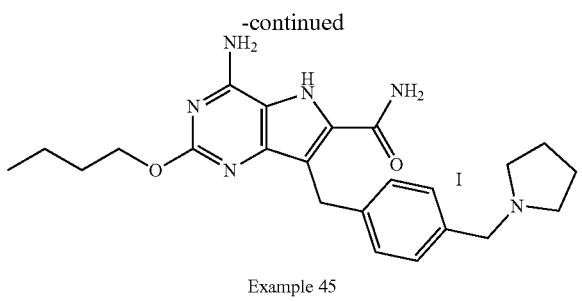

Example 45

Step A: 4-amino-2-butoxy-7-(4-(pyrrolidine-1-ylmethyl)benzyl)-5H-pyrrolo[3,2-d]pyrimidine-6-carbonitrile (90 mg, 0.22 mmol) and sodium hydroxide (34 mg, 0.85 mmol) were dissolved in mixed solvents of methanol (10 mL) and water (10 mL) and the mixture was stirred at 80° C. for 12 h. After cooling, the mixture was diluted with water (10 mL) and extracted with ethyl acetate (15 mL×2). The combined organic layer was concentrated to dryness under vacuum and was purified with preparative HPLC to give 10 mg of 4-amino-2-butoxy-7-(4-(pyrrolidine-1-ylmethyl)benzyl)-5H-pyrrolo[3,2-d]pyrimidine-6-formamide.

$^1$HNMR (Methanol-4, 400 MHz): δ 7.46 (d, J=8.0 Hz, 2H), 7.32 (d, J=8.0 Hz, 2H), 4.58 (t, J=6.4 Hz, 2H), 4.39 (s, 2H), 4.34 (s, 2H), 3.34-3.32 (m, 2H), 3.18-3.16 (m, 2H) 2.17-2.16 (m, 2H), 2.03-2.00 (m, 2H), 1.86-1.82 (m, 2H), 1.56-1.50 (m, 2H), 1.02 (t, J=7.2 Hz, 3H).

MS(ESI) m/z: 423 [M+H$^+$].

Experimental Example 1: Toll-Like Receptor 7 and Toll-Like Receptor 8 In Vitro Receptor Binding Activity Screen Reagents:
HEK-blue hTLR7 cell and HEK-blue hTLR8 cell (available from InvivoGen)
DMEM medium
heat inactivated fetal bovine serum
Anti *Mycoplasma* reagent Normocin™
bleomycin
blasticidin
Scheme:
1. Preparation of 96-well compound plate:
The compounds were gradient diluted with DMSO in 3-fold using liquid work station POD starting at a concentration of 10 mmol/L and 10 points were diluted (2nd column to 11th column, and each point was duplicated). At 12th column, 1 μL of 5 mg/mL positive compound R848 was added as positive control; and at 1st column, 1 μL of DMSO was added as negative control. Each well contained 1 μL of DMSO.
2. The cells in culture flask were collected and the cell density was diluted to 250,000 cells/mL.
3. 200 μL (50,000 cells/well) of cell suspension was added into prepared compound plate and the final concentration of DMSO in each well was 0.5%.
4. The culture plates containing cells and the compounds were incubated in CO$_2$ incubator for 24 h at 37° C., 5% CO$_2$.
5. After 24 h incubation, 20 μL of supernatant was removed from each well to a 96-well transparent assay plate. To each well of the assay plate was added 180 μL of Quanti-Blue reagent and the plate was incubated in an incubator at 37° C., 5% CO$_2$ for 1 h.
6. After 1 h, the content of alkaline phosphatase in 20 μL of supernatant was determined using Microplate Reader OD650.
7. EC$_{50}$ of each compound was obtained with Prism software.

Results were shown in Table 1:

TABLE 1

| compound | TLR7 EC$_{50}$ |
|---|---|
| Example 1 | C |
| Example 2 | C |
| Example 3 | C |
| Example 4 | B |
| Example 5 | C |
| Example 6 | B |
| Example 7 | B |
| Example 8 | B |
| Example 9 | C |
| Example 10 | C |
| Example 11 | B |
| Example 12 | B |
| Example 13 | B |
| Example 14 | B |
| Example 15 | B |
| Example 16 | B |
| Example 17 | B |
| Example 18 | B |
| Example 19 | B |
| Example 20 | B |
| Example 21 | B |
| Example 22 | B |
| Example 23 | C |
| Example 24 | B |
| Example 25 | A |
| Example 26 | B |
| Example 27 | B |
| Example 28 | B |
| Example 29 | B |
| Example 30 | B |
| Example 31 | B |
| Example 32 | B |
| Example 33 | B |
| Example 34 | B |
| Example 35 | C |
| Example 36 | C |
| Example 37 | C |
| Example 38 | B |
| Example 39 | B |
| Example 40 | B |
| Example 41 | A |
| Example 42 | A |
| Example 43 | A |
| Example 44 | A |
| Example 45 | B |

Note:
1 nM ≤ A ≤ 100 nM; 100 nM < B ≤ 1000 nM; 1000 nM < C ≤ 50 μM.

The head-to-head test results of Example 21 compound and control Toll-like receptor 7 agonist GS-9620 were shown in table 2:

TABLE 2

| Sample (title compound) | TLR7 EC$_{50}$ (nM) | TLR8 EC$_{50}$ (nM) |
|---|---|---|
| GS-9620 | 517 | 7867 |
| Example 21 | 160 | 11632 |

Results: Example 21 compound according to the invention showed higher in vitro receptor binding activity to Toll-like receptor 7 than the control Toll-like receptor 7 agonist GS-9620 and lower in vitro receptor binding activity to Toll-like receptor 8 than the control Toll-like receptor 7 agonist GS-9620.

Experimental Example 2: Peripheral Blood Mononuclear Cell Assay

The purpose of this example is to determine the expression level of cytokines 24 h after stimulation to human peripheral blood mononuclear cells (PBMC) with the compounds. The cell supernatant was assayed without dilution and the levels of IFN-α and TNF-α were directly determined. The compound was firstly formulated into 20 mM DMSO stock solution and was gradient diluted with cell medium in 10-fold with the total number of 11 diluting points. The compounds in 9 diluting points (the highest concentration was 200 μmol/L) were added into 96-well plate with 50 μL in each well. Fresh human peripheral blood mononuclear cells were inoculated, with 150 μL in each well containing 450,000 cells. The cell culture plate was incubated in an incubator at 37° C., 5% $CO_2$ for 24 h. After incubation, the culture plate was centrifuged at 1200 rpm for 5 min and the supernatant was collected and stored at −20° C. for determination. The determination of cytokine was performed using Cytometric Bead Array (CBA) of BD-Pharmingen on flow cytometer. Using the above determining method, the lowest drug concentration stimulating cytokine level which is over 3 times greater than the lowest detectable limit was designated as the MEC (Minimal Effective Concentration) value in the cytokine stimulating test.

The results were shown in Table 3:

TABLE 3

| Example | INF-α MEC |
|---|---|
| 4 | C |
| 21 | A |
| 22 | B |
| 28 | B |
| 29 | A |
| 30 | B |
| 31 | B |
| 42 | A |

Note:
0.01 nM ≤ A ≤ 1 nM; 1 nM < B ≤ 10 nM; 10 nM < C ≤ 100 μM.

The head-to-head test results of Example 21 compound and control Toll-like receptor 7 agonist GS-9620 were shown in table 4:

TABLE 4

| Sample (title compound) | INF-α MEC (nM) | TNF-α MEC (nM) |
|---|---|---|
| GS-9620 | 50 | 500 |
| Example 21 compound | 5 | 500 |

Results: Example 21 compound according to the invention showed higher in vitro IFN-α inducing activity than the control Toll-like receptor 7 agonist GS-9620 and comparable TNF-α inducing activity as GS-9620 in PBMC.

Experimental Example 3: Pharmacokinetics in Rat 12 male SD rats were divided into 4 groups with 3 SD rats in each group. 2 groups of animals were administered by intravenous injection 1 mg/kg of the control Toll-like receptor 7 agonist GS-9620 and Example 21 compound according to the invention as 10% hydroxypropyl-β-cyclodextrin aqueous solution (concentration is 0.5 mg/mL), respectively. The other 2 groups were administered orally 5 mg/kg of GS-9620 and Example 21 compound as 0.5% methylcellulose/0.2% Tween 80 pure water suspension (concentration is 1 mg/mL). Each rat with intravenous injection was collected for whole blood samples which were prepared into plasma 2, 15, 30 min and 1, 2, 4, 8, 24 h continuously after administration. Each rat with oral administration was collected for whole blood samples which were prepared into plasma 15, 30 min and 1, 2, 4, 8, 24 h continuously after administration. The plasma concentrations of GS-9620 and Example 21 compound were determined with LC-MS/MS. The results were shown in Table 5.

TABLE 5

| | Mean plasma drug concentration | | | |
|---|---|---|---|---|
| | GS-9620 | | Example 21 compound | |
| compound name Time (h) | IV1 (1 mpk) | PO1 (5 mpk) | IV2 (1 mpk) | PO2 (5 mpk) |
| 0.083 | 170 | — | 318 | — |
| 0.25 | 102 | 56.3 | 141 | 69.4 |
| 0.5 | 65.4 | 33.2 | 109 | 41.6 |
| 1 | 48.1 | 83.4 | 74.3 | 36.4 |
| 2 | 21.6 | 136 | 48.9 | 186 |
| 4 | 13 | 16.7 | 37.7 | 51.2 |
| 8 | 4.17 | 9.49 | 31.6 | 23.9 |
| 24 | ND | ND | 3.94 | 5.25 |
| C0 or Cmax (nM) | 220 | 164 | 478 | 186 |
| $T^{1/2}$ (hr) | 2.57 | 2.24 | 5.76 | 6.24 |
| Vdss (L/kg) | 32.8 | — | 29 | — |
| Cl (mL/min/kg) | 205 | — | 65.8 | — |
| AUC0-last (nM · hr) | 185 | 316 | 641 | 699 |
| AUC0-inf (nM · hr) | 201 | 359 | 676 | 749 |

Results: Under the same condition, Example 21 compound according to the invention, as compared to the control Toll-like receptor 7 agonist GS-9620, showed longer half-life and higher exposure in rat.

Experimental Example 4: In Vivo Pharmacodynamics in Duckling Model Infected with Hepatitis b Virus Experimental design and procedures: Beijing ducks of 1 day old were intravenously administered duck hepatitis b virus positive duck serum. After 7 days, the animals were administered according to grouping, 6 ducks in each group. Control group: normal saline. Test sample: GS-9620 and Example 21 compound, two dosing groups for each sample: 20 mg/kg and 5 mg/kg. The samples were administered intragastricly: 20 mg/kg groups were administered once every third day (one administration every 3 days) and 5 mg/kg groups were administered once every day for 16 days. The positive control drug lamivudine is manufactured by GlaxoSmithKline, as 50 mg/kg for intragastric administration, which was administered twice a day for 16 days. For control group infected with duck hepatitis b virus, solvent was used instead of drug. 7 days after infection, the blood was collected before administration (T0), 8 days after administration (T8), 16 days after administration (T16) and 3 day after ceasing administration (P3), and the duck serum was separated and frozen for storage. Duck serum was used in the determination of duck hepatitis b virus DNA (DHBV-DNA) and the efficacies of GS-9620, Example 21 compound and positive control lamivudine for duck hepatitis b virus were compared. Duck serum DNA (DHBV-DNA) determination; different duck sera in a batch were determined for duck blood DHBV-DNA level with real time fluorescent quantitative PCR. Statistics analysis: paired and grouped analysis was used to calculate the significance of inhibition of drug on duck serum DHBV-DNA for assessment. The efficacies were shown in Table 6.

TABLE 6

| | Duck serum HBV-DNA inhibition % before and after administration | | |
|---|---|---|---|
| Group | T8 | T16 | P3 |
| Control group: normal saline | 32.01 ± 44.57 | 35.96 ± 56.40 | 65.2 ± 16.7 |
| GS-9620 20 mg/kg | 99.13 ± 1.83** | 98.26 ± 1.50** | −132.97 ± 352.35 |
| Example 21 compound 20 mg/kg | 100.0 ± 0** | 98.80 ± 1.84* | 92.81 ± 13.79** |
| GS-9620 5 mg/kg | 98.66 ± 2.75** | 78.02 ± 51.69 | 70.60 ± 47.66 |
| Example 21 compound 5 mg/kg | 99.96 ± 0.06** | 99.36 ± 1.07** | 95.55 ± 3.56** |
| lamivudine 50 mg/kg | 99.76 ± 0.28** | 99.44 ± 0.99** | 95.26 ± 11.20** |

Grouped t-test, as compared to virus control group at the same time point.
*p < 0.05,
**p < 0.01.

Results: As compared to the control Toll-like receptor 7 agonist GS-9620, Example 21 compound according to the invention, under the same condition, showed better efficacies in duckling model infected with hepatitis b virus: for 20 mg/kg (one administration every third day), the inhibition rates are roughly comparable; for 5 mg/kg (one administration everyday), the inhibition rate of Example 21 compound showed significant advantage; 3 days after ceasing administration, GS-9620 20 mg/kg group (one administration every third day) showed rebound of HBV-DNA replication while no rebound was found in the corresponding Example 21 compound group.

Experimental Example 5: In Vivo Pharmacodynamics in HDI (Hydrodynamic Injection) Mouse Model Infected with Hepatitis b Virus Experimental design and procedures:
Route: intragastric administration
Administration time: day 1 to day 7, 7 days in total
Administration groups: group 1: vehicle, 10% HP-β-CD; group 2: GS-9620, 20 mg/kg; groups 3: Example 21 compound, 20 mg/kg
At day 1, 3, 5 and 7, plasma samples were collected 4 h after administration; and at day 7, liver sample was collected 4 h after administration. The details were shown in Table 7.

TABLE 7

| Group | Number of mice in each group | Plasmid (μg/animal) | Plasmid injected and time | compound | dosage (mg/kg) | volume (ml/kg) | Administration route | Time for collecting blood | Time for collecting liver |
|---|---|---|---|---|---|---|---|---|---|
| 1 | 7 | ~20 | HDI pAAV2-HBV 1.3 mer, | Vehicle | / | 10 | intragastric administration, day 1 to day 7, once a day | day 1, 3, 5, 7, 4 h after administation | day 7, 4 h after administration |
| 2 | | | | GS-9620 | 20 | | | | |
| 3 | | | | Example (21) | 20 | | | | |

Figure 2:
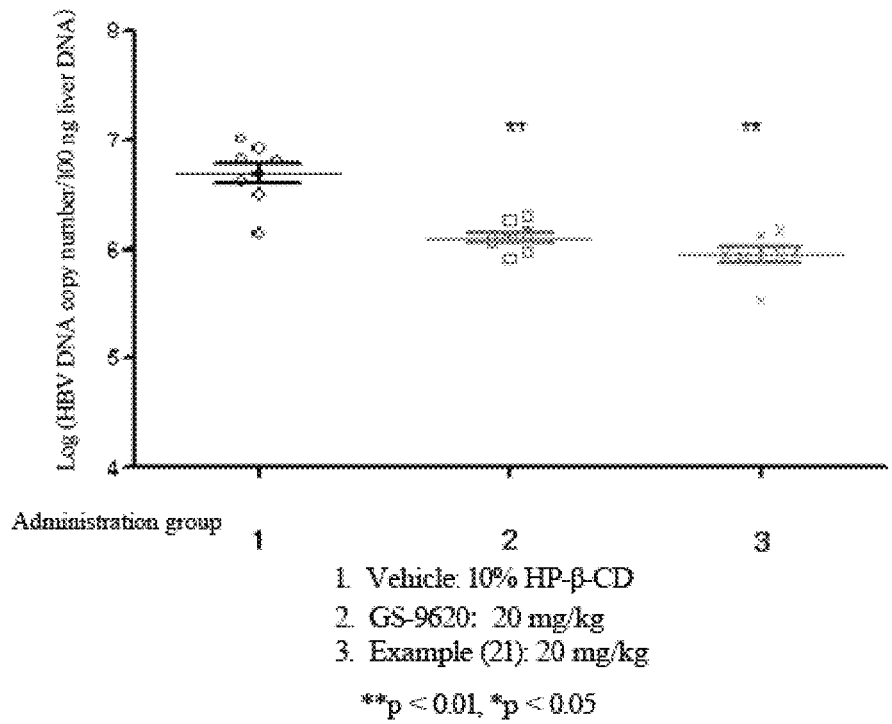
FIG. 2: in vivo pharmacodynamics in HDI mouse model infected with hepatitis b virus (liver).

The detailed results of in vivo pharmacodynamics in HDI (hydrodynamic injection) mouse model infected with hepatitis b virus were shown in FIGS. 1 and 2. Results: The data of HBV copy numbers in plasma and liver showed, Example 21 compound, under the same condition had a better efficacy than the control Toll-like receptor 7 agonist GS-9620.

The invention claimed is:
1. A compound of formula (I) or a pharmaceutically acceptable salt thereof

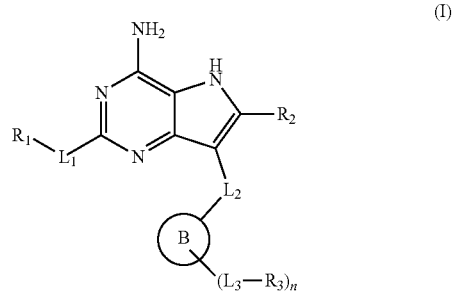

wherein
L$_1$ and L$_2$ are each independently selected from the group consisting of —O— and —CH$_2$—;
R$_1$ is selected from the group consisting of C$_{1-10}$ alkyl, wherein the above C$_{1-10}$ alkyl is optionally substituted by one or more R$_4$;
R$_2$ is selected from the group consisting of hydrogen, cyano and —CONH$_2$, wherein the above —CONH$_2$ is optionally substituted by one or more R$_4$;
B is selected from the group consisting of C$_{3-10}$ cyclohydrocarbyl, 3-10 membered heterocyclohydrocarbyl, aryl and heteroaryl;
L$_3$ is selected from the group consisting of C$_{0-6}$ alkylene, wherein the above C$_{0-6}$ alkylene is optionally substituted by one or more R$_4$;
R$_3$ is selected from the group consisting of hydrogen, amino, C$_{1-10}$ alkyl, C$_{3-10}$ cyclohydrocarbyl, 3-10 membered heterocyclohydrocarbyl, aryl and heteroaryl, wherein the above amino, C$_{1-10}$ alkyl, C$_{3-10}$ cyclohydrocarbyl, 3-10 membered heterocyclohydrocarbyl, aryl and heteroaryl are optionally substituted by one or more R$_4$; or
R$_3$ and L$_3$ together with the adjacent atom at the ring B form a saturated or unsaturated 5-8 membered ring, wherein the 5-8 membered ring is optionally substituted by one or more R$_4$;

n is 0, 1, 2, 3, 4 or 5;

$R_4$ is selected from the group consisting of halogen, —R, —OR and =O;

R is independently selected from the group consisting of H and $C_{1-8}$ alkyl; and when $L_1$ is —$CH_2$—, $R_3$ is not H.

2. The compound according to claim 1, wherein $R_1$ is selected from the group consisting of $C_{1-6}$ alkyl, wherein the above $C_{1-6}$ alkyl is optionally substituted by one or more $R_4$.

3. The compound according to claim 1, wherein B is selected from the group consisting of aryl and heteroaryl.

4. The compound according to claim 3, wherein B is selected from the group consisting of phenyl and pyridyl.

5. The compound according to claim 1, wherein $R_3$ is selected from the group consisting of hydrogen, amino, $C_{1-6}$ alkyl and 3-8 membered heterocyclohydrocarbyl, wherein the above amino, $C_{1-6}$ alkyl and 3-8 membered heterocyclohydrocarbyl are optionally substituted by one or more $R_4$; or $R_3$ and $L_3$ together with the adjacent atom at the ring B form a saturated or unsaturated 5-8 membered ring, wherein the 5-8 membered ring is optionally substituted by one or more $R_4$.

6. The compound according to claim 5, wherein the 3-8 membered heterocyclohydrocarbyl is 5 membered heterocyclohydrocarbyl selected from the group consisting of tetrahydrofuranyl, tetrahydrothiophenyl, pyrrolidinyl, isoxazolidinyl, oxazolidinyl, isothiazolidinyl, 1,1-dioxoisothiazolidinyl, thiazolidinyl, imidazolidinyl, tetrahydropyrazolyl, pyrrolinyl, dihydrofuranyl, dihydrothiophenyl.

7. The compound according to claim 1, wherein $R_2$ is —$CONH_2$; and B is selected from the group consisting of pyridyl and thiazolyl.

8. The compound according to claim 1, wherein $L_1$ is —O—;

$L_2$ is —$CH_2$—;

$R_1$ is $C_{1-4}$ alkyl;

$L_3$ is methylene; and

B and $R_3$ are each independently 5-6 membered heterocyclohydrocarbyl.

9. The compound according to claim 1, wherein $L_1$ is —O—;

$L_2$ is —$CH_2$—;

$R_1$ is $C_{1-4}$ alkyl;

$L_3$ is methylene; and $R_3$ is 5 membered heterocyclohydrocarbyl.

10. The compound according to claim 9, wherein the 5 membered heterocyclohydrocarbyl is selected from the group consisting of tetrahydrofuranyl, tetrahydrothiophenyl, pyrrolidinyl, isoxazolidinyl, oxazolidinyl, isothiazolidinyl, 1,1-dioxoisothiazolidinyl, thiazolidinyl, imidazolidinyl, tetrahydropyrazolyl, pyrrolinyl, dihydrofuranyl, dihydrothiophenyl.

11. A method for treating viral infection, comprising administering the compound according to claim 1 or the pharmaceutically acceptable salt thereof in an effective amount to a subject in need thereof, wherein the viral infection is the infection of dengue fever virus, yellow fever virus, west nile virus, Japanese encephalitis virus, tick borne encephalitis virus, Kunjin virus, Murray Valley encephalitis virus, St Louis encephalitis virus, Omsk Hemorrhagic Fever virus, bovine viral diarrhea virus, Zika virus or hepatitis virus.

12. The method according to claim 11, wherein the viral infection is hepatitis virus infection.

13. The method according to claim 12, wherein the viral infection is hepatitis b or hepatitis c virus infection.

14. A pharmaceutical composition, comprising the compound according to claim 1 or the pharmaceutically acceptable salt thereof in a therapeutically effective amount and one or more pharmaceutically acceptable carriers or excipients.

* * * * *